(12) United States Patent
Sanghamitra

(10) Patent No.: US 12,331,310 B2
(45) Date of Patent: *Jun. 17, 2025

(54) CELL MEMBRANE PENETRATING CONJUGATES FOR GENE EDITING

(71) Applicant: CYGENICA LIMITED, Cork (IE)

(72) Inventor: Nusrat Sanghamitra, Cork (IE)

(73) Assignee: CYGENICA LIMITED, Cork (IE)

( * ) Notice: Subject to any disclaimer, the term of this patent is extended or adjusted under 35 U.S.C. 154(b) by 871 days.

This patent is subject to a terminal disclaimer.

(21) Appl. No.: 17/405,863

(22) Filed: Aug. 18, 2021

(65) Prior Publication Data
US 2022/0056483 A1 Feb. 24, 2022

Related U.S. Application Data

(63) Continuation of application No. PCT/EP2020/055201, filed on Feb. 27, 2020.

(30) Foreign Application Priority Data

Feb. 27, 2019 (GB) ..................... 1902648

(51) Int. Cl.
| | | |
|---|---|---|
| *C12N 15/10* | (2006.01) | |
| *C12N 9/10* | (2006.01) | |
| *C12N 9/22* | (2006.01) | |
| *C12N 9/88* | (2006.01) | |
| *C12N 15/113* | (2010.01) | |
| *C12N 15/90* | (2006.01) | |

(52) U.S. Cl.
CPC ........... *C12N 15/90* (2013.01); *C12N 9/1029* (2013.01); *C12N 9/22* (2013.01); *C12N 9/88* (2013.01); *C12N 15/102* (2013.01); *C12N 15/113* (2013.01); *C07K 2319/04* (2013.01); *C07K 2319/07* (2013.01); *C07K 2319/09* (2013.01); *C12N 2310/20* (2017.05); *C12Y 203/01129* (2013.01); *C12Y 402/02* (2013.01)

(58) Field of Classification Search
CPC ........ A61K 47/65; A61K 47/60; A61K 47/62; C07K 19/00
See application file for complete search history.

(56) References Cited

U.S. PATENT DOCUMENTS

| | | |
|---|---|---|
| 6,008,016 A | 12/1999 | Walker et al. |
| 2006/0269988 A1 | 11/2006 | Royer et al. |

FOREIGN PATENT DOCUMENTS

JP 2005239885 A 9/2005

OTHER PUBLICATIONS

International Search Report for PCT Application No. PCT/EP2020/055201. Mail Date: May 18, 2020. 3 pages.
(Continued)

*Primary Examiner* — Michael D Burkhart
*Assistant Examiner* — Lauren K Van Buren
(74) *Attorney, Agent, or Firm* — Perkins Coie LLP; Viola Kung

(57) ABSTRACT

A genome-editing complex for modifying a target polynucleotide comprising a recombinant β helical protein linked to either one or more molecules of a genome-editing system or a plasmid encoding for one or more molecules of a genome-editing system, wherein the β helical protein length is in the range of from 5 nm to 25 nm, and width is in the range of from 1 nm to 5 nm.

24 Claims, 29 Drawing Sheets
Specification includes a Sequence Listing.

(56) References Cited

OTHER PUBLICATIONS

Inaba, H. et al. "Artificial bio-nanomachines based on protein needles derived from pacteriophage T4" Biophysical Reviews; 2017; vol. 10, No. 2, pp. 641-658.

Ramakrishna, S. et al. "Gene disruption by cell-penetrating peptide-mediated delivery of Cas9 protein and guide RNA" Genome Research, 2014, vol. 24, No. 6, pp. 1020-1027.

Samghamitra, N. et al. "Plasma membrane translocation of a protein needle based on a triple-stranded [beta]-helix motif" Molecular Biosystems; 2014; pp. 2677-2683.

Suresh, B. et al. "Chapter 7: Cell-Penetrating Peptide-Mediated Delivery of Cas9 Protein and Guide RNA for Genome Editing" Methods in Molecular Biology, 2017; vol. 1507; pp. 81-94.

Tuttolomondo, M. et al. "Human DMBT1-Derived Cell-Penetrating Peptides for Intracellular siRNA Delivery" Molecular Therapy—Nucleic Acids; 2017; vol. 8. pp. 264-276.

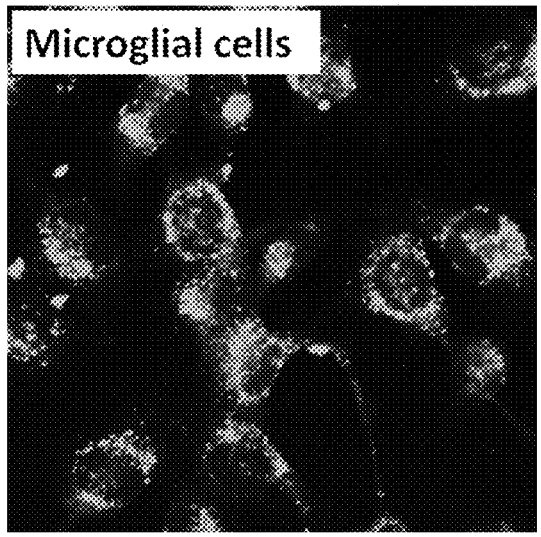 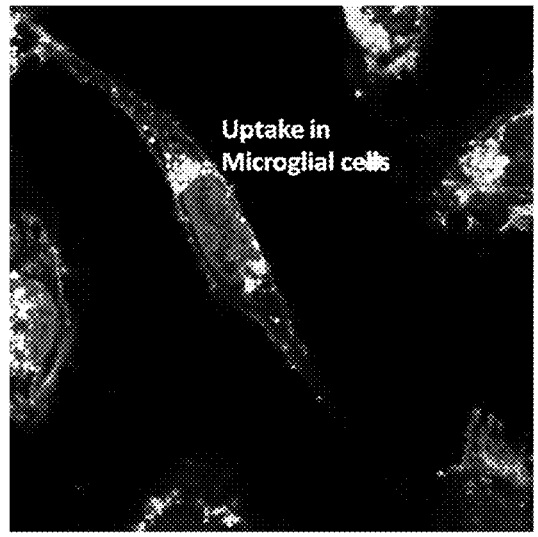
Panel A　　　　　　　　　　　Panel B
Figure 9
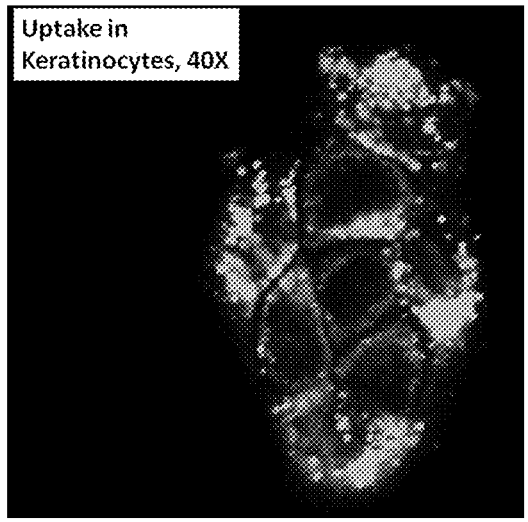 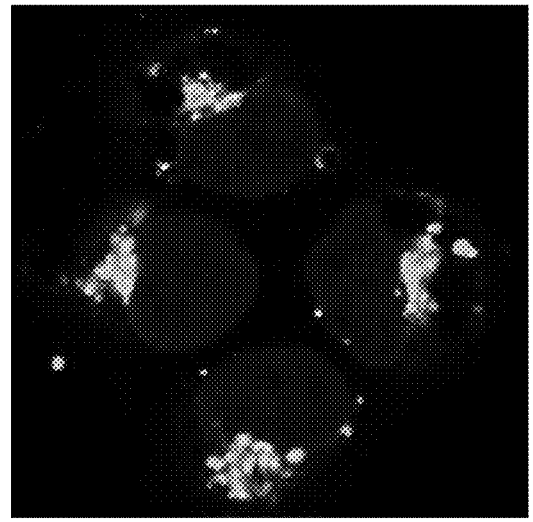
Panel A　　　　　　　　　　　Panel B
Figure 10

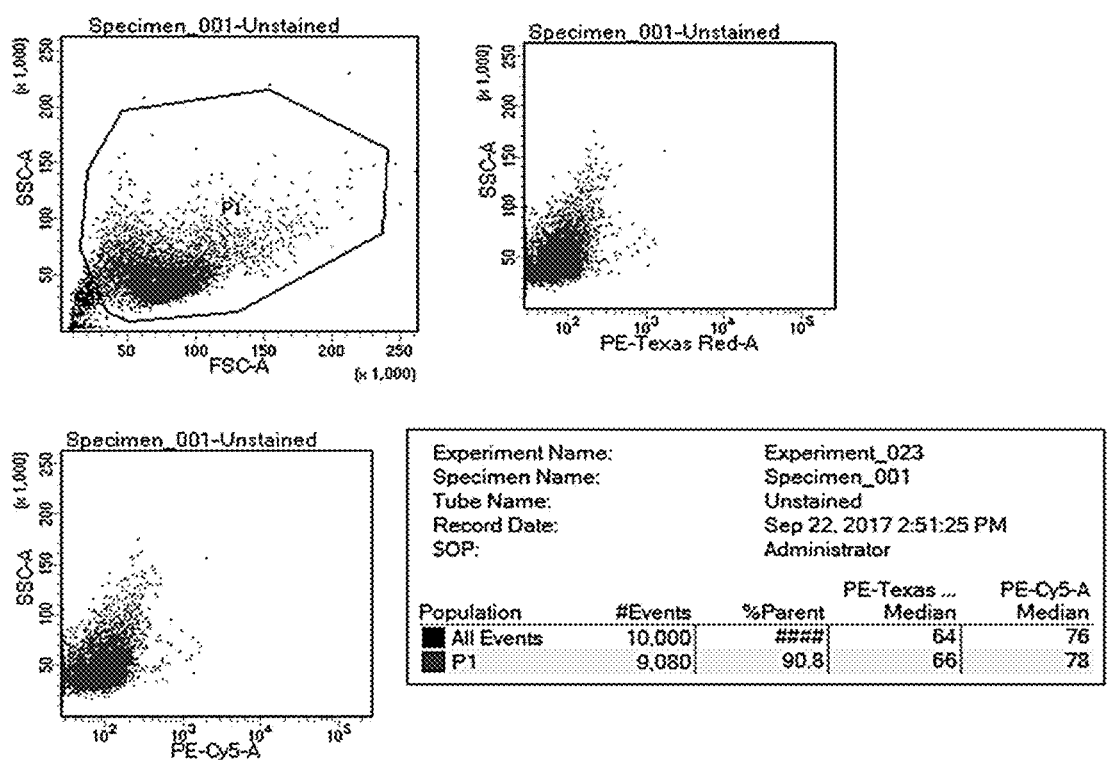
Figure 15: Panel A

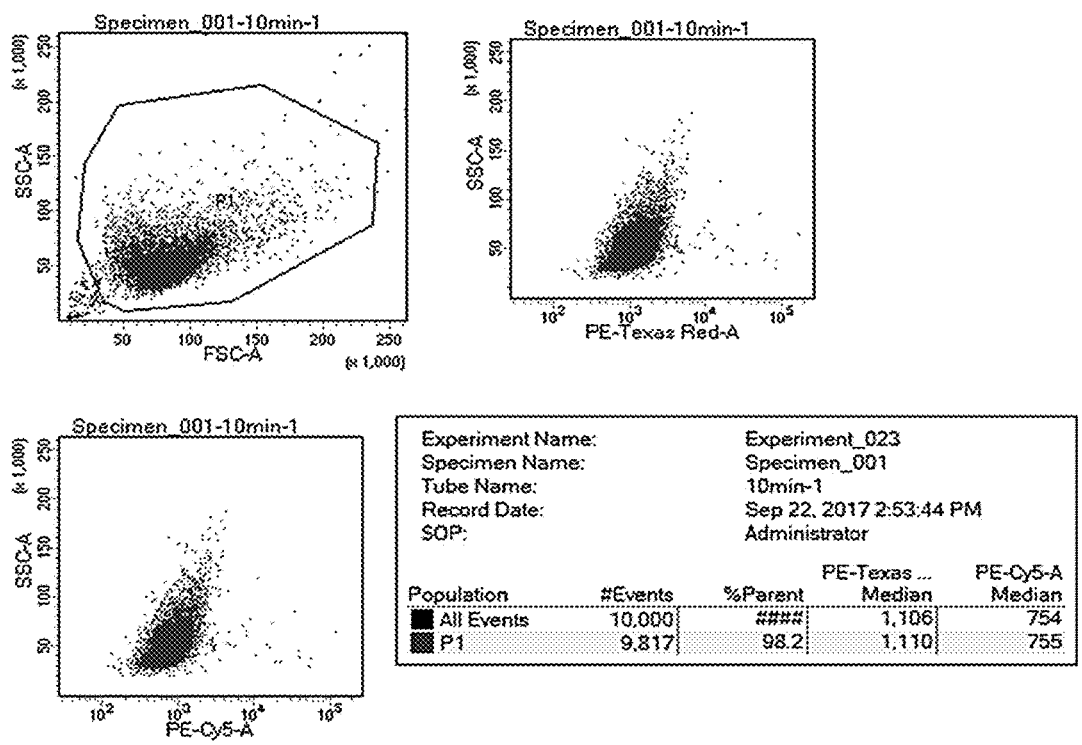
Figure 15: Panel B

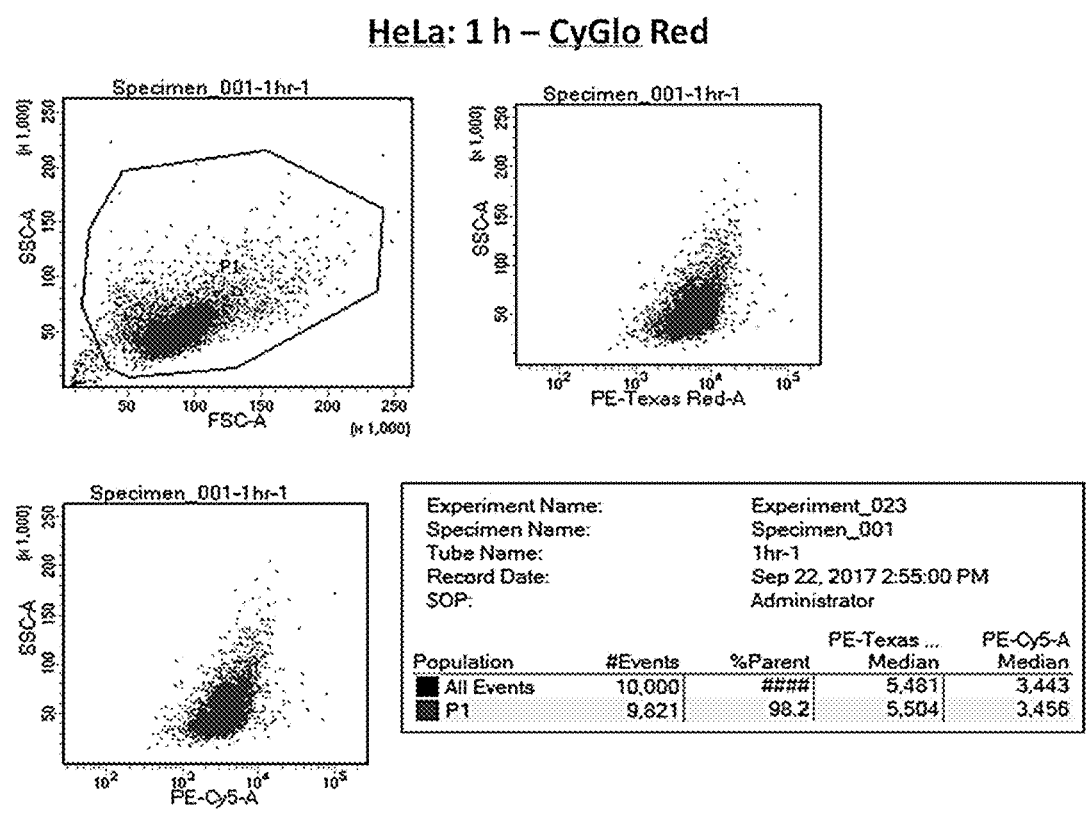
Figure 15: Panel C

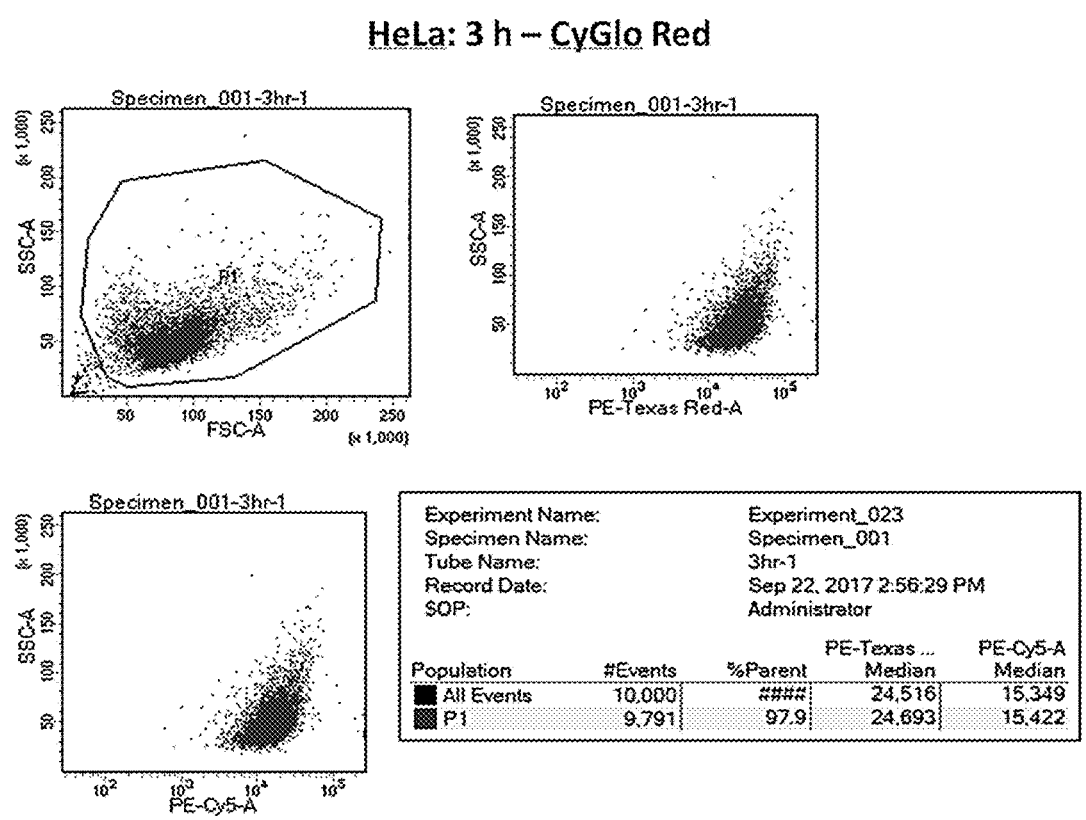
Figure 15: Panel D

A)
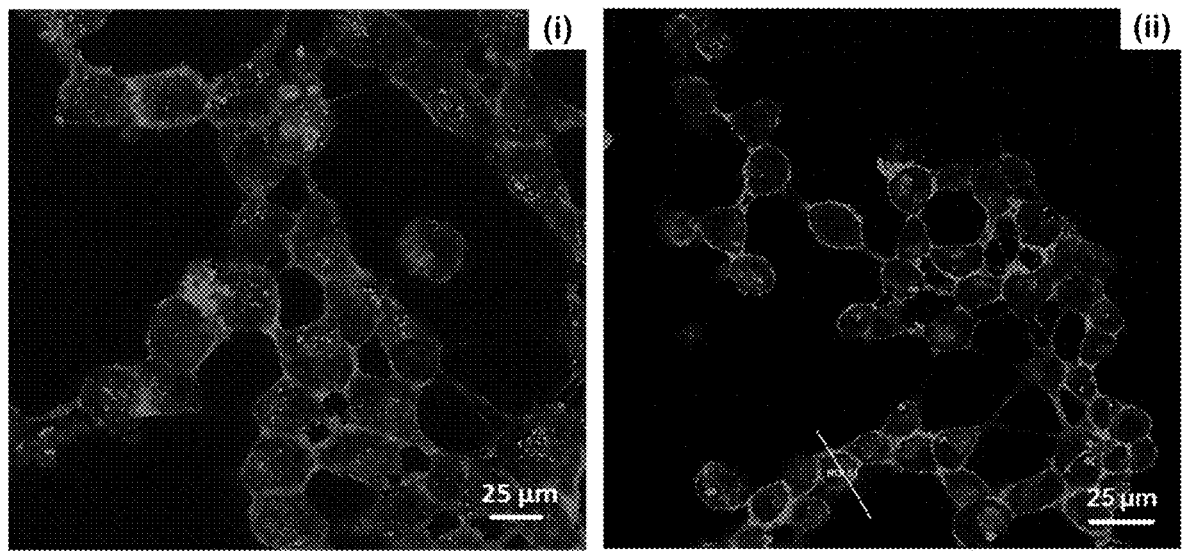
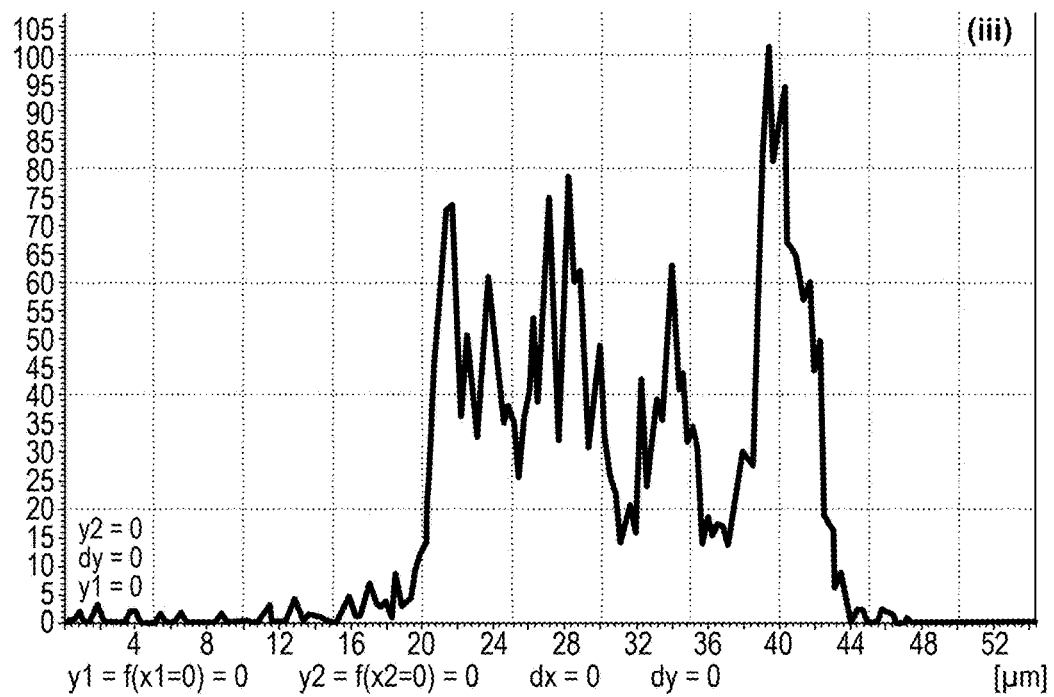
Figure 30

B)
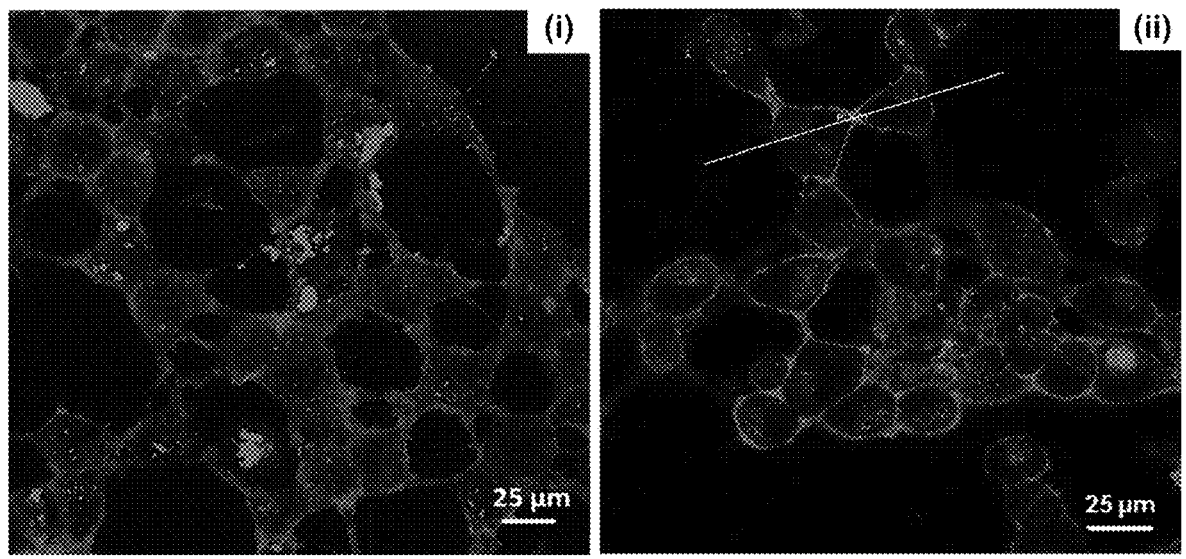
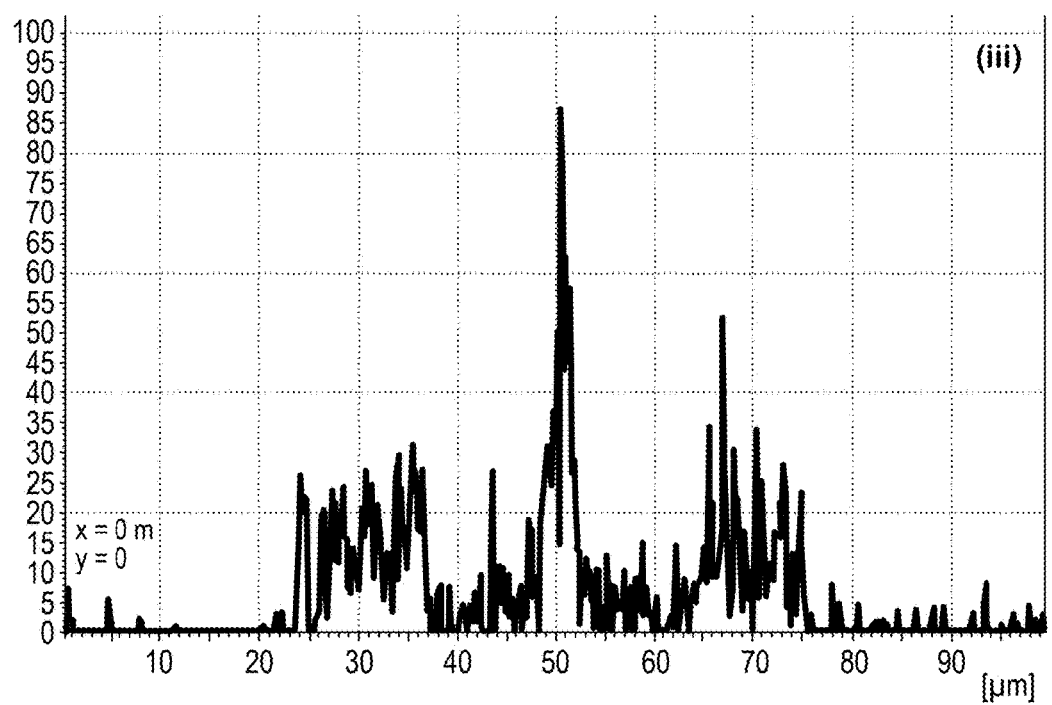
Figure 30 (continued)

CELL MEMBRANE PENETRATING CONJUGATES FOR GENE EDITING

This application is a continuation of PCT/EP2020/055201, filed Feb. 27, 2020; which claims priority of GB1902648,3, filed Feb. 27, 2019. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of SequenceListing.txt with a creation date of Aug. 16, 2021, and a size of 31.2 kilobytes. The Sequence Listing filed via EFS-Web is part of the specification and is hereby incorporated in its entirety by reference herein.

FIELD OF INVENTION

The present disclosure broadly relates to the field of delivery of one or more gene-editing molecules to the cytoplasm of cells and particularly discloses a conjugate comprising a recombinant protein linked to a one or more gene-editing molecules for penetrating cellular membranes, methods of preparing said conjugates and uses thereof. The present disclosure also relates to conjugates comprising a recombinant protein linked to a nucleic acid or plasmid encoding one or more gene-editing molecules for penetrating cellular membranes, methods of preparing said conjugates and uses thereof.

BACKGROUND OF THE INVENTION

A cell membrane is a semi-permeable membrane which separates the inner environment of a cell from its external environment. Membranes of prokaryotic and eukaryotic cells while differing in some properties and composition both comprise a semi-permeable bilayer structure of phospholipids. The semi-permeable nature of the cell membrane makes it selective for the type of molecules able to penetrate it. Those molecules capable of penetrating cell membranes hold promise for use in cell labelling, cell penetration, cell delivery, drug uptake, gene therapy and many other applications which involve penetration of the cell membrane.

There are certain peptides which can penetrate the cell membrane and translocate to the cytosol, such peptides are termed as cell penetrating peptides (CPPs). CPP conjugates, where the CPP is attached to one or more functional molecules, have been studied as a means to transport various biologically active molecules across the membrane. For example, absorption of insulin was drastically increased (6-8 times) in Caco-2 cells when treated with the CPP conjugate, CPP-insulin (Liang et al., Biochem. Biophys. Res. Commun.; 2005; 335(3): 734-738). Similar results were seen for a conjugate comprising the Tat peptide (ibid.). Another study has reported use of a short amphipathic peptide carrier Pep-1 which could penetrate the membrane and deliver various peptides and proteins in several cell lines (Morris et al., Nature Biotechnol., 2001, 1173-1176).

CPPs have also been used to study the efficient delivery of various anti-cancer drugs as drug-CPP conjugates which could penetrate cell membranes more efficiently than the drug alone because of the properties of the CPP. One such study reported the use of Tat protein conjugated with a CK2 inhibitor (P15) to treat solid tumours (Perea et al., Cancer Res. 2004, 7127-7129).

There are also several molecular transporters which can deliver molecules across cell membranes. Guanidinium-rich molecular transporters (GR-MoTrs) comprising peptide and non-peptide agents have been shown to penetrate cell membrane owing to their number and spatial array of guanidinium groups. GR-MoTrs can enhance delivery of various cargos including small molecules, metals, imaging agents, iron particles, and proteins inside mammalian cells (Wender et al., Adv. Drug Deliv. Rev. 2008, 452-472; Wender et al., Drug Discov. Today Technol. 2012, e49-e55).

US20130137644 discloses a conjugate made up of a cell penetrating peptide, nucleic acid and a hydrophilic polymer which can penetrate cell membranes with increased efficiency. The nucleic acid used in the conjugate is described as preferably being an siRNA, with polyethylene glycol (PEG) as the hydrophilic polymer.

US20040176282 discloses methods and uses of compositions for the cellular delivery of nucleic acids, polypeptides, fluorophores, molecular complexes. The intracellular release of the biologically active molecules after cell penetration is stimulated by light-activated dispersal of the complex. This system helps in repressing the biological functions of the molecules while being a part of the complex, but once inside the cell and upon light activation it can be dispersed and its biological activity can be restored.

In addition, and general to the delivery of all functional molecules to the cells, is that most of the mechanisms developed for cellular delivery rely on an endocytosis-dependent mechanism for gaining entry inside the cells. The efficiency of translocation is a major area of concern in endocytosis dependent pathways due to, for example, the possibility of drugs getting trapped in endosomes or degraded in lysosomes. Hence there is a pressing need for devising novel mechanisms for penetrating cell membranes, which can be more reliable and efficacious.

One example of a promising and widely used technique involving functional molecules crossing the cell membrane barrier is genome engineering in which DNA is edited (i.e. one or more nucleotides are inserted, deleted, modified or replaced) in the genome of a living organism.

One type of genome engineering is gene therapy. Gene therapy involves delivering a gene of interest to cells to compensate for abnormal activity of genes or to provide a beneficial protein. Gene therapy has proven beneficial in treating diseases like chronic lymphocytic leukaemia, X-linked SCID, multiple myeloma, haemophilia amongst many others. Many life-threatening diseases have an underlying genetic origin, i.e. the diseases are due to malfunctioning or lack of proper functioning displayed by one or more associated genes. Gene therapy has shown promise for treatment of such disease conditions. However, gene therapy still faces a challenge in terms of delivering the required genes across a cell membrane. To date, two approaches for delivering the genes have been used—viral based and non-viral based.

The viral based approach for gene therapy makes use of attenuated viruses as vectors in which the desired gene is cloned and transferred into the required cells via a process known as transduction. This approach has the advantage of suitable integration of the delivered gene into the genome of the cells but suffers from other disadvantages, one of them being a tendency to induce cancer in case of inappropriate genome integration. The non-viral based approach includes the use of injecting isolated DNA into the cells and the use of cationic lipids for surrounding a plasmid DNA (lipofection). The non-viral approaches do not require any integration of the gene into the genome and are inefficient in transferring the required genes to other cells in the tissues. Therefore gene therapy, although a promising and an excellent technique for treating a number of life-threatening disorders, suffers from the problem of delivery of genes into the cells.

For the most common inherited disorders, such as cystic fibrosis or muscular dystrophy, effective gene therapy is likely to remain a challenge due to the difficulties in delivering the genetic material into the cell. There is not yet a simple way to deliver genes to a significant proportion of cells in tissues such as the lung epithelium or skeletal muscle (Collins et al., Proc. R. Soc. B. Vol. 282. No. 1821. The Royal Society, 2015). Hence, an effective mechanism of cell delivery is required which can greatly enhance the benefits of gene therapy and expand the avenues for providing promising treatments for many life-threatening diseases.

A further type of genome engineering in which functional molecules are required to cross the cell membrane barrier is gene, or genome, editing. Genome editing allows site-specific double-strand breaks to be created at desired locations in the genome, typically through the use of engineered nucleases. These breaks may then be repaired through non-homologous end-joining (NHEJ) or homologous recombination (HR) or homology directed repair (HDR) resulting in site-specific mutations or 'edits' of a genome. Known engineered nucleases include zinc finger nucleases (ZFNs), transcription activator-like effector-based nucleases (TALEN®), homing endonucleases (such as an ARC Nuclease™) or a nucleic acid-guided endonuclease, such as a DNA-guided endonuclease, and RNA-guided endonucleases such as the clustered regularly interspaced short palindromic repeats (CRISPR) system based largely, although not exclusively, on the endonuclease Cas9.

Zinc finger nucleases (ZFNs) are a class of engineered DNA-binding proteins that facilitate targeted editing of the genome by creating double-strand breaks in DNA at user-specified locations. Each Zinc Finger Nuclease (ZFN) consists of two functional domains: a) A DNA-binding domain comprised of a chain of two-finger modules, each recognizing a unique hexamer (6 bp) sequence of DNA. Two-finger modules are stitched together to form a Zinc Finger Protein, each with specificity of >24 bp. b) A DNA-cleaving domain comprised of the nuclease domain of Fok I. When the DNA-binding and DNA-cleaving domains are fused together, a highly-specific pair of 'genomic scissors' are created.

Transcription activator-like effector nuclease (TALEN®) technology leverages artificial restriction enzymes generated by fusing a TAL effector DNA-binding domain to a DNA cleavage domain. Restriction enzymes are enzymes that cut DNA strands at a specific sequence. Transcription activator-like effectors (TALENs®) can be quickly engineered to bind practically any desired DNA sequence. By combining such an engineered TALEN® with a DNA cleavage domain (which cuts DNA strands), one can engineer restriction enzymes that will specifically cut any desired DNA sequence. When these restriction enzymes are introduced into cells, they can be used for gene editing or for genome editing in situ.

CRISPR gene editing utilises a multi component molecular system comprising an endonuclease, typically a Cas or Cpf1 endonuclease, and one or more guide RNA (gRNA) molecules that have the ability to direct said nuclease to specific genome sequences. Where the gRNA hybridizes the genome sequence, the endonuclease acts to cleave the DNA strand. By delivering the Cas9 nuclease complexed with a synthetic gRNA into a cell, the cell's genome can be cut at a desired location, allowing existing genes to be removed and/or new ones added (Ledford, H., Nature, 2015, 522, 7554; Zetsche et al., Cell, 2015, 163(3), 759-771).

A key step of any CRISPR technique is delivering the gRNA and the endonuclease, for example Cas9, into the cytoplasm and/or nucleus of target cells. The delivery of nucleic acids into cells is called transfection. The gRNA and Cas9 can be introduced as either DNA, RNA, or pre-complexed RNA and protein called ribonucleoproteins (RNPs). Transporting foreign materials across multiple cellular barriers (e.g., plasma membrane, nuclear membrane) is a challenge.

Transfection methods can be broadly classified into physical, chemical, and viral-mediated categories. Each method has different advantages and disadvantages with respect to efficiency, throughput, equipment, skill, and cost. The choice of transfection method is also dependent on the format of the CRISPR components.

Translocation of CRISPR gene editing machinery as the pre-formed ribonuceloprotein comprising the Cas9 enzyme with RNA (CRISPR-RNP) means that further transcription or translation is not required prior to gene editing. This can enable editing to occur quickly due to the fewer steps required. This may be useful in some situations, for example in transient transfection where the CRISPR components are introduced into the cell but no DNA encoding a guide RNA or Cas9 are incorporated into the cell's genome. CRISPR-Cas9 can only cleave the cell's genomic DNA for a limited period of time. However, translocation of such a large a diverse set of macromolecules across the cell membrane presents unique challenges in terms of efficiency of transfer across the cell membrane.

Adeno-associated viral particles have commonly been used as gene delivery agents, however due to safety issues and loading capacity limits, viral carriers are non-ideal delivery vehicles (Swiech et al., Nat. Biotechnol., 2015, 33, 102-106). Non-viral means of delivering genome-editing system molecules include lipid-based vectors, lipid nanoparticles, polymeric vectors, polyethylenimine, and poly(L-lysine) to name a few, though application of genome editing (such as by using CRISPR tools) in vivo remains a challenge due to the limitations of the delivery approaches currently being used (Li et al., Human Gene Therapy, 2015, 26(7), 452-462; Wang et al., Proceedings of the National Academy of Sciences, 2016, 113(11), 2868-2873).

Cell penetrating peptides are also known to transport the CRISPR gene editing machinery into cells. WO2017/205846 describes the use of the cell-penetrating peptides VEPEP-3a/b and ADGN-100a/b to facilitate the transfection of the CRISPR-RNP. However, it is made clear that the cell-penetrating peptides VEPEP-9 and CADY are only moderate binders, and the cell-penetrating peptide VEPEP-6 poorly interacts with labelled Cas9 and labelled Cas9-gRNA complexes. It is therefore clear that the choice of CPP is an essential determinant for the efficiency of transfection of gene editing machinery. Cell penetrating peptides used in the literature for gene editing has limited possibility of in vivo use due to immunoreactivity and disruption in the reactivity of Cas9 due to strong electrostatic interaction between positively charged CPP and negatively charged Cas9-gRNA complex. Analytical Biochemistry 345 (2005) 55-65, *Int. J. Mol. Sci.* 2016, 17, 626; doi: 10.3390/ijms17050626

There remains in the art for improved or alternative efficient means for facilitating the transfer of gene editing machinery through the various cellular membranes.

SUMMARY OF INVENTION

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

In a first aspect, the present invention provides a genome-editing complex for modifying a target polynucleotide comprising a class of recombinant β helical protein linked to one or more molecules of a genome-editing system, wherein the β helical protein length is in the range of from 5 nm to 25 nm, and width is in the range of from 1 nm to 5 nm.

In a second aspect, the present invention provides a genome-editing complex for modifying a target polynucleotide comprising a recombinant β helical protein linked to a plasmid that encodes one or more molecules of a genome-editing system, wherein the β helical protein length is in the range of from 5 nm to 25 nm, and width is in the range of from 1 nm to 5 nm.

In embodiments, the one or more molecules of a genome editing system are selected from the group consisting of:
  a. An RNA-guided endonuclease and/or a guide RNA (gRNA);
  b. A zinc finger nuclease (ZFN);
  c. A transcriptor activator-like effector nuclease (TALEN®);
  d. A DNA-guided endonuclease and/or a guide DNA;
  e. A homing endonuclease;
  f. An integrase.

Suitably, the genome editing system is CRISPR-Cas9.

In embodiments, the gRNA has a sequence complementary to a target sequence in the target polynucleotide.

In embodiments, the modification resulting from genome editing is addition, deletion, or substitution of one or more nucleotides in the target polynucleotide.

In embodiments, the β helical protein has a generally quadrangular tip shape with a length in the range of from 5 nm to 25 nm, and a width in the range of from 1 nm to 5 nm.

In embodiments, the β helical protein comprises one or more amino acid ladder structures selected from the group consisting of an arginine ladder; a lysine ladder; an asparagine ladder; an aspartic acid ladder; and a glutamic acid ladder.

In embodiments, the arginine ladder comprises from 10 to 20 arginine residues; the lysine ladder comprises from 10 to 30 lysine residues; the asparagine ladder comprises from 10 to 40 asparagine residues; the aspartic acid ladder comprises from 10 to 40 aspartic acid residues; and the glutamic acid ladder comprises from 10 to 40 glutamic acid residues.

In embodiments, the β helical protein has a total charge that is less than zero.

In embodiments, the β helical protein has a total charge of from −20 to −60.

In embodiments, the β helical protein has a β helical structure with a stiffness parameter K (beta helix) 0.2 to 12 N/m$^2$, as measured by atomic force microscopy.

In embodiments, the β helical protein is a pentapeptide-repeat protein.

In embodiments, the β helical protein comprises tandemly repeated pentapeptide with consensus sequence $(STAV)_1(DN)_2(LF)_3(STR)_4(G)_5$.

In embodiments, the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In embodiments, the recombinant β helical protein is linked to the one or more molecules of a genome-editing system or the plasmid by non-covalent interactions.

In embodiments, the non-covalent interactions are selected from the group comprising hydrogen bonding, electrostatic interactions, van der Waal's interactions, hydrophobic interactions, or combinations thereof.

In embodiments, the recombinant β helical protein is linked to the one or more molecules of a genome-editing system or the plasmid via a linker molecule selected from the group consisting of: polyethyleneglycol (PEG); ethylene diamine; peptide; metal conjugate, drug-metal conjugate, DNA binding domain, nucleic acid intercalating molecule and combinations thereof.

In embodiments, when the linker molecule is a peptide, the peptide comprises amino acids selected from the group consisting of: aliphatic amino acids; aromatic amino acids; and combinations thereof.

In embodiments, the linker is linked to the recombinant β helical protein by covalent bonds, non-covalent bonds, and combinations thereof.

In embodiments, the recombinant β helical protein is linked to the one or more molecules of a genome-editing system or the plasmid via by an ester linkage or an amide linkage.

In embodiments, the genome-editing complex further comprises a signal sequence wherein the signal sequence directs the genome-editing complex to a particular cell or part of a cell.

In embodiments, the signal sequence is selected from the group consisting of SEQ ID NO: 14, SEQ ID NO: 15, SEQ ID NO: 16, and SEQ ID NO: 17.

In embodiments, the genome-editing complex further comprises a phosphatidyl choline molecule.

In embodiments, the genome-editing complex transfers the one or more molecules of a genome-editing system or the plasmid to a location selected from the group consisting of: cell organelles; nucleus; and P-cadherin overexpressing breast cancer cells.

In embodiments, the genome-editing complex is used for genome editing.

In a third aspect, the invention provides a method of preparing the genome-editing complex of the first aspect of the invention, comprising combining the cell-penetrating protein with the one or more genome-editing system molecules, thereby forming the genome-editing complex.

In embodiments of the third aspect of the invention, the one or more genome-editing system molecules is in reaction buffer containing molecules that stabilizes the complex formation between the cell penetrating protein and genome-editing system. The reaction buffer may be selected based on ionic strength to optimise the electrostatic interactions between the various components of the complex. The ionic strength may be varied by choice of components in the buffer solution, for example sodium chloride (NaCl).

Alternatively, in a fourth aspect, the invention provides a method of preparing the genome-editing complex of the second aspect of the invention, comprising combining the cell-penetrating protein with the plasmid, thereby forming the genome-editing complex.

In a fifth aspect, the invention provides a process for transferring one or more molecules of a genome-editing system into a cell, said process comprising:
 a) linking the one or more molecules of a genome-editing system to a recombinant β helical protein to obtain a conjugate or genome-editing complex;
 b) contacting the conjugate or genome-editing complex with at least one cell;
wherein contacting the conjugate or genome-editing complex of step (b) transfers the one or more molecules of a genome-editing system into the cell; and wherein the β helical protein length is in the range of from 5 nm to 25 nm and width is in the range of from 1 nm to 5 nm. Suitably, the process comprises, after step (b), detecting the transfer of the genome-editing complex inside the cell.

In a sixth aspect, the invention provides a process for transferring one or more molecules of a genome-editing system into a cell, said process comprising:
 d) linking a plasmid to a recombinant β helical protein to obtain a conjugate or genome-editing complex;
 e) contacting the conjugate or genome-editing complex with at least one cell;
wherein contacting the conjugate or genome-editing complex of step (d) transfers the plasmid into the cell; and wherein the β helical protein length is in the range of from 5 nm to 25 nm and width is in the range of from 1 nm to 5 nm. Suitably, the process comprises, after step (d), detecting the transfer of the genome-editing complex inside the cell.

In embodiments of the fifth and sixth aspects, the one or more molecules of a genome editing system are selected from the group consisting of:
 a. An RNA-guided endonuclease and/or a guide RNA (gRNA);
 b. A zinc finger nuclease (ZFN);
 c. A transcriptor activator-like effector nuclease (TALEN®);
 d. A DNA-guided endonuclease and/or a guide DNA;
 e. A homing endonuclease;
 f. An integrase.

In embodiments, the genome editing system is CRISPR-Cas9.

In embodiments, the gRNA has a sequence complementary to a target sequence in the target polynucleotide.

In embodiments, the modification resulting from the genome-editing is addition, deletion, or substitution of one or more nucleotides in the target polynucleotide.

In embodiments, the linking the one or more molecules of a genome-editing system to a recombinant β helical protein to obtain a genome-editing complex in step a) is carried out in reaction buffer containing molecules that stabilizes the complex formation between the recombinant β helical protein and the one or more molecules of a genome-editing system; and/or the transfer of the one or more molecules of a genome-editing system into the cell is done in serum free media.

In embodiments, the β helical protein has a generally quadrangular tip shape with a length in the range of from 5 nm to 25 nm, and a width in the range of from 1 nm to 5 nm.

In embodiments, the β helical protein comprises one or more amino acid ladder structures selected from the group consisting of an arginine ladder; a lysine ladder; an asparagine ladder; an aspartic acid ladder; and a glutamic acid ladder.

In embodiments, when present, the arginine ladder comprises from 10 to 20 arginine residues; the lysine ladder comprises from 10 to 30 lysine residues; the asparagine ladder comprises from 10 to 40 asparagine residues; the aspartic acid ladder comprises from 10 to 40 aspartic acid residues; and the glutamic acid ladder comprises from 10 to 40 glutamic acid residues.

In embodiments, the β helical protein has a total charge that is less than zero.

In embodiments, the β helical protein has a total charge of from −20 to −60.

In embodiments, the β helical protein has a β helical structure with a stiffness parameter K (beta helix) 0.2 to 12 $N/m^2$, as measured by atomic force microscopy.

In embodiments, the β helical protein is a pentapeptide-repeat protein.

In embodiments, the β helical protein comprises tandemly repeated pentapeptide with consensus sequence $(STAV)_1 (DN)_2(LF)_3(STR)_4(G)_5$.

In embodiments, the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In embodiments, the genome editing complex is the genome editing complex of the first or second aspect of the invention.

In embodiments, the cell is selected from the group consisting of eukaryotic cells, prokaryotic cells, and combinations thereof.

In embodiments, the eukaryotic cells are mammalian cells, bacterial cells, yeast cells, plants cells, insect cells, or fish cells.

In a seventh aspect, the invention provides a method of modifying a target polynucleotide in a cell, comprising contacting the cell with the genome-editing complex of the first or second aspect, wherein the genome-editing complex targets a sequence in the target polynucleotide.

In an eighth aspect, the invention provides a pharmaceutical composition comprising the genome-editing complex of the first or second aspect of the invention.

In a ninth aspect, the invention provides a method of treating a disease in an individual comprising administering to the individual an effective amount of the pharmaceutical composition of the seventh aspect of the invention.

In a tenth aspect, the invention provides for the use of the genome editing complex of the first or second aspect of the invention for gene editing.

In an eleventh aspect, the invention provides for the use of the genome editing complex of the first or second aspect of the invention for gene therapy.

Also disclosed herein is a cell-penetrating conjugate comprising at least one recombinant β helical protein molecule linked to a functional molecule, wherein the β helical protein length is in the range of 5 nm-25 nm, suitably, 10 nm-15 nm and width is in the range of 1 nm-5 nm, suitably 1 nm-3 nm.

Further disclosed is a process for transferring a functional molecule into a cell, said process comprising: (a) linking the functional molecule to a recombinant β helical protein to obtain a conjugate; and (b) contacting the cell-penetrating conjugate with at least one cell; wherein contacting the conjugate with the at least one cell transfers the nucleic acid molecule into the cell, and wherein the β helical protein length is in the range of 5 nm-25 nm, suitably, 10 nm-15 nm and width is in the range of 1 nm-5 nm, suitably 1 nm-3 nm.

Also disclosed herein is use of the cell penetrating conjugate of the first aspect of the invention for delivering a functional molecule into cells, wherein the functional molecule is selected from the group consisting of dyes, drugs, metal, drug-metal, proteins, enzymes, antibodies, nucleic acids, polysaccharides, nuclear localising signals, nanoparticles and combinations thereof.

Further disclosed herein is use of the cell penetrating conjugate of the first aspect of the invention for cell penetration.

In addition, disclosed herein is use of the cell penetrating conjugate of the first aspect of the invention for cell labelling.

Also disclosed herein is a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm.

Further disclosed herein is a process for transferring a nucleic acid molecule into a cell, said process comprising: (i) linking the nucleic acid molecule to at least one recombinant β helical protein via at least one linker to obtain a conjugate; and (ii) contacting the conjugate with at least one cell, wherein contacting the conjugate with the at least one cell transfers the nucleic acid molecule into the cell, and wherein the recombinant β helical protein length is in the range of 5 nm-25 nm, suitably, 10 nm-15 nm and width is in the range of 1 nm-5 nm, suitably 1 nm-3 nm.

In addition, disclosed herein is use of the cell penetrating conjugate of the sixth aspect of the invention as a transfecting agent.

Further disclosed herein is use of the cell penetrating conjugate of the sixth aspect of the invention for gene therapy.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

Figure 7:
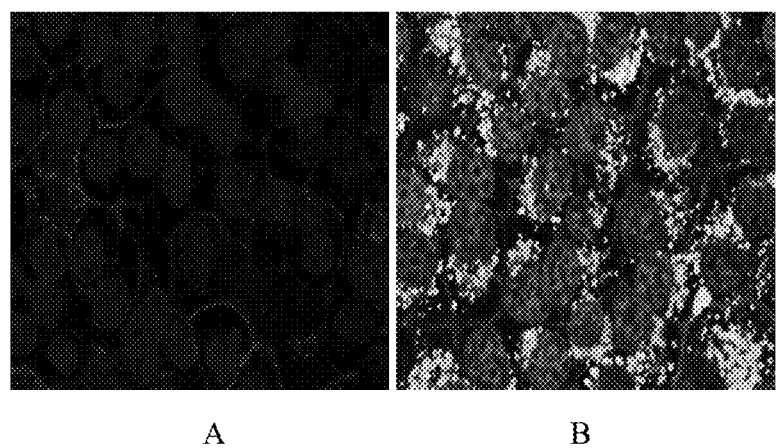

FIG. 7 shows labelling of Hela cells by EfsQNR labelled with ATTO-520, in accordance with an embodiment of the present disclosure. Panel A shows HeLa cells which are not treated with the conjugate. Panel B shows an EfsQNR-ATTO-520NHS conjugate in accordance with the invention penetrating HeLa cells to lead to efficient labelling of the cells when compared to control.

Figure 8:
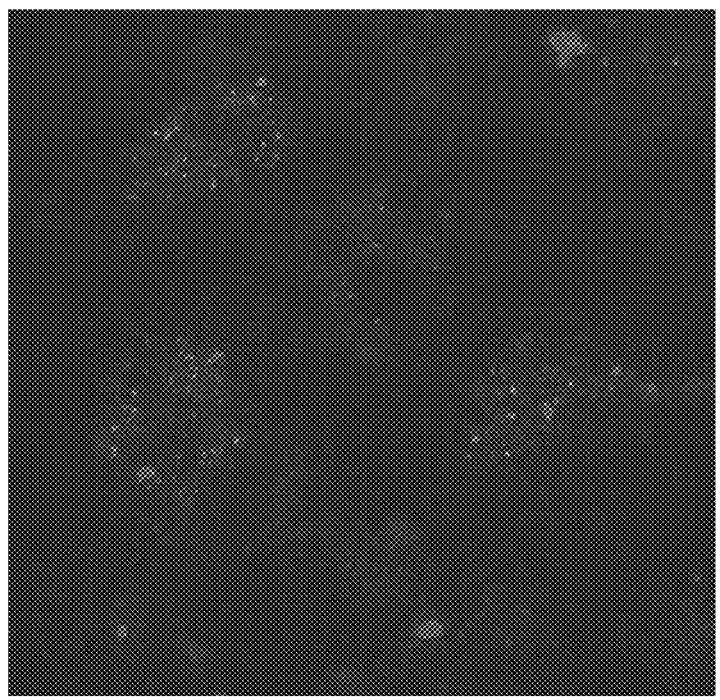

FIG. 8 shows labelling of Hela cells by EfsQNR labelled with ATTO-390, in accordance with an embodiment of the present disclosure.

FIG. 9 shows labelling of microglial cells by EfsQNR labelled with ATTO-520, in accordance with an embodiment of the present disclosure (Panel A); and differential labelling of microglial cells by EfsQNR labelled with ATTO-520 (Panel B).

FIG. 10 shows labelling of keratinocyte cells by EfsQNR labelled with ATTO-520, in accordance with an embodiment of the present disclosure (Panel A); and differential labelling of keratinocyte cells by EfsQNR labelled with ATTO-520 (Panel B).

Figure 11:
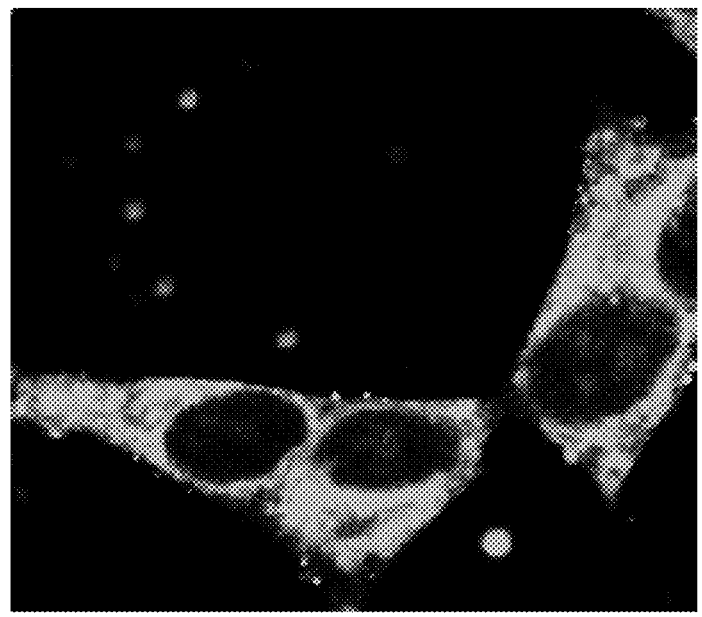

FIG. 11 shows labelling of SH-SY5Y cells by EfsQNR labelled with ATTO-520, in accordance with an embodiment of the present disclosure.

Figure 12:
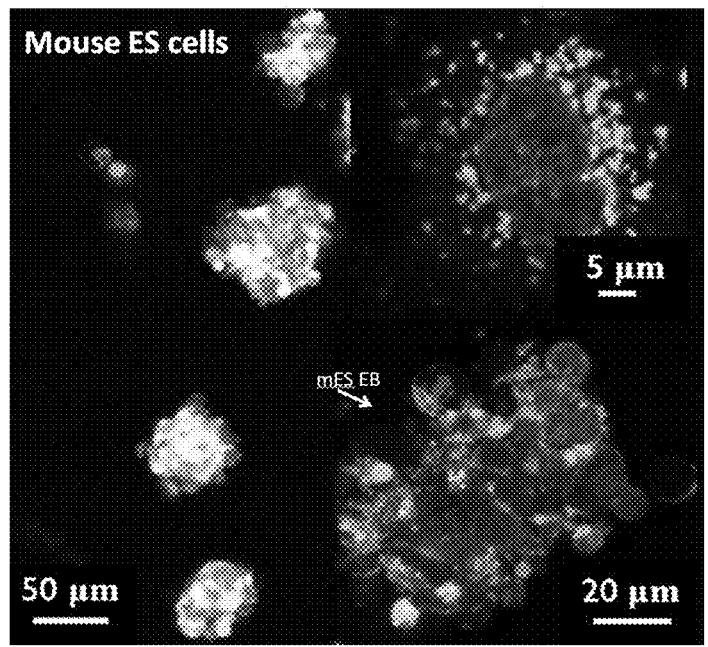

FIG. 12 shows labelling of mouse ES cells by EfsQNR labelled with ATTO-520, in accordance with an embodiment of the present disclosure.

Figure 13:
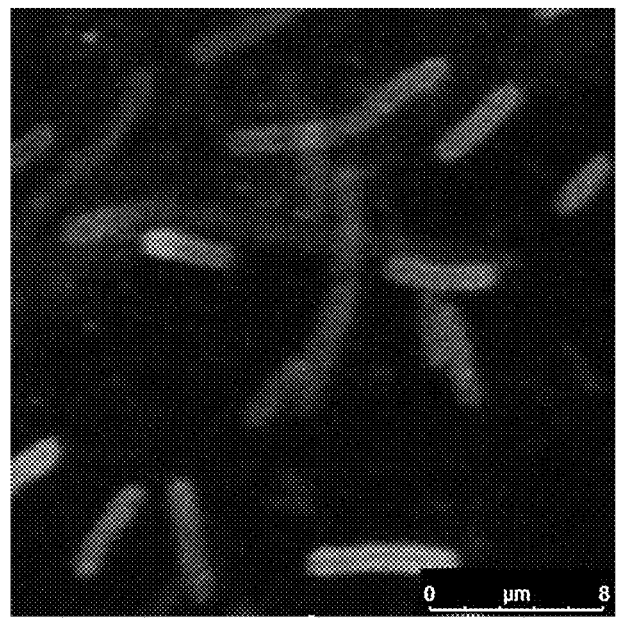

FIG. 13 shows labelling of *E. coli* cells by EfsQNR labelled with ATTO-520, in accordance with an embodiment of the present disclosure.

Figure 14:
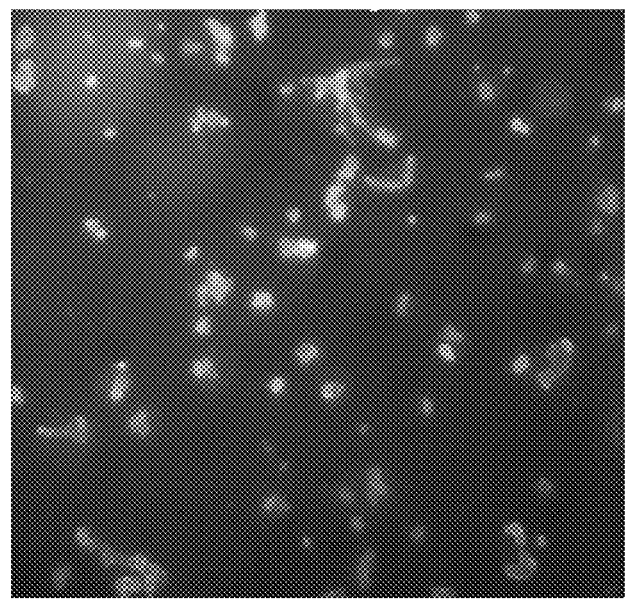

FIG. 14 shows labelling of yeast (kluveromyces) cells by EfsQNR labelled with ATTO-520), in accordance with an embodiment of the present disclosure.

FIG. 15 shows the results of standard FACS sorting of HeLa cells treated with a conjugate labelled with the conjugate EfsQNR-ATTO-647N for 10 mins (Panel B), 1 h (Panel C) and 3 h (Panel D) compared to untreated cells (Panel A).

Figure 16:
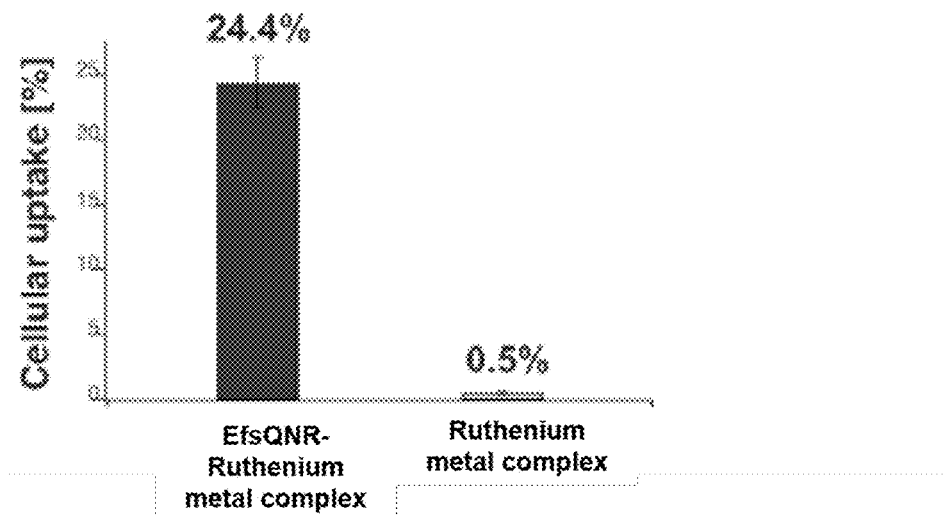

FIG. 16 shows percentage cellular uptake of a drug as part of a conjugate in accordance with an embodiment of the present disclosure, as compared to unconjugated drug.

Figure 17:
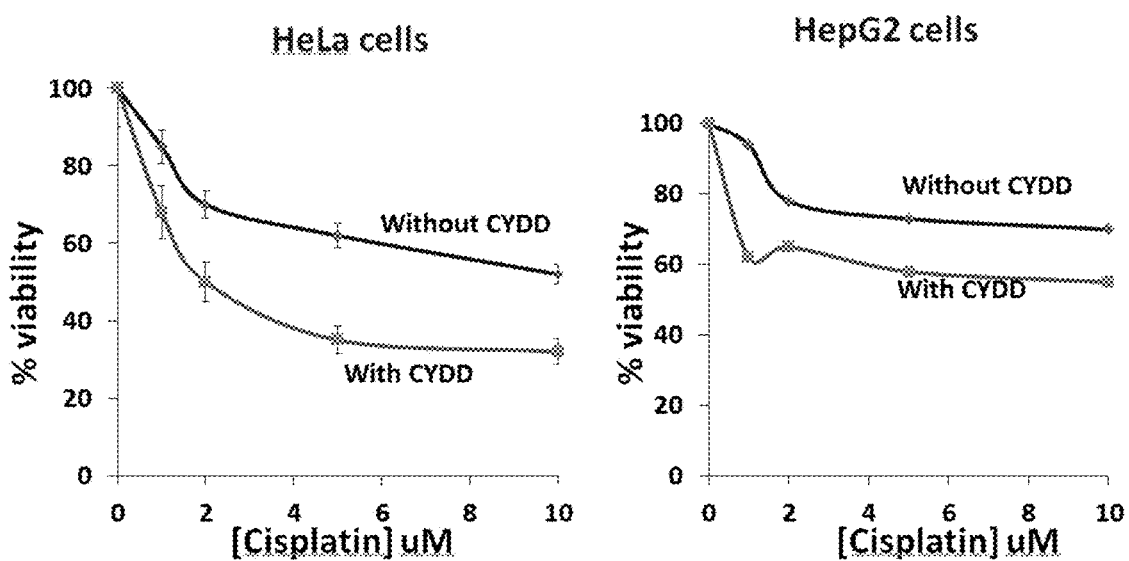

FIG. 17 shows percentage viability of cells (Hela and HepG2) after treatment with Cisplatin® a chemotherapy drug as part of a conjugate with the protein EfsQNR (labelled CYDD) in accordance with an embodiment of the present disclosure, as compared to unconjugated drug.

Figure 18:
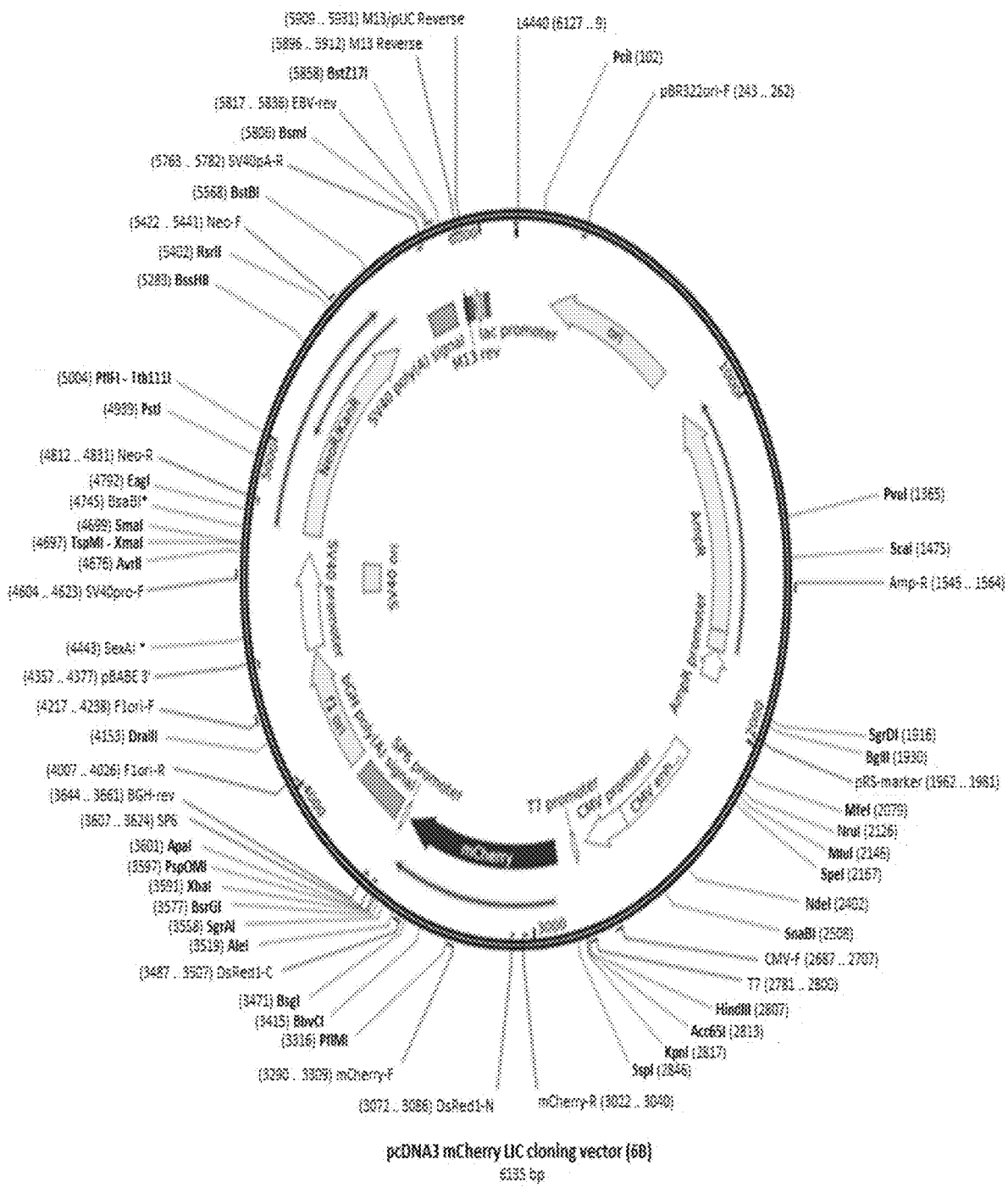

FIG. 18 shows a plasmid vector carrying mcherry gene, in accordance with an embodiment of the present disclosure.

Figure 19:
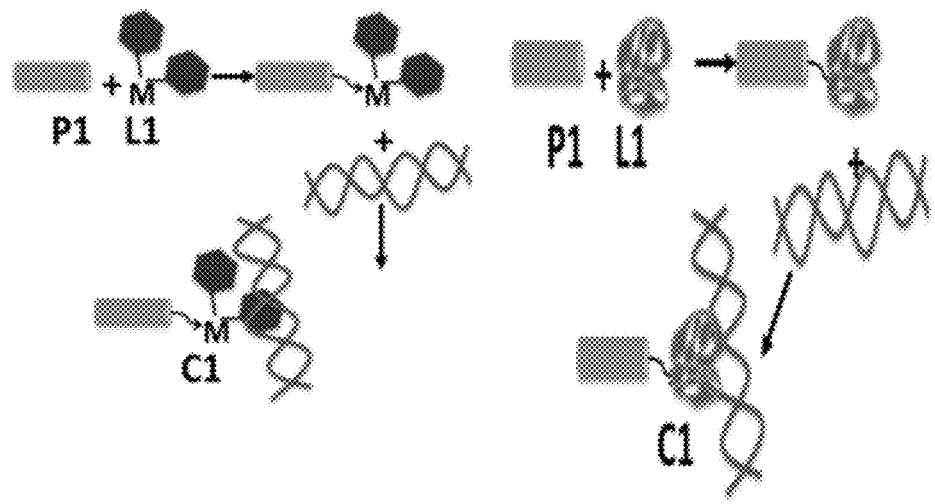

FIG. 19 shows a process for preparing a conjugate, in accordance with an embodiment of the present disclosure.

Figure 20:
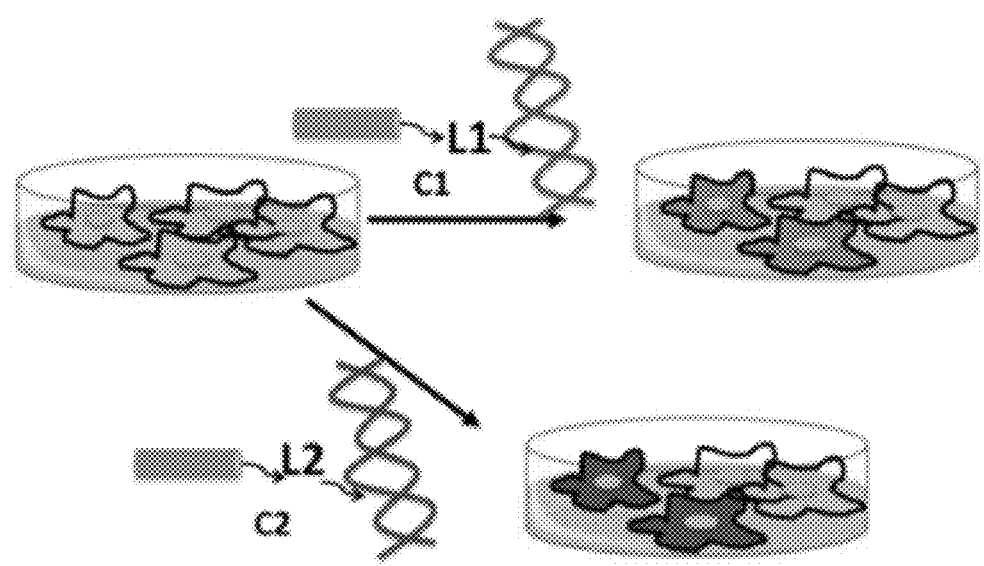

FIG. 20 shows a representation of transfection using a conjugate, in accordance with an embodiment of the present disclosure.

Figure 21:
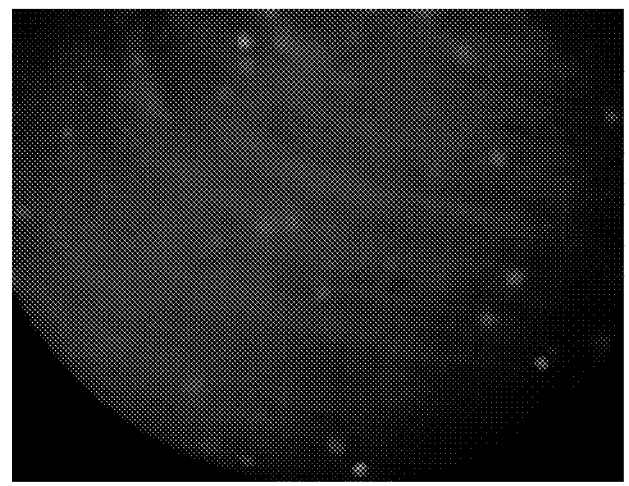

FIG. 21 shows confocal microscopy images of HeLa cells after transfection with a conjugate in accordance with the present invention; the conjugate comprising the mcherry gene coding for RFP (Red Fluorescent Protein) linked via copper [II] phenanthroline to the EfsQNR protein.

Figure 22:
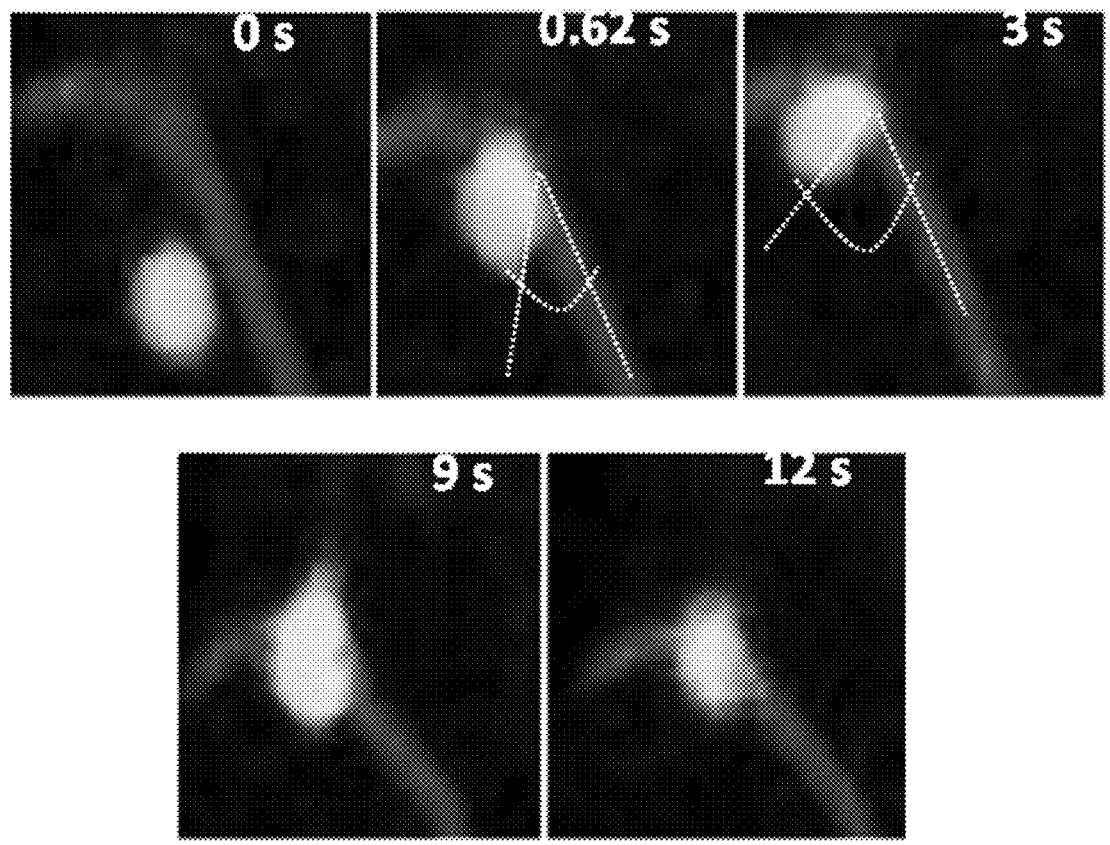

FIG. 22 shows real-time direct penetration of a cell membrane by an EfsQNR-ATTO 520 conjugate in accordance with the present invention.

Figure 23:
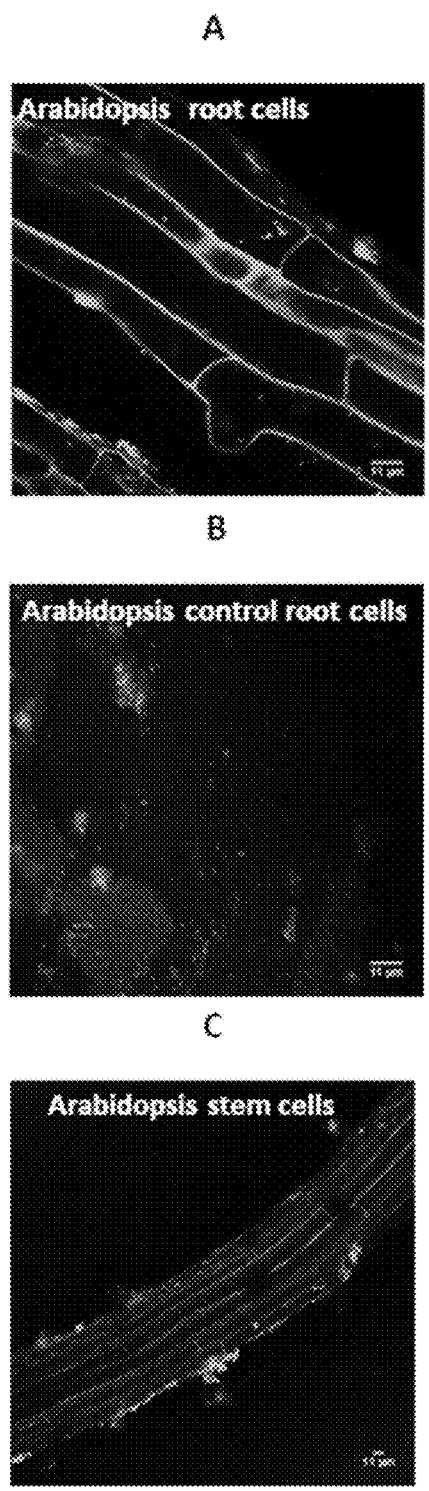

FIG. 23 shows labelling of plant *Arabidopsis* cells by CPP labelled with ATTO-520, in accordance with an embodiment of the present disclosure. Panel A shows labelling in *Arabidopsis* root cells; Panel B shows labelling in *Arabidopsis* control root cells; and Panel C shows labelling in *Arabidopsis* stem cells.

Figure 24:
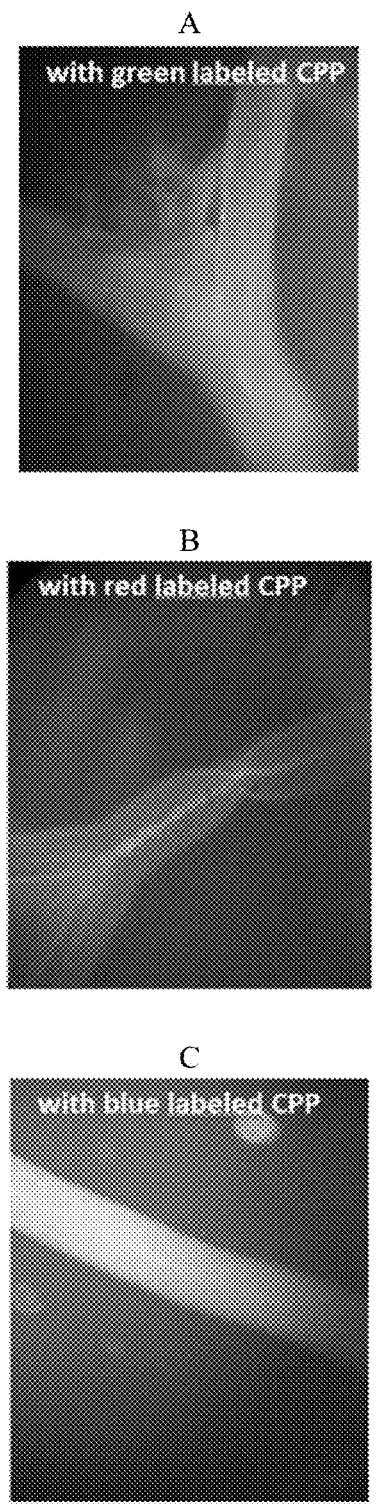

FIG. 24 shows labelling of plant *Arabidopsis* cells by A) CPP labelled with ATTO-520; B) CPP labelled with ATTO-594, and C) CPP labelled with ATTO-390, in accordance with an embodiment of the present disclosure.

Figure 25:
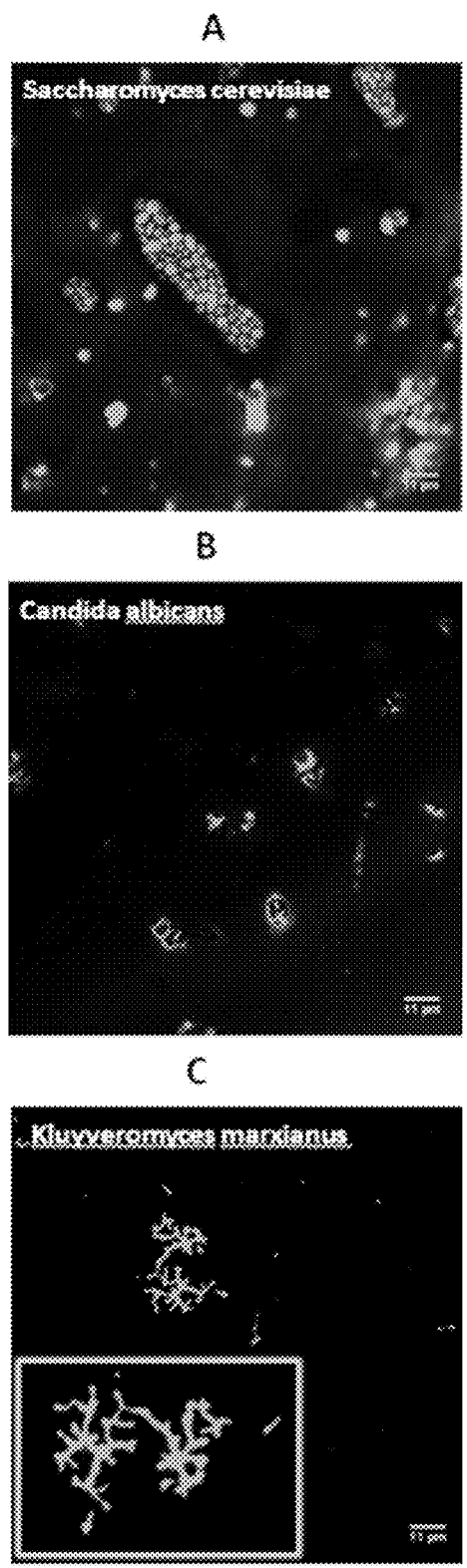

FIG. 25 shows labelling of yeast cells by CPP labelled with ATTO-520, in accordance with an embodiment of the present disclosure. Panel A shows fluorescence/confocal microscope images of *Saccharomyces cerevisiae* cells; Panel B shows fluorescence/confocal microscope images of *Candida albicans* cells; and Panel C shows fluorescence/confocal microscope images of *Kluyveromyces marxianus* cells.

Figure 26:
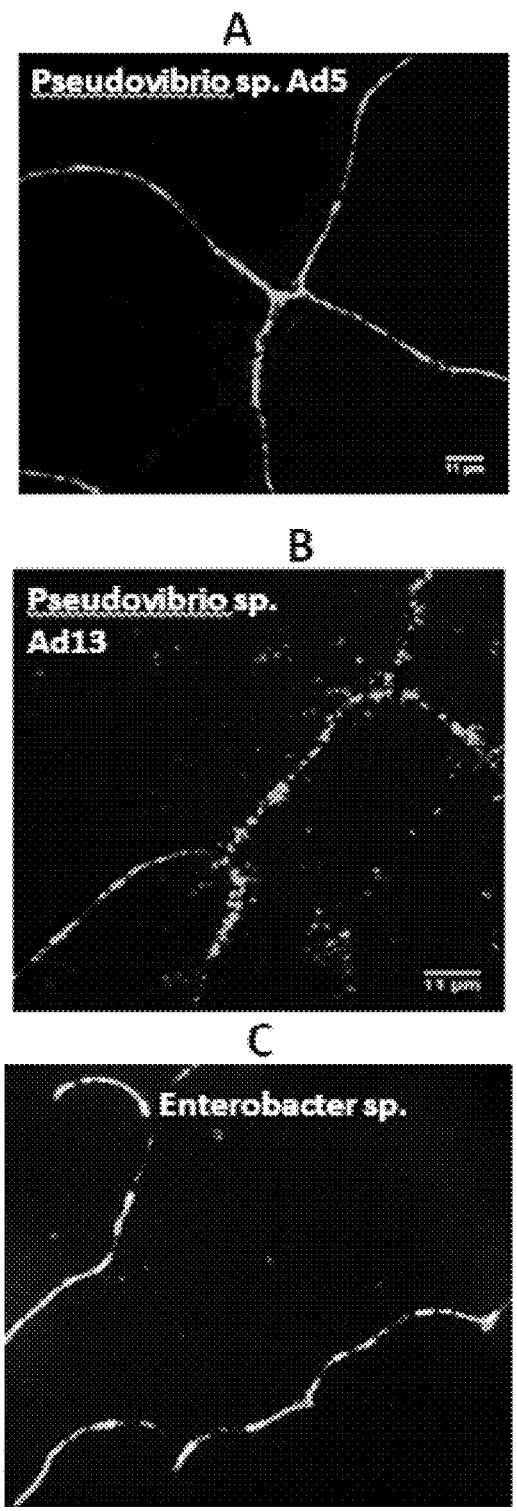
Figure 26:
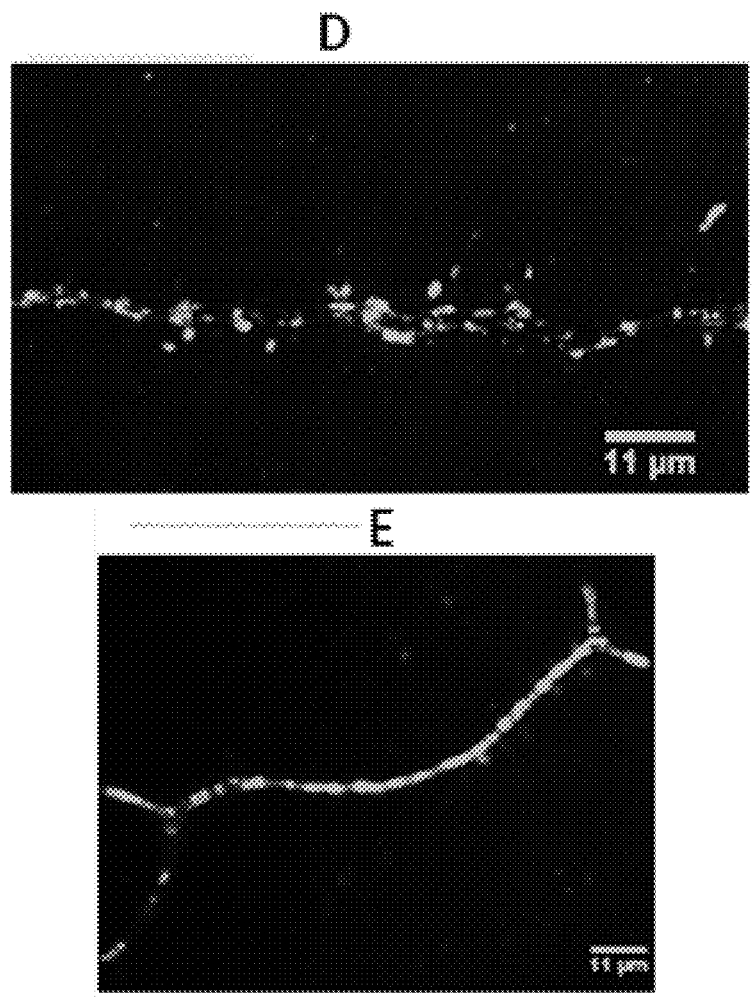

FIG. 26 shows labelling of bacterial cells by CPP labelled with ATTO-520, in accordance with an embodiment of the present disclosure. Panel A shows fluorescence/confocal microscope images of *Pseudovibrio* sp. Ad5 cells; Panel B shows fluorescence/confocal microscope images of *Pseudovibrio* sp. Ad13 cells; Panel C shows fluorescence/confocal microscope images of *Enterobacter* sp. Cells; Panel D and Panel E show magnified images.

Figure 27:
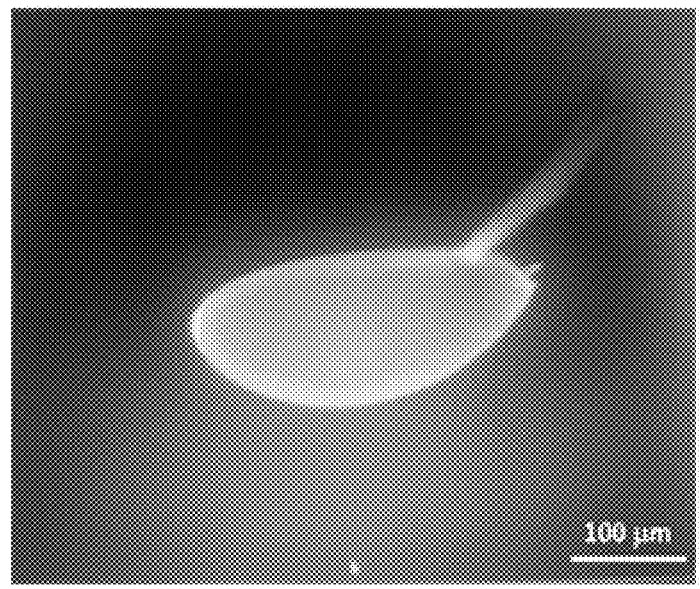

FIG. 27 shows labelling of *Drosophila* embryo cells by CPP labelled with ATTO-520, in accordance with an embodiment of the present disclosure.

Figure 28:
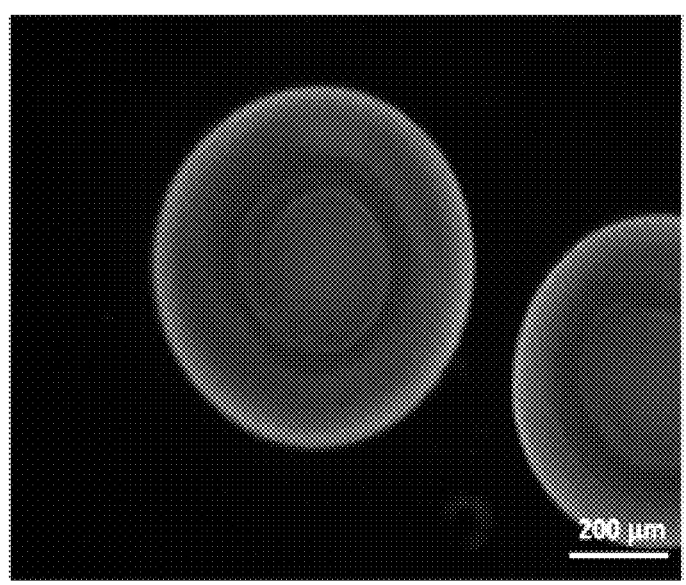

FIG. 28 shows labelling of Zebra fish embryo cells by CPP labelled with ATTO-520, in accordance with an embodiment of the present disclosure.

Figure 29:
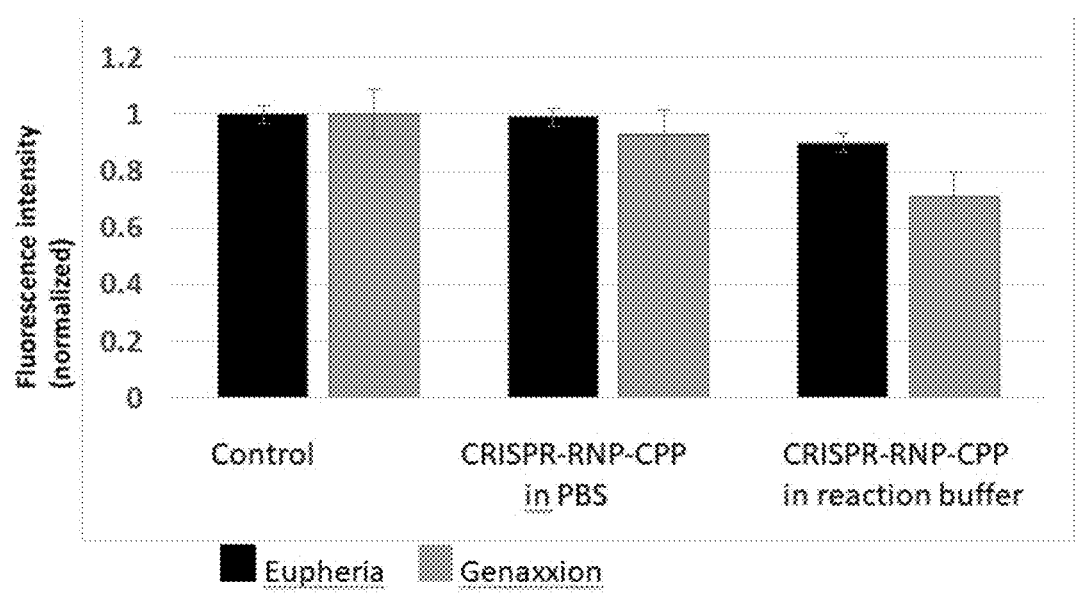

FIG. 29 shows results of gene editing of HEK293 cells expressing eGFP following CPP assisted delivery of CRISPR-Cas9 and eGFP specific gRNA as observed by the reduction in fluorescence intensity due to eGFP (as measured by fluorescence plate reader).

FIG. 30 shows the results for a transfection experiment in MCF7 cells using (A) the conjugate obtained in Example 1 (EfsQNR) (SEQ ID NO: 2) and a labelled circular plasmid DNA of 2.7 kb, commercially obtained from Mirus Bio (product code MIR 7904) and (B) control labelled plasmid as used above in the absence of the conjugate. (i) shows the maximum projection of the cells after incubation; (ii) shows image corresponding to the intensity plots of the cells after incubation; and (iii) shows the intensity plots of the cells after incubation.

Figure 31:
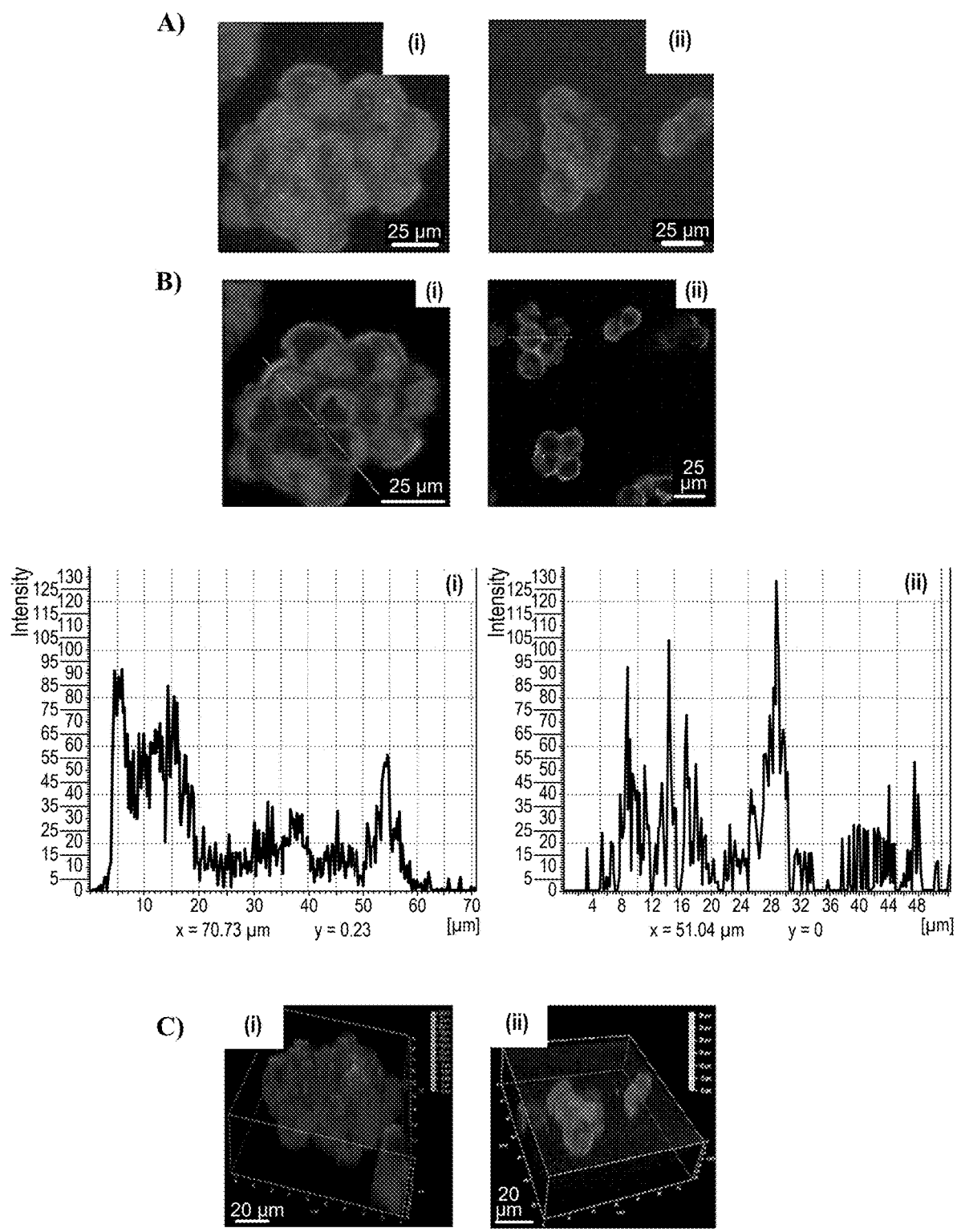

FIG. 31 shows results for a transfection experiment in MCF-7 cells using the conjugate obtained in Example 1 (EfsQNR) and the endonuclease Cas9, tagged with either (i) red fluorescent protein, or (ii) the fluorescent dye Atto520. (A) shows the maximum projection of the cells after incubation; (B) shows the intensity plots of the cells after incubation; and (C) shows 3D depth images of cells.

Figure 32:
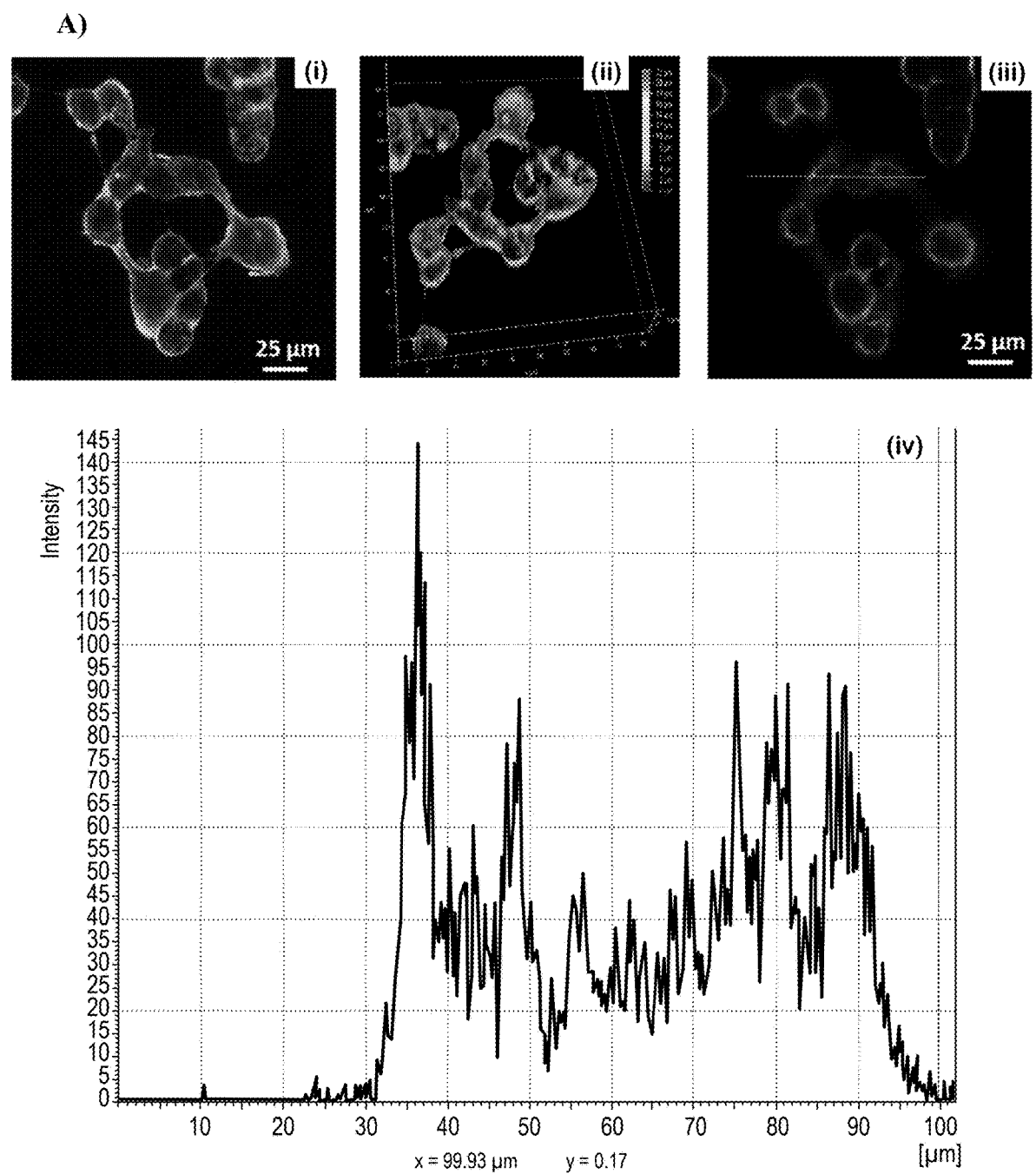
Figure 32:
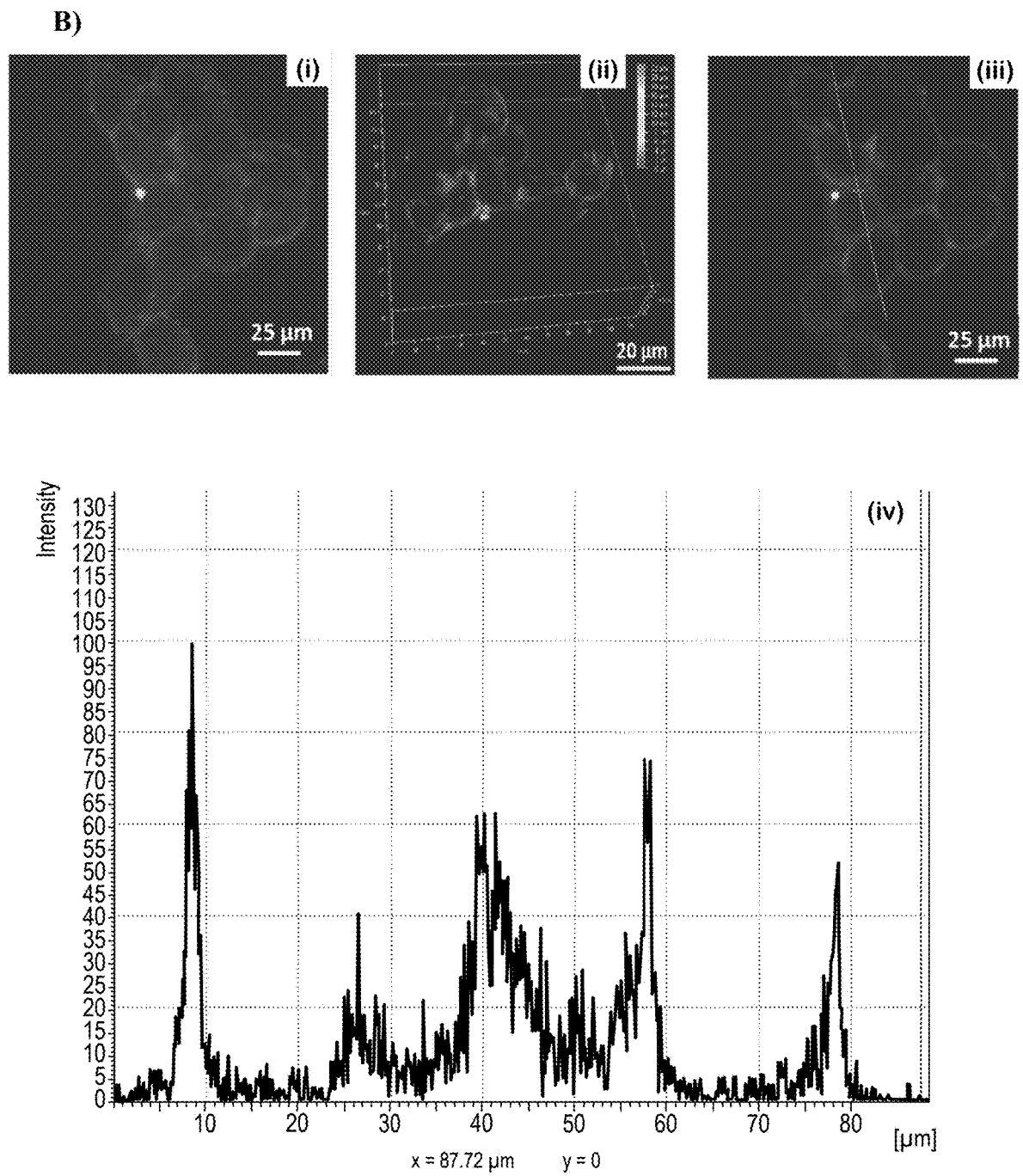

FIG. 32 shows results for a transfection experiment in MCF-7 cells using (A) the conjugate obtained in Example 1 (EfsQNR) and the gRNA tagged with the fluorescent dye MFP488; and (B) control gRNA tagged with the fluorescent dye MFP488. (i) shows the maximum projection of the cells after incubation; (ii) shows 3D depth images of cells; (iii) image corresponding to the intensity plots of the cells after incubation; and (iv) shows the intensity plots of the cells after incubation.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, NY; Ausubel, F. M. et al. (1995 and periodic supplements; Current Protocols in Molecular Biology, ch. 9, 13, and 16, John Wiley & Sons, New York, N. Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

The articles 'a', 'an' and 'the' are used to refer to one or to more than one (i.e. to at least one) of the grammatical object of the article.

As used herein, the term 'comprising' means any of the recited elements are necessarily included and other elements may optionally be included as well. 'Consisting essentially of' means any recited elements are necessarily included, elements which would materially affect the basic and novel characteristics of the listed elements are excluded, and other elements may optionally be included. 'Consisting of' means that all elements other than those listed are excluded. Embodiments defined by each of these terms are within the scope of this invention.

The term 'including' is used to mean 'including but not limited to'. 'Including' and 'including but not limited to' are used interchangeably.

As used herein, the term 'cell membrane' is a biological membrane which is present in both prokaryotic and eukaryotic cells and separates the inner and outer environment of a cell. It acts as a semi-permeable barrier which checks the transport of substances in and out of the cell and is typically formed of a phospholipid bilayer. The membrane acts as a support and helps in maintaining the shape and structure of a cell.

As used herein the term 'β helical protein' means a protein forming a β helical secondary structure. β helical proteins are formed from a generally parallel association between adjacent β strands of a peptide chain. A β helical protein can be a right-handed β helical or a left-handed β helical depending on the direction of coiling of the helix structure.

As used herein the term 'Pentapeptide-repeat protein (PRP)' means β helical proteins consisting of a tandemly repeated pentapeptide. In embodiments, the tandemly repeated pentapeptide has the consensus sequence $(STAV)_1(DN)_2(LF)_3(STR)_4(G)_5$. The PRP family has well over 500 members in the prokaryotic and eukaryotic kingdom.

As used herein the term 'functional molecule' is any molecule that has a utility within a cell. Examples of functional molecules suitable for use in the present invention include dyes, drug molecules, proteins, enzymes, antibodies, and nucleic acids.

As used herein the term 'cell penetrating peptide' or 'CPP' relates to peptides sequences that facilitate cellular intake/uptake of various functional molecules. Cell penetrating peptides generally deliver the functional molecule directly through the cell membrane avoiding the need for endocytosis mediated pathways for cellular entry.

As used herein the term 'P-cadherin' refers to a cell to cell adhesion molecule having a homeostatic function in normal tissues. The over expression of this molecule is associated with significant tumour promoting effects in the breast, ovarian, prostate, endometrial, skin, gastric, pancreas and colon neoplasms.

As used herein the term 'NHS-coumarin' or 'NHSC' refers to a fluorescent dye widely used in cell biology techniques. It is a common name for 7-(diethylamino) coumarin-3-carboxylic acid N-succinimidyl ester having a molecular weight of 358.35 g/mol. NHS-coumarin (NHSC) has an excitation wavelength of 445 nm and an emission wavelength at 482 nm. On observation under fluorescent microscopy, it emits green fluorescence indicating the location and quantification of the molecule conjugated along with this dye.

As used herein the term 'phosphatidyl choline' defines a class of phospholipids molecules that incorporate a choline as a headgroup. Phosphatidyl choline may be used as a signalling molecule that facilitates selective binding and attachment with cell membranes.

As used herein the term 'Hoechst 33342' refers to a solution of fluorescent dye that is used for both fixed and live cell staining of DNA and nuclei in cellular imaging techniques. Hoechst 33342 is a cell-permeable DNA stain having an excitation wavelength of 460 nm and an emission wavelength of 490 nm and it preferentially binds to adenine (A)-thymine(T) region of DNA.

As used herein the term 'ATTO 520' or 'A-520', 'ATTO 390' or 'A-390' and 'ATTO 647N' or 'A-647N' refer respectively to fluorescent dyes developed by the ATTO-Tec GmbH and commercially available from Sigma Aldrich.

As used herein the term 'Ruthenium metal complex' refers to the coordination complex of ruthenium metal which is known to possess anti-cancer activities. Octahedral ruthenium (III) and ruthenium (II) complexes display anti-neoplastic activities on many experimental tumours. Ruthenium metal complex is considered as an excellent alternative to circumvent the side-effects of platinum-based compounds. A non-limiting example of a ruthenium metal complex that has been demonstrated for use in the present invention is tricarbonyl dichloro ruthenium (II) (ex-Sigma Aldrich).

The term 'nucleic acid' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and are typically manufactured synthetically, but may also be isolated from natural sources. Nucleic acids may further include modified DNA or RNA, for example DNA or RNA that has been methylated or that has been subject to chemical modification, for example 5'-capping with 7-methylguanosine, 3'-processing such as cleavage and polyadenylation, and splicing, or labelling with fluorophores or other compounds. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Hence, where the terms 'DNA' and 'RNA' are used herein it should be understood that these terms are not limited to only include naturally occurring nucleotides. Sizes of nucleic acids, also referred to herein as 'polynucleotides' are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 100 nucleotides in length are typically called 'oligonucleotides'.

As used herein, the terms '3'' ('3 prime') and '5'' ('5 prime') take their usual meanings in the art, i.e. to distinguish the ends of polynucleotides. A polynucleotide has a 5' and a 3' end and polynucleotide sequences are conventionally written in a 5' to 3' direction.

The term 'amino acid' in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term 'amino acid' further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as 'functional equivalents' of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

A 'polypeptide' is a polymer of amino acid residues joined by peptide bonds, whether produced naturally or in vitro by synthetic means. Polypeptides of less than around 12 amino acid residues in length are typically referred to as 'peptides' and those between about 12 and about 30 amino acid residues in length may be referred to as 'oligopeptides'. The term 'polypeptide' as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term 'protein' is used herein to refer to a macromolecule comprising one or more polypeptide chains.

The term 'isolated', when applied to a polynucleotide or protein sequence, denotes that the sequence has been removed from its natural organism of origin and is, thus, free of extraneous or unwanted coding or regulatory sequences. The isolated sequence is suitable for use in assembly of compositions and nanostructures of the present invention. Such isolated sequences may include cDNAs and RNAs.

According to the present invention, homology to the nucleic acid or protein sequences described herein is not limited simply to 100% sequence identity. Any closely related nucleic acid or protein sequences to those specified herein that demonstrate functional and/or biochemical equivalence are considered within the scope of the present invention as defined by the claims.

The term 'signal sequence' in the context of the present invention means nuclear localizing sequence or recognition sequences for different cell organelles or nucleic acid binding domains such as zinc finger binding proteins.

As used herein the term 'carrier' means substances that serve as mechanisms to improve the delivery and the effectiveness of the drug.

As used herein the term 'diluent' (also referred to as filler, dilutant, or thinner) means a diluting agent.

As used herein the term 'excipient' refers to an inactive substance that serves as a vehicle or medium for a drug or other active substance. Excipients include colouring agents, humectants, preservatives, emollients and combinations thereof.

As used herein, the term 'RNA-guided endonuclease' is meant a polypeptide which endonuclease activity and specificity dependent on its association with at least one guide RNA molecule. An example of RNA-guided endonuclease is Cas9 as part of the Cas9/CRISPR system.

As used herein the term 'CRISPR' (clustered regularly interspaced short palindromic repeats) refers to a family of DNA sequences found within the genomes of prokaryotic organisms such as bacteria. The term may be used to refer to the techniques of gene editing that relies on the use of CRISPR associated proteins, for example Cas-9 (CRISPR-associated protein 9) that can associate with and then use CRISPR sequences as a guide to recognise and cleave specific strands of DNA that are complimentary to the CRISPR sequence. Cas9 nucleases together with CRISPR sequences form the basis of the CRISPR-Cas9 gene editing technique.

As used herein, the term 'Cas9' refers to the Cas9 endonuclease protein. Also named Csn1 (COG3513) Cas9 is a large protein that participates in both crRNA biogenesis and in the destruction of invading DNA. The term 'Cas9' is also meant to encompass an engineered endonuclease or a homologue of Cas9 which is capable of processing target nucleic acid sequence. Cas9 can induce a cleavage in the nucleic acid target sequence which can correspond to either a double-stranded break or a single-stranded break. The term Cas9 is intended to include variants that can be a Cas9 endonuclease that does not naturally exist in nature and that is obtained by protein engineering or by random mutagenesis provided such Cas9 variants remain functional, i.e. they retain the capacity of processing a target nucleic acid sequence.

As used herein the term 'CRISPR-RNP' relates to a CRISPR ribonucleotide comprising a CRISPR endonuclease protein and one or more guide RNAs. The term 'CRISPR-RNP-CPP' use herein relates to conjugate of a CRISPR-RNP complex with a cell penetrating peptide of an embodiment of the present invention.

As used herein, the term 'guide RNA' or 'gRNA' refers to an RNA polynucleotide sequence comprising a guide sequence. In use, guide RNAs can be associated with an endonuclease that acts to cut a double stranded DNA at a site determined by the gRNA. The term 'guide sequence' refers to a sequence preferably longer than 8 nucleic acid bases, more preferably longer than 10 nucleic acid bases, even more preferably longer than 12 nucleic acid bases, has the ability to specify a target sequence in the genome. In general, this RNA molecule has the ability to hybridize said target sequence and to mediate the endonuclease activity of said endonuclease.

As used herein the term 'wild type' refers to the typical or naturally-occurring form of an organism, strain, gene or characteristic as distinguished from 'mutant' or 'variant' forms.

As used herein, the term 'non-naturally occurring' or 'engineered' are used interchangeably. The terms, when referring to nucleic acid molecules or polypeptides, mean that the nucleic acid molecule or the polypeptide differs from that found in nature and/or is at least substantially free from at least one other component with which they are naturally associated in nature.

As used herein, the term 'complementarity' refers to the ability of a nucleic acid to associate with, for example a non-covalent interaction via hydrogen bond(s), with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary).

As used herein, the term 'expression' refers to the process by which a polynucleotide is transcribed from a DNA template (such as into and mRNA or other RNA transcript) and/or the process by which a transcribed mRNA is subsequently translated into peptides, polypeptides, or proteins.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

Sequences

SEQ ID NO: 1 depicts amino acid sequence of AlbG protein.

MPAKTLESKDYCGESFVSEDRSGQSLESIRFEDCTFRQCNFTEAELNRC

KFRECEFVDCNLSLISIPQTSFMEVRFVDCKMLGVNWTSAQWPSVKMEG

ALSFERCILNDSLFYGLYLAGVKMVECRIHDANFTEADCEDADFTQSDL

KGSTFHNTKLTGASFIDAVNYHIDIFHNDIKRARFSLPEAASLLNSLDI

ELSD

SEQ ID NO: 2 depicts amino acid sequence of EfsQNR protein.

GSHMKITYPLPPNLPEQLPLLTNCQLEDEAILENHLYQQIDLPNQEVRN

LVFRDAVFDHLSLANGQFASFDCSNVRFEACDFSNVEWLSGSFHRVTFL

RCNLTGTNFADSYLKDCLFEDCKADYASFRFANFNLVHFNQTRLVESEF

FEVTWKKLLLEACDLTESNWLNTSLKGLDFSQNTFERLTFSPNYLSGLK

VTPEQAIYLASALGLVIT

SEQ ID NO: 3 depicts amino acid sequence of anti-freeze protein from *Tenebrio molitor*.

QCTGGADCTSCTGACTGCGNCPNAVTCTNSQHCVKANTCTGSTDCNTAQ

TCTNSKDCFEANTCTDSTNCYKATACTNSSGCPGH

SEQ ID NO: 4 depicts amino acid sequence of anti-freeze protein from *Rhagium inquisitor*.

GYSCRAVGVDGRAVTDIQGTCHAKATGAGAMASGTSEPGSTSTATATGRG
ATARSTSTGRGTATTTATGTASATSNAIGQGTATTTATGSAGGRATGSAT
TSSSASQPTQTQTITGPGFQTAKSFARNTATTTVTASHHHHHH

SEQ ID NO: 5 depicts amino acid sequence of anti-freeze protein from Spruce Budworm (*Choristoneura fumiferana*).

DGSCTNTNSQLSANSKCEKSTLTNCYVDKSEVYGTTCTGSRFDGVTITTS
TSTGSRISGPGCKISTCIITGGVPAPSAACKISGCTFSAN

SEQ ID NO: 6 depicts amino acid sequence of QNRB1 protein.

GSHMALALVGEKIDRNRFTGEKIENSTFFNCDFSGADLSGTEFIGCQFYD
RESQKGCNFSRAMLKDAIFKSCDLSMADFRNSSALGIEIRHCRAQGADFR
GASFMNMITTRTWFCSAYITNTNLSYANFSKVVLEKCELWENRWIGAQVL
GATFSGSDLSGGEFSTFDWRAANFTHCDLTNSELGDLDIRGVDLQGVKLD
NYQASLLMERLGIAVIG

SEQ ID NO: 7 depicts amino acid sequence of UDP-N-acetylglucosamine acyltransferase protein.

MIDKSAFVHPTAIVEEGASIGANAHIGPFCIVGPHVEIGEGTVLKSHVVV
NGHTKIGRDNEIYQFASIGEVNQDLKYAGEPTRVEIGDRNRIRESVTIHR
GTVQGGGLTKVGSDNLLMINAHIAHDCTVGNRCILANNATLAGHVSVDDF
AIIGGMTAVHQFCIIGAHVMVGGCSGVAQDVPPYVIAQGNHATPFGVNIE
GLKRRGFSREAITAIRNAYKLIYRSGKTLDEVKPEIAELA ETYPEVKAF
TDFFARSTRGLIR

SEQ ID NO: 8 depicts amino acid sequence of NP275 protein from *Nostoc punctiforme*.

MGSSHHHHHHSSGLVPRGSHMDVEKLRQLYAAGERDFSIVDLRGAVLENI
NLSGAILHGAMLDEANLQQANLSRADLSGATLNGADLRGANLSKADLSDA
ILDNAILEGAILDEAVLNQANLKAANLEQAILSHANIREADLSEANLEAA
DLSGADLAIADLHQANLHQAALERANLTGANLEDANLEGTILEGGNNNLA
T

SEQ ID NO: 9 depicts amino acid sequence of pectate lyase C.

ATDTGGYAATAGGNVTGAVSKTATSMQDIVNIIDAARLDANGKKVKGGAY
PLVITYTGNEDSLINAAAANICGQWSKDPRGVEIKEFTKGITIIGANGSS
ANFGIWIKKSSDVVVQNMRIGYLPGGAKDGDMIRVDDSPNVWVDHNELFA
ANHECDGTPDNDTTFESAVDIKGASNTVTVSYNYIHGVKKVGLDGSSSSD
TGRNITYHHNYYNDVNARLPLQRGGLVHAYNNLYTNITGSGLNVRQNGQA
LIENNWFEKAINPVTSRYDGKNFGTWVLKGNNITKPADFSTYSITWTADT
KPYVNADSWTSTGTFPTVAYNYSPVSAQCVKDKLPGYAGVGKNLATLTST
ACK

SEQ ID NO: 10 depicts amino acid sequence of pectate lyase from *Caldicellulosiruptor bescii*

VGTNTGGVLVITDTIIVKSGQTYDGKGIKIIAQGMGDGSQSENQKPIFKL
EKGANLKNVIIGAPGCDGIHCYGDNVVENVVWEDVGEDALTVKSEGVVEV
IGGSAKEAADKVFQLNAPCTFKVKNFTATNIGKLVRQNGNTTFKVVIYLE
DVTLNNVKSCVAKSDSPVSELWYHNLNVNNCKTLFEFPSQSQIHQY

SEQ ID NO: 11 depicts amino acid sequence of carbonic anhydrase from *Methanosarcina thermophila*.

QEITVDEFSNIRENPVTPWNPEPSAPVIDPTAYIDPQASVIGEVTIGANV
MVSPMASIRSDEGMPIFVGDRSNVQDGVVLHALETINEEGEPIEDNIVEV
DGKEYAVYIGNNVSLAHQSQVHGPAAVGDDTFIGMQAFVFPKSKVGNNCVL
EPRSAAIGVTIPDGRYIPAGMVVTSQAEADKLPEVTDDYAYSHTNEAVVY
VNVHLAEGYKETS

SEQ ID NO: 12 depicts amino acid sequence of Pectin lyase A protein from *Aspergillus niger*.

VGVSGSAEGFAKGVTGGGSATPVYPDTIDELVSYLGDDEARVIVLTKTFD
FTDSEGTTTGTGCAPWGTASACQVAIDQDDWCENYEPDAPSVSVEYYNAG
TLGITVTSNKSLIGEGSSGAIKGKGLRIVSGAENIIQNIAVTDINPKYV
WGGDAITLDDCDLVWIDHVTTARIGRQHYVLGTSADNRVSLTNNYIDGVS
DYSATCDGYHYWAIYLDGDADLVTMKGNYIYHTSGRSPKVQDNTLLHAVN
NYWYDISGHAFEIGEGGYVLAEGNVFQNVDTVLETYEGEAFTVPSSTAGE
VCSTYLGRDCVINGFGSSGTFSEDSTSFLSDFEGKNIASASAYTSVASRV
VANAGQGNL

SEQ ID NO: 13 depicts amino acid sequence of TtCuA protein.

AYTLATHTAGVIPAGKLERVDPTTVRQEGPWADPAQAVVQTGPNQYTVYV
LAFAFGYQPNPIEVPQGAEIVFKITSPDVIHGFHVEGTNINVEVLPGEVS
TVRYTFKRPGEYRIICNQYCGLGHQNMFGTIVVKE

SEQ ID NO: 14 depicts a signal sequence for targeting the nucleus of the cell.

PAAKRVKCD

SEQ ID NO: 15 depicts a signal sequence for targeting the endoplasmic reticulum of the cell.

YPYDVPDYAKDEL

SEQ ID NO: 16 depicts a signal sequence for targeting the mitochondria of the cell.

MLSLRQSIRFFKPATRTLCSSRYLL

SEQ ID NO: 17 depicts a signal sequence for targeting the P-cadherin-over expressing breast cancer cells.

LSTAADMQGVVTDGMASGLDKDYLKPDD

SEQ ID NO: 18 depicts a consensus sequence in a pentapeptide-repeat protein. $(STAV)_1(DN)_2(LF)_3(STR)_4(G)_5$ SEQ ID NO: 19 depicts a nucleic acid sequence of AlbG gene.

ATGCCGGCGAAAACCCTGGAAAGCAAAGATTATTGCGGCGAAAGCTTTGT

GAGCGAAGATCGCAGCGGCCAGAGCCTGGAAAGCATTCGCTTTGAAGATT

GCACCTTTCGCCAGTGCAACTTTACCGAAGCGGAACTGAACCGCTGCAAA

TTTCGCGAATGCGAATTTGTGGATTGCAACCTGAGCCTGATTAGCATTCC

GCAGACCAGCTTTATGGAAGTGCGCTTTGTGGATTGCAAAATGCTGGGCG

TGAACTGGACCAGCGCGCAGGCGGGCGCGCTGAGCTTTGAACGCTGCATT

CTGAACGATAGCCTGTTTTATGGCCTGTATCTGGCGGGCGTGAAAATGGT

GGAATGCCGCATTCATGATGCGAACTTTACCGAAGCGGATTGCGAAGATG

CGGATTTTACCCAGAGCGATCTGAAAGGCAGCACCTTTCATAACACCAAA

CTGACCGGCGCGAGCTTTATTGATGCGGTGAACTATCATATTGATATTTT

TCATAACGATATTAAACGCGCGCTTTAGCCTGCCGGAAGCGGCGAGCC

TGCTGAACAGCCTGGATATTGAACTGAGCGAT

SEQ ID NO: 20 depicts a nucleic acid sequence of EfsONR gene.

GGCAGCCATATGAAAATTACCTATCCGCTGCCGCCGAACCTGCCGGAAC

AGCTGCCGCTGCTGACCAACTGCCAGCTGGAAGATGAAGCGATTCTGGA

AAACCATCTGTATCAGCAGATTGATCTGCCGAACCAGGAAGTGCGCAAC

CTGGTGTTTCGCGATGCGGTGTTTGATCATCTGAGCCTGGCGAACGGCC

AGTTTGCGAGCTTTGATTGCAGCAACGTGCGCTTTGAAGCGTGCGATTT

TAGCAACGTGGAATGGCTGAGCGGCAGCTTTCATCGCGTGACCTTTCTG

CGCTGCAACCTGACCGGCACCAACTTTGCGGATAGCTATCTGAAAGATT

GCCTGTTTGAAGATTGCAAAGCGGATTATGCGAGCTTTCGCTTTGCGAA

CTTTAACCTGGTGCATTTTAACCAGACCCGCCTGGTGGAAAGCGAATTT

TTTGAAGTGACCTGGAAAAAACTGCTGCTGGAAGCGTGCGATCTGACCG

AAAGCAACTGGCTGAACACCAGCCTGAAAGGCCTGGATTTTAGCCAGAA

CACCTTTGAACGCCTGACCTTTAGCCCGAACTATCTGAGCGGCCTGAAA

GTGACCCCGGAACAGGCGATTTATCTGGCGAGCGCGCTGGGCCTGGTGA

TTACC

SEQ ID NO: 21 depicts a nucleic acid sequence of TtCuA gene

GCGTATACCCTGGCGACCCATACCGCGGGCGTGATTCCGGCGGGCAAAC

TGGAACGCGTGGATCCGACCACCGTGCGCCAGGAAGGCCCGTGGGCGGA

TCCGGCGCAGGCGGTGGTGCAGACCGGCCCGAACCAGTATACCGTGTAT

GTGCTGGCGTTTGCGTTTGGCTATCAGCCGAACCCGATTGAAGTGCCGC

AGGGCGCGGAAATTGTGTTTAAAATTACCAGCCCGGATGTGATTCATGG

CTTTCATGTGGAAGGCACCAACATTAACGTGGAAGTGCTGCCGGGCGAA

GTGAGCACCGTGCGCTATACCTTTAAACGCCCGGGCGAATATCGCATTA

TTTGCAACCAGTATTGCGGCCTGGGCCATCAGAACATGTTTGGCACCAT

TGTGGTGAAAGAA

SEQ ID NO: 22 depicts a signal sequence for targeting to actin in the cell.

GDVQKKRWLFETKPLD

SEQ ID NO: 23 depicts a signal sequence for targeting to tubulin in the cells.

VQSKCGSKDNIKHVPGGG

SEQ ID NO. 24: depicts an amino acid sequence of a zinc finger protein

MERPYACPVESCDRRFSDSSNLTRHIRIHTGQKPFQCRICMRNFSRSDH

LTTHIRTHTGEKPFACDICGRKFARSDERKRHTKIHLRQKD

SEQ ID NO. 25: depicts a nucleic acid sequence of mcherry gene.

GTGAGCAAGGGCGAGGAGGATAACATGGCCATCATCAAGGAGTTCATGC

GCTTCAAGGTGCACATGGAGGGCTCCGTGAACGGCCACGAGTTCGAGAT

CGAGGGCGAGGGCGAGGGCCGCCCCTACGAGGGCACCCAGACCGCCAAG

CTGAAGGTGACCAAGGGTGGCCCCCTGCCCTTCGCCTGGGACATCCTGT

CCCCTCAGTTCATGTACGGCTCCAAGGCCTACGTGAAGCACCCCGCCGA

CATCCCCGACTACTTGAAGCTGTCCTTCCCCGAGGGCTTCAAGTGGGAG

CGCGTGATGAACTTCGAGGACGGCGGCGTGGTGACCGTGACCCAGGACT

CCTCCCTCCAGGACGGCGAGTTCATCTACAAGGTGAAGCTGCGCGGCAC

CAACTTCCCCTCCGACGGCCCCGTAATGCAGAAGAAGACCATGGGCTGG

GAGGCCTCCTCCGAGCGGATGTACCCCGAGGACGGCGCCCTGAAGGGCG

AGATCAAGCAGAGGCTGAAGCTGAAGGACGGCGGCCACTACGACGCTGA

GGTCAAGACCACCTACAAGGCCAAGAAGCCCGTGCAGCTGCCCGGCGCC

TACAACGTCAACATCAAGTTGGACATCACCTCCCACAACGAGGACTACA

CCATCGTGGAACAGTACGAACGCGCCGAGGGCCGCCACTCCACCGGCGG

CATGGACGAGCTGTACAAGTAGTAATCTAGAGGGCCCTATTCTATAGTG

TCACC.

SEQ ID NO. 26: depicts a nucleic acid sequence of a primer for PCR amplification of the AlbG gene.

ATCCCGCTCATATGCCGGCCAAGACCCTTG

SEQ ID NO. 27: depicts a nucleic acid sequence of a primer for PCR amplification of the AlbG gene.

ATCCCGCTCTCGAGTCAATCGGACAGCTCGATATC

SEQ ID NO. 28: depicts a nucleic acid sequence of a primer for PCR amplification of the EfsQNR gene.

ATCCCGCTCATATGAAAATAACTTATCCCTTGCCA

SEQ ID NO. 29: depicts a nucleic acid sequence of a primer for PCR amplification of the EfsQNR gene.

ATCCCGCTCTCGAGTTAGGTAATCACCAAACCAAGT

The present invention also provides for conjugates comprising a recombinant protein and a functional molecule for penetrating cellular membranes, and uses thereof that have substantially similar sequence identity or homology to that of SEQ ID NOs: 1 to 12. The term 'substantially similar sequence identity' is used herein to denote a level of sequence similarity of from about 50%, 60%, 70%, 80%, 90%, 95% to about 99% identity. Percent sequence identity can be determined using conventional methods, for example those described in Henikoff and Henikoff Proc. Natl. Acad. Sci. USA 1992; 89:10915, and Altschul et al. Nucleic Acids Res. 1997; 25:3389-3402 for nucleic acids; and for proteins via comparison after alignment using systems such as BLAST®

Cell Penetrating Conjugate with Functional Molecules

Identifying novel drugs to cure or prevent life threatening diseases remains a highly active area of research. Most of such drugs tend to have targets inside the cells and to reach the target they would have to cross the semi permeable membrane which is not straightforward or efficient in many cases. Therefore, developing novel mechanisms to penetrate the cell membrane remains desirable. On the other hand, scientific investigations and studies aiming to unravel various cellular mechanisms are also seeking to find novel methods of penetrating cell membranes which can help in the labelling of the cell and its various organelles. Also, it would be highly useful in delivering the required materials inside cells for scientific experiments. Most of the cell penetrating molecules described in recent reports involve the endocytosis mechanism of cell entry.

To circumvent the disadvantages of the intake of molecules through endocytosis, for example the entrapment and degradation of drugs in different types of endosomal compartments which eventually fuse with degradative compartment of cells such as lysosomes, a cell membrane penetrating conjugate is disclosed herein which can penetrate the cell membrane to gain access to the inside the cells and can also be used to deliver various cargos including dyes, drugs, proteins, enzymes, antibodies, and nucleic acids inside the cells.

The present disclosure is not to be limited in scope by the specific embodiments described herein, which are intended for the purposes of exemplification only. Functionally-equivalent products, compositions, and methods are clearly within the scope of the disclosure, as described herein.

The present invention discloses a conjugate capable of penetrating a cell membrane. The conjugate comprises a recombinant β helical protein, or a recombinant β helical protein portion, linked to a functional molecule wherein the protein has a longest dimension, defined as its length, in the range of 5 nm-25 nm and a width or diameter, defined as the dimension of the protein structure substantially perpendicular to its length, in the range of 1 nm-5 nm. The dimension of the protein in defined as measured in the solid state (characterized by x-ray crystallography or atomic force microscopy) or in solution state (dynamic light scattering measurements).

In embodiments of the present invention, the protein structure of the conjugate may have a longest dimension or length greater than 5 nm, 7.5 nm, 10 nm, 11 nm, 12 nm, 13 nm or 14 nm. In embodiments, the protein structure of the conjugate may have a longest dimension or length less than 25 nm, 20 nm, 17.5 nm, 15 nm, 14 nm, 13 nm, 12 nm or 11 nm. Suitably the length is in the range of from 5 nm to 25 nm, more suitably from 10 nm to 15 nm, even more suitably from 11 nm to 14 nm or 12 nm to 13 nm. In embodiments, the protein structure of the conjugate may have a width or diameter, in a dimension substantially perpendicular to its length, of at least 1 nm, 1.1 nm, 1.2 nm, 1.3 nm, 1.4 nm, 1.5 nm, 1.6 nm, 1.7 nm, 1.8 nm, 1.9 nm or 2.0 nm. In embodiments, the protein structure of the conjugate may have a longest dimension or length less than 5.0 mm, 4.5 nm, 4.0 nm, 3.5 nm, 3.0 nm, 2.9 nm, 2.8 nm, 2.7 nm, 2.6 nm, 2.5 nm, 2.4 nm, 2.3 nm, 2.2 nm, 2.1 nm or 2.0 nm. Suitably the width is in the range of from 1 nm to 5 nm, more suitably from 1 nm to 3 nm, even more suitably from 1.5 nm to 2.5 nm. In an embodiment, the protein structure of the conjugate of the present invention may have tip shape that is generally quadrangular (four sides) in cross-section along a longitudinal axis. Suitably, the shape is rectangular. Suitably it is the tip or end of the protein structure that is quadrangular. The tip may be generally rectangular, i.e. not have precise right angled corners or the corners may be somewhat rounded. Suitably, the tip has a length in the range of from 5 nm to 25 nm, and a width in the range of from 1 nm to 5 nm. In embodiments, the tip may have dimensions as defined for the protein conjugate above.

A surrogate for or an alternative definition for the physical size of the protein portion of the conjugate of the present invention is the combination of its β-helical structure along with its molecular weight. The definition of the size of the protein based on its physical dimensions or on its molecular weight may be used interchangeably. In embodiments of the present invention, the molecular weight of the protein portion may be at least 30 kDa. Suitably, the molecular weight of the protein portion may be at least 35 kDa, 40 kDa, 45 kDa or 50 kDa. In embodiments of the present invention, the molecular weight of the protein portion may be at most 100 kDa. Suitably, the molecular weight of the protein portion may be at most 90 kDa, 80 kDa, 70 kDa, 60 kDa, 55 kDa or 50 kDa. Suitably the molecular weight range of the protein portion of the conjugate of the present invention is in the range of 30-100 kDa, more suitably, 40-60 kDa, even more suitably 48-55 kDa.

Without wishing to be bound by theory, it is envisaged that the beneficial properties in cell penetration demonstrated by the conjugates of the present invention is due to the physical size of the protein portion, as defined by the dimensions or molecular weight outlined above. A further feature of the proteins is the rigidity that derives largely from the uncommon β-helical secondary structure. Suitably the protein may be more rigid than the membrane to be penetrated. Typical cell membranes have a rigidity of 0.005 to 0.02 N/m² (as measured by Atomic Force Microscopy; Hayashi, "Tensile Properties and Local Stiffness of Cells"; Mechanics of Biological Tissue, pp 137-152) depending on cell type. Suitably the proteins of the present invention have a rigidity, or high stiffness parameter (K) typical of a β-helix of 0.7 to 12 N/m² (Keten et al., Cell Mol. Bioeng. 2009; 2; 66-74, which is incorporated herein by reference).

A further feature thought to be influential in the efficiency of cell penetration of the conjugates of the present invention is the charge profile and arrangement of the amino acids in the β-helical structure of the protein. Specifically, the presence of charged lysine, arginine asparagine, aspartic acid and/or glutamic acid 'ladders' in the β-helical protein structure facilitates penetration of the cell membrane, and the total negative charge of the protein sequence.

The term 'ladder' in respect of amino acid residues in β-helical protein structures is defined as a presence of alternatively arranged positively (lysine, arginine and/or asparagine) and negatively charged residues (aspartic acid and/or glutamic acid) along the length of the surface of the protein.

Without wishing to be bound by theory, the presence of charged 'ladder' structures in the β-helical structure of the protein according to the present invention could be facilitating the interaction of the protein with the lipid molecules of the cell membrane (e.g. in forming hydrogen bond with the hydroxyl groups of the lipid molecules) and/or first attachment of the protein onto the negatively charged cell membrane.

The total negative charge of the protein according to the present invention due to the negatively charged residues could be facilitating the repulsion leading to angular motion of the protein to make it stand straight on the membrane and puncture the membrane.

In embodiments of the present invention, the protein of the conjugate comprises ladders of alternately arranged surface exposed positively and negatively charged amino acid residues. In embodiments, the protein comprises at least one of an arginine ladder (10-30 Arg residues), a lysine ladder (10-30 Lys residues), an asparagine ladder (10-40 Asn residues), aspartic acid (10-40 Asp residues) and glutamic acid (10-40 Glu residues).

In embodiments of the present invention, the total formal charge of the protein may be zero, or it may be non-zero. Suitably the total formal charge is non-zero, more suitably the total formal charge is below zero (negative). In embodiments the total formal charge of the protein is below (i.e. more negative than) −10. Suitably, the total formal charge of the protein is below −20, −25, −30, −35, −40, −45 or −50. More suitably the total form charge is below −20. In embodiments the total formal charge of the protein is above (i.e. less negative than) −80. Suitably, the total formal charge of the protein is above −70, −65, −60, −55, −50, −45, −40, −35, or −30. More suitably, the total formal charge is above −60. In embodiments, the total formal charge of the protein is in the range of from −10 to −80, more suitably from −20 to −60.

The efficiency of cell penetration and the mechanism of cell penetration may be modulated by optimizing the total formal charge of the conjugates by increasing the number of positively charged residues (e.g. arginine) along the surface of the protein and the sequences can be mutated at the N terminal with the signalling sequences (SEQ ID NOs: 14, 15, 16 or 17 and/or phosphatidyl choline) for attaining specificity of cellular organelles or specificity of particular cancer cells.

In an embodiment, the protein of the conjugate of the present invention suitable for direct cell penetration (i.e. non-endocytotic) may have one or more of the following structural parameters:

Beta helical structure with stiffness parameter K (beta helix) 0.2 to 12 N/m²;
Length between 5 nm to 25 nm;
Diameter between 1 nm to 5 nm;
Molecular weight between 25 KDa to 100 KDa;
Alternatively arranged ladders of surface exposed positive and negative charge residues on the surface of the protein along the length: an arginine ladder (10-30 Arg residues), a lysine ladder (10-30 Lys residues), an asparagine ladder (10-40 Asn residues), aspartic acid (10-40 Asp residues) and glutamic acid (10-40 Glu residues);
Total formal charge (−20 to −60).

In embodiments of the present invention, the linker between the β-helical protein and the functional molecule may be formed by a direct link between the β-helical protein and the functional molecule, for example via an amide (or peptidic), or ester covalent linkage, or via metal coordination; or the linker may take the form of a linker molecule. Suitably the link is by covalent or non-covalent bonds or interactions. When the linker is a linker molecule the linker molecule may take any suitable form that reversibly connects the β-helical protein and the functional molecule. In some embodiments, the linker molecule may be selected from the group consisting of a peptide or protein, PEG (polyethylene glycol) linker, organic molecule, metal conjugate, drug-metal conjugate, nucleic acid binding domains, and nucleic acid intercalating molecule.

In an embodiment, the present invention discloses a conjugate having a recombinant β helical protein of length in the range of 5 nm-25 nm, suitably, 10 nm-15 nm and width is in the range of 1 nm-5 nm, suitably 1 nm-3 nm, wherein the β helical protein has a specific sequence linked to a functional molecule. Suitably the specific sequence is a penta-peptide repeat. In an embodiment, the consensus sequence of the recombinant β helical protein linked to a functional molecule is $(STAV)_1(DN)_2(LF)_3(STR)_4(G)_5$. Examples of pent-peptide repeat proteins are SEQ ID Nos: 1, 2, 6 and 8.

In embodiments of the present disclosure, the recombinant β helical protein is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

In embodiments of the present invention, the functional molecule can be any organic molecule (anticancer drugs, antibiotics, NSAIDS, pain relieving drugs or any other drug molecule, fluorescent dyes, insecticides, pesticides etc.), drug-metal complex, metal, antibody, protein, polysaccharide, nucleic acids, peptides, nuclear localising signal, quantum dots and nanoparticles.

The conjugate can be used to transfer a functional molecule inside the cells facilitated by the ability of the conjugate to penetrate the cell membrane. With appropriate localising signals associated with or integrated with the conjugate or the functional molecule or both, the conjugate of the present invention can be used to target the functional molecule to a specific part of the interior of the cell, for example, the organelles present inside the cells.

In an embodiment, the present invention also discloses a process for transferring a functional molecule inside the cells using the cell penetrating conjugate of the present invention. The process disclosed can further be used for cell labelling, cell penetration, and targeting of any functional molecule to cell organelles.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm.

In an embodiment of the present disclosure, there is provided a cell penetrating conjugate as described herein, wherein the β helical protein is a pentapeptide-repeat protein.

In an embodiment of the present disclosure, there is provided a cell penetrating conjugate as described herein, wherein the β helical protein comprises tandemly repeated pentapeptide with consensus sequence $(STAV)_1(DN)_2(LF)_3(STR)_4(G)_5$.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In an embodiment of the present disclosure, there is provided a cell penetrating conjugate as described herein, wherein the β helical protein is AlbG having a sequence as set forth in SEQ ID NO: 1.

In an embodiment of the present disclosure, there is provided a cell penetrating conjugate as described herein, wherein the β helical protein is EfsQNR having a sequence as set forth in SEQ ID NO: 2.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 3.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 4.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 5.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is QNRB1 having a sequence as set forth in SEQ ID NO: 6.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is UDP N-acetylglucosamine acyltransferase having a sequence as set forth in SEQ ID NO: 7.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is NP275 having a sequence as set forth in SEQ ID NO: 8.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is pectate lyase C having a sequence as set forth in SEQ ID NO: 9.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is a pectate lyase having a sequence as set forth in SEQ ID NO: 10.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is carbonic anhydrase having a sequence as set forth in SEQ ID NO: 11.

In an embodiment of the present disclosure, there is provided a cell penetrating conjugate comprising a recombinant β helical protein linked to a functional molecule, wherein the β helical protein length is in the range of 5 nm-25 nm, suitably, 10 nm-15 nm and width is in the range of 1 nm-5 nm, suitably 1 nm-3 nm, and wherein the β helical protein is Pectin Lyase A having a sequence as set forth in SEQ ID NO: 12.

In an embodiment of the present disclosure, there is provided a cell penetrating conjugate as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a cell penetrating conjugate as described herein, wherein the functional molecule is a dye.

In an embodiment of the present disclosure, there is provided a cell penetrating conjugate as described herein, wherein the functional molecule is a drug.

In an embodiment of the present disclosure, there is provided a cell penetrating conjugate as described herein, wherein the functional molecule is a metal.

In an embodiment of the present disclosure, there is provided a cell penetrating conjugate as described herein, wherein the functional molecule is a drug-metal complex.

In an embodiment of the present disclosure, there is provided a cell penetrating conjugate as described herein, wherein the functional molecule is a protein.

In an embodiment of the present disclosure, there is provided a cell penetrating conjugate as described herein, wherein the functional molecule is an enzyme.

In an embodiment of the present disclosure, there is provided a cell penetrating conjugate as described herein, wherein the functional molecule is an antibody.

In an embodiment of the present disclosure, there is provided a cell penetrating conjugate as described herein, wherein the functional molecule is a nucleic acid.

In an embodiment of the present disclosure, there is provided a cell penetrating conjugate as described herein, wherein the functional molecule is a polysaccharide.

In an embodiment of the present disclosure, there is provided a cell penetrating conjugate as described herein, wherein the functional molecule is a nuclear localising signal.

In an embodiment of the present disclosure, there is provided a cell penetrating conjugate as described herein, wherein the functional molecule is a nanoparticle.

In an embodiment of the present disclosure, there is provided a cell penetrating conjugate as described herein, wherein the functional molecule is linked to the recombinant β helical protein by covalent bonds, non-covalent bonds, and combinations thereof.

In an embodiment of the present disclosure, there is provided a cell penetrating conjugate as described herein, wherein the functional molecule is linked to the recombinant β helical protein by covalent bonds.

In an embodiment of the present disclosure, there is provided a cell penetrating conjugate as described herein, wherein the functional molecule is linked to the recombinant β helical protein by non-covalent bonds.

In an embodiment of the present disclosure, there is provided a cell penetrating conjugate comprising a recombinant β helical protein linked to a functional molecule as described herein, wherein the complex further comprises a signal sequence.

In an embodiment of the present disclosure, there is provided a cell penetrating conjugate comprising a recombinant β helical protein linked to a functional molecule as described herein, wherein the conjugate further comprises a phospholipid molecule.

In an embodiment of the present disclosure, there is provided a cell penetrating conjugate comprising a recombinant β helical protein linked to a functional molecule as described herein, wherein the conjugate further comprises a signal sequence selected from the group consisting of SEQ ID NO: 14, SEQ ID NO: 15, SEQ ID NO: 16, and SEQ ID NO: 17.

In an embodiment of the present disclosure, there is provided a cell penetrating conjugate comprising a recombinant β helical protein linked to a functional molecule as described herein, wherein the conjugate further comprises a phosphatidyl choline molecule.

In an embodiment of the present disclosure, there is provided a cell penetrating conjugate comprising a recombinant β helical protein linked to a functional molecule as described herein, wherein the conjugate further comprises a signal sequence as set forth in SEQ ID NO: 14.

In an embodiment of the present disclosure, there is provided a cell penetrating conjugate comprising a recombinant β helical protein linked to a functional molecule as described herein, wherein the conjugate further comprises a signal sequence as set forth in SEQ ID NO: 15.

In an embodiment of the present disclosure, there is provided a cell penetrating conjugate comprising a recombinant β helical protein linked to a functional molecule as described herein, wherein the conjugate further comprises a signal sequence as set forth in SEQ ID NO: 16.

In an embodiment of the present disclosure, there is provided a cell penetrating conjugate comprising a recombinant β helical protein linked to a functional molecule as described herein, wherein the conjugate further comprises a signal sequence as set forth in SEQ ID NO: 17.

In an embodiment of the present disclosure, there is provided a cell penetrating conjugate comprising a recombinant β helical protein linked to a functional molecule for transferring the functional molecule to nucleus of the cell, wherein the β helical protein length is in the range of 5 nm-25 nm, suitably, 10 nm-15 nm and width is in the range of 1 nm-5 nm, suitably 1 nm-3 nm, and wherein the conjugate further comprises a signal sequence as set forth in SEQ ID NO: 14.

In an embodiment of the present disclosure, there is provided a cell penetrating conjugate comprising a recombinant β helical protein linked to a functional molecule for transferring the functional molecule to nucleus of the cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the conjugate further comprises a signal sequence as set forth in SEQ ID NO: 14.

In an embodiment of the present disclosure, there is provided a cell penetrating conjugate comprising a recombinant β helical protein linked to a functional molecule for transferring the functional molecule to nucleus of the cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a cell penetrating conjugate comprising a recombinant β helical protein linked to a functional molecule for transferring the functional molecule to endoplasmic reticulum of the cell, wherein the β helical protein length is in the range of 5 nm-25 nm, suitably, 10 nm-15 nm and width is in the range of 1 nm-5 nm, suitably 1 nm-3 nm, and wherein the conjugate further comprises a signal sequence as set forth in SEQ ID NO: 15.

In an embodiment of the present disclosure, there is provided a cell penetrating conjugate comprising a recombinant β helical protein linked to a functional molecule for transferring the functional molecule to endoplasmic reticulum of the cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the conjugate further comprises a signal sequence as set forth in SEQ ID NO: 15.

In an embodiment of the present disclosure, there is provided a cell penetrating conjugate comprising a recombinant β helical protein linked to a functional molecule for transferring the functional molecule to endoplasmic reticulum of the cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a cell penetrating conjugate comprising a recombinant β helical protein linked to a functional molecule for transferring the functional molecule to mitochondria of the cell, wherein the β helical protein length is in the range of 5 nm-25 nm, suitably, 10 nm-15 nm and width is in the range of 1 nm-5 nm, suitably 1 nm-3 nm, and wherein the conjugate further comprises a signal sequence as set forth in SEQ ID NO: 16.

In an embodiment of the present disclosure, there is provided a cell penetrating conjugate comprising a recombinant β helical protein linked to a functional molecule for transferring the functional molecule to mitochondria of the cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the conjugate further comprises a signal sequence as set forth in SEQ ID NO: 16.

In an embodiment of the present disclosure, there is provided a cell penetrating conjugate comprising a recombinant β helical protein linked to a functional molecule for transferring the functional molecule to mitochondria of the cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a cell penetrating conjugate comprising a recombinant β helical protein linked to a functional molecule for transferring the functional molecule to P-cadherin overexpressing breast cancer cells, wherein the β helical protein length is in the range of 5 nm-25 nm, suitably, 10 nm-15 nm and width is in the range of 1 nm-5 nm, suitably 1 nm-3 nm, and wherein the conjugate further comprises a signal sequence as set forth in SEQ ID NO: 17.

In an embodiment of the present disclosure, there is provided a cell penetrating conjugate comprising a recombinant β helical protein linked to a functional molecule for transferring the functional molecule to P-cadherin overexpressing breast cancer cells as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the conjugate further comprises a signal sequence as set forth in SEQ ID NO: 17.

In an embodiment of the present disclosure, there is provided a cell penetrating conjugate comprising a recombinant β helical protein linked to a functional molecule for transferring the functional molecule to P-cadherin overexpressing breast cancer cells as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a cell penetrating conjugate comprising a recombinant β helical protein linked to a functional molecule for transferring the functional molecule to membrane of the cell, wherein the β helical protein length is in the range of 5 nm-25 nm, suitably, 10 nm-15 nm and width is in the range of 1 nm-5 nm, suitably 1 nm-3 nm, and wherein the conjugate further comprises a phosphatidyl choline molecule.

In an embodiment of the present disclosure, there is provided a cell penetrating conjugate comprising a recombinant β helical protein linked to a functional molecule for transferring the functional molecule to membrane of the cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the conjugate further comprises a phosphatidyl choline molecule.

In an embodiment of the present disclosure, there is provided a cell penetrating conjugate comprising a recombinant β helical protein linked to a functional molecule for transferring the functional molecule to membrane of the cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a process for transferring a functional molecule into a cell, said process comprising: (a) linking the functional molecule to a recombinant β helical protein to obtain a conjugate; (b) contacting the conjugate with at least one cell wherein contacting the conjugate transfers the functional molecule into the cell, and wherein length of the β helical protein is in the range of 5 nm-25 nm, suitably, 10 nm-15 nm and width is in the range of 1 nm-5 nm, suitably 1 nm-3 nm. In an embodiment, the process further comprises after step (c), step (d) detecting the transfer of the conjugate inside the cell.

In an embodiment of the present disclosure, there is provided a process for transferring a functional molecule into a cell as described herein, wherein the β helical protein is a pentapeptide-repeat protein.

In an embodiment of the present disclosure, there is provided a process for transferring a functional molecule into a cell as described herein, wherein the β helical protein comprises tandemly repeated pentapeptide with consensus sequence $(STAV)_1(DN)_2(LF)_3(STR)_4(G)_5$.

In an embodiment of the present disclosure, there is provided a process for transferring a functional molecule into a cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In an embodiment of the present disclosure, there is provided a process for transferring a functional molecule into a cell as described herein, wherein the β helical protein is AlbG having a sequence as set forth in SEQ ID NO: 1.

In an embodiment of the present disclosure, there is provided a process for transferring a functional molecule into a cell as described herein, wherein the β helical protein is EfsQNR having a sequence as set forth in SEQ ID NO: 2.

In an embodiment of the present disclosure, there is provided a process for transferring a functional molecule into a cell as described herein, wherein the β helical protein is an anti-freeze protein having a sequence as set forth in SEQ ID NO: 3.

In an embodiment of the present disclosure, there is provided a process for transferring a functional molecule into a cell as described herein, wherein the β helical protein is an anti-freeze protein having a sequence as set forth in SEQ ID NO: 4.

In an embodiment of the present disclosure, there is provided a process for transferring a functional molecule into a cell as described herein, wherein the β helical protein is an anti-freeze protein having a sequence as set forth in SEQ ID NO: 5.

In an embodiment of the present disclosure, there is provided a process for transferring a functional molecule into a cell as described herein, wherein the β helical protein is QNRB1 having a sequence as set forth in SEQ ID NO: 6.

In an embodiment of the present disclosure, there is provided a process for transferring a functional molecule into a cell as described herein, wherein the β helical protein is UDP N acetylglucosamine acyltransferase having a sequence as set forth in SEQ ID NO: 7.

In an embodiment of the present disclosure, there is provided a process for transferring a functional molecule into a cell as described herein, wherein the β helical protein is NP275 having a sequence is as set forth in SEQ ID NO: 8.

In an embodiment of the present disclosure, there is provided a process for transferring a functional molecule into a cell as described herein, wherein the β helical protein is pectate lyase C having a sequence as set forth in SEQ ID NO: 9.

In an embodiment of the present disclosure, there is provided a process for transferring a functional molecule into a cell as described herein, wherein the β helical protein is a pectate lyase having a sequence as set forth in SEQ ID NO: 10.

In an embodiment of the present disclosure, there is provided a process for transferring a functional molecule into a cell as described herein, wherein the β helical protein is carbonic anhydrase having a sequence as set forth in SEQ ID NO: 11.

In an embodiment of the present disclosure, there is provided a process for transferring a functional molecule into a cell as described herein, wherein the β helical protein having a sequence is as set forth in SEQ ID NO: 12.

In an embodiment of the present disclosure, there is provided a process for transferring a functional molecule into a cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a process for transferring a functional molecule into a cell as described herein, wherein the functional molecule is a dye.

In an embodiment of the present disclosure, there is provided a process for transferring a functional molecule into a cell as described herein, wherein the functional molecule is a drug.

In an embodiment of the present disclosure, there is provided a process for transferring a functional molecule into a cell as described herein, wherein the functional molecule is a metal.

In an embodiment of the present disclosure, there is provided a process for transferring a functional molecule into a cell as described herein, wherein the functional molecule is a drug-metal complex.

In an embodiment of the present disclosure, there is provided a process for transferring a functional molecule into a cell as described herein, wherein the functional molecule is a protein.

In an embodiment of the present disclosure, there is provided a process for transferring a functional molecule into a cell as described herein, wherein the functional molecule is an enzyme.

In an embodiment of the present disclosure, there is provided a process for transferring a functional molecule into a cell as described herein, wherein the functional molecule is an antibody.

In an embodiment of the present disclosure, there is provided a process for transferring a functional molecule into a cell as described herein, wherein the functional molecule is a nucleic acid.

In an embodiment of the present disclosure, there is provided process for transferring a functional molecule into a cell as described herein, wherein the functional molecule is a polysaccharide.

In an embodiment of the present disclosure, there is provided a process for transferring a functional molecule into a cell as described herein, wherein the functional molecule is a nuclear localising signal.

In an embodiment of the present disclosure, there is provided a process for transferring a functional molecule into a cell as described herein, wherein the functional molecule is a nanoparticle.

In an embodiment of the present disclosure, there is provided a process for transferring a functional molecule into a cell as described herein, wherein the functional molecule is linked to the recombinant β helical protein by covalent bonds, non-covalent bonds, and combinations thereof.

In an embodiment of the present disclosure, there is provided a process for transferring a functional molecule into a cell as described herein, wherein the cell is selected from the group consisting of eukaryotic cells, prokaryotic cells, and combinations thereof.

In an embodiment of the present disclosure, there is provided a process for transferring a functional molecule into a cell as described herein, wherein the cell is a prokaryotic cell.

In an embodiment of the present disclosure, there is provided a process for transferring a functional molecule into a cell as described herein, wherein the cell is a eukaryotic cell.

In an embodiment of the present disclosure, there is provided a process for transferring a functional molecule into a cell as described herein, wherein the β helical protein is represented by a sequence as set forth in SEQ ID NO: 1, and the functional molecule is NHS-coumarin dye.

In an embodiment of the present disclosure, there is provided a process for transferring a functional molecule into a cell as described herein, wherein the β helical protein is represented by a sequence as set forth in SEQ ID NO: 2, and the functional molecule is NHS-coumarin dye.

In an embodiment of the present disclosure, there is provided a process for transferring a functional molecule into a cell as described herein, wherein the β helical protein is represented by a sequence as set forth in SEQ ID NO: 2, and the functional molecule is ruthenium metal complex.

In an embodiment of the present disclosure, there is provided a process for transferring a functional molecule into a cell as described herein, wherein the process is used for cell-labelling.

In an embodiment of the present disclosure, there is provided a process for transferring a functional molecule into a cell as described herein, wherein the process is used for delivering the functional molecules into the cell.

In an embodiment of the present disclosure, there is provided a process for transferring a functional molecule to an organelle of a cell, said process comprising: (a) linking the functional molecule to a recombinant β helical protein to obtain a conjugate; (b) further incorporating to the conjugate any one signal sequence selected from the group consisting of SEQ ID NO: 14, SEQ ID NO: 15, and SEQ ID NO: 16; (c) contacting the conjugate of step (b) with at least one cell; wherein contacting the conjugate of step (b) transfers the functional molecule to the organelle inside the cell, wherein the organelle is selected from the group consisting of nucleus, endoplasmic reticulum, and mitochondria, and wherein the β helical protein length is in the range of 5 nm-25 nm, suitably, 10 nm-15 nm and width is in the range of 1 nm-5 nm, suitably 1 nm-3 nm. In an embodiment, the process further comprises after step (c), step (d) detecting the transfer of the conjugate inside the cell.

In an embodiment of the present disclosure, there is provided a process for transferring a functional molecule to an organelle of a cell as described herein, wherein the recombinant β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In an embodiment of the present disclosure, there is provided a process for transferring the functional molecules to nucleus of the cell as described herein, wherein the signal sequence is as set forth in SEQ ID NO: 14.

In an embodiment of the present disclosure, there is provided a process for transferring the functional molecules to endoplasmic reticulum of the cell as described herein, wherein the signal sequence is as set forth in SEQ ID NO: 15.

In an embodiment of the present disclosure, there is provided a process for transferring the functional molecules to mitochondria of the cell as described herein, wherein the signal sequence is as set forth in SEQ ID NO: 16.

In an embodiment of the present disclosure, there is provided a process for transferring a functional molecule to an organelle of a cell as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a process for transferring a functional molecule to P-cadherin-over expressing breast cancer cells, said process comprising: (a) linking the functional molecule to a recombinant β helical protein to obtain a complex; (b) further incorporating a signal sequence as set forth in SEQ ID NO: 17 to the complex; (c) contacting the complex of step (b) with at least one P-cadherin-over expressing breast cancer cell; wherein contacting the complex of step (b) transfers the functional molecule into the P-cadherin-over expressing breast cancer cell, wherein the β helical protein length is in the range of 5 nm-25 nm, suitably, 10 nm-15 nm and width is in the range of 1 nm-5 nm, suitably 1 nm-3 nm. In an embodiment, the process further comprises after step (c), step (d) detecting the transfer of the complex inside the cell.

In an embodiment of the present disclosure, there is provided a process for transferring a functional molecule to P-cadherin-over expressing breast cancer cells as described herein, wherein the recombinant β helical protein having a sequence is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

In an embodiment of the present disclosure, there is provided a process for transferring a functional molecule to P-cadherin-over expressing breast cancer cells as described herein, wherein the functional molecule is selected from the group consisting of dyes, drugs, metal, drug-metal complex, proteins, enzymes, antibodies, nucleic acids, polysaccharides, nuclear localizing signals, nanoparticles, and combinations thereof.

In an embodiment of the present disclosure, there is provided a process as described herein, wherein the process is used for targeted delivery of the functional molecule into the cell.

In an embodiment of the present disclosure, there is provided a process as described herein, wherein the process is used for labelling of the cell.

In an embodiment of the present disclosure, there is provided a process as described herein, wherein the process is used for targeted delivery of drugs in the cell.

In an embodiment of the present disclosure, there is provided a cell penetrating complex as described herein, wherein the recombinant β helical protein is used for delivering the functional molecule into the cell, and wherein the functional molecule is selected from the group consisting of dyes, drugs, metal, drug-metal conjugate, proteins, enzymes, antibodies, nucleic acids, polysaccharides, nuclear localizing signals, nanoparticles, and combinations thereof.

In an embodiment of the present disclosure, there is provided a process for transferring a functional molecule to actin protein present in a cell, said process comprising: (a) linking the functional molecule to a recombinant β helical protein to obtain a conjugate; (b) further incorporating a signal sequence as set forth in SEQ ID NO: 22 to the complex; (c) contacting the conjugate of step (b) with at least one cell; wherein contacting the conjugate of step (b) transfers the functional molecule into the cell, wherein the β helical protein length is in the range of 5 nm-25 nm, suitably, 10 nm-15 nm and width is in the range of 1 nm-5 nm, suitably 1 nm-3 nm. In an embodiment, the process further comprises after step (c), step (d) detecting the transfer of the conjugate inside the cell.

In an embodiment of the present disclosure, there is provided a process for transferring a functional molecule to tubulin protein present in a cell, said process comprising: (a) linking the functional molecule to a recombinant β helical protein to obtain a conjugate; (b) further incorporating a signal sequence as set forth in SEQ ID NO: 23 to the conjugate; (c) contacting the conjugate of step (b) with at least one cell; wherein contacting the conjugate of step (b) transfers the functional molecule into the P-cadherin-over expressing breast cancer cell, wherein the β helical protein length is in the range of 5 nm-25 nm, suitably, 10 nm-15 nm and width is in the range of 1 nm-5 nm, suitably 1 nm-3 nm. In an embodiment, the process further comprises after step (c), step (d) detecting the transfer of the conjugate inside the cell.

In an embodiment of the present disclosure, there is provided a cell penetrating conjugate as described herein, wherein the recombinant β helical protein is used for cell penetration.

In an embodiment of the present disclosure, there is provided a cell penetrating conjugate as described herein, wherein the recombinant β helical protein is used for cell labelling.

Cell Penetrating Molecule with Nucleic Acids

In an embodiment, the present invention provides a solution to the problem of delivery of nucleic acid fragments, as a functional molecule, that is faced by gene therapy or gene editing treatments. The present document discloses a conjugate comprising a recombinant β helical protein linked to a nucleic acid molecule, for example a plasmid, such as an RNA- or DNA-plasmid, which can penetrate the cell membrane. In an embodiment, the recombinant β helical protein linked may be linked to one or more nucleic acid molecules, suitably a single nucleic acid molecule or plasmid, by suitable interactive forces (such as electrostatic or hydrophobic forces) or via a linker element, molecule, portion or moiety.

The conjugate comprising recombinant β helical protein, a linker and a plasmid is shown to successfully penetrate the cell membrane to establish the expression of a gene forming the part of the plasmid. The conjugate avoids the pathway of endocytosis and crosses the cell membrane by directly penetrating the membrane. The conjugate hence overcomes the problems faced by entry through endocytosis and at the same time effectively penetrating the cell membrane.

In an embodiment, the present invention discloses a conjugate capable of penetrating cell membrane. In some embodiments, the conjugate comprises a recombinant β helical protein of length in the range of 5 nm-25 nm, suitably, 10 nm-15 nm and width is in the range of 1 nm-5 nm, suitably 1 nm-3 nm linked to a nucleic acid molecule via a linker. In an embodiment, the recombinant β helical protein can be a pentapeptide repeat protein have a consensus sequence $(STAV)_1(DN)_2(LF)_3(STR)_4(G)_5$. In another embodiment of the present disclosure, the recombinant β helical protein is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

According to the present disclosure, in an embodiment the recombinant β helical protein is linked to a nucleic acid molecule by a linker element, molecule, portion or moiety. In embodiments, the linker element may be a direct link by covalent or non-covalent bonds. When the linker is a linker molecule it may be selected from the group consisting of protein, metal conjugate, drug-metal conjugate, DNA binding domain, and nucleic acid intercalating molecule. In an embodiment, the nucleic acid molecule comprising the part of the conjugate comprises at least one gene of interest. In an embodiment, the nucleic acid molecule is linked to a complex comprising the recombinant β helical protein and the linker to form the conjugate as disclosed in the present invention. In an embodiment, the conjugate is able to enter the cell by penetrating the cell membrane and a gene forming a part of the nucleic acid molecule is able to express inside the cells.

The present invention also discloses a process for transferring a nucleic acid molecule inside the cells using the conjugate of the present invention. In an embodiment, the process disclosed can further be used for gene therapy techniques or gene-editing techniques for facilitating non-viral approaches for delivering the gene of interest in a cell, thereby effectively enabling editing of a defective gene, or compensating for a defective gene or protein, inside the cell.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is a pentapeptide repeat protein.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein comprises tandemly repeated pentapeptide with consensus sequence $(STAV)_1(DN)_2(LF)_3(STR)_4(G)_5$.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the linker is a linker molecule selected from the group consisting of protein, metal conjugate, drug-metal conjugate, DNA binding domain, nucleic acid intercalating molecule, and combinations thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the linker is a linker molecule selected from the group consisting of protein, metal conjugate, drug-metal conjugate, DNA binding domain, nucleic acid intercalating molecule, and combinations thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the linker is linked to the recombinant β helical protein by covalent bonds, non-covalent bonds, and combinations thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the linker is a linker molecule selected from the group consisting of protein, metal conjugate, drug-metal conjugate, DNA binding domain, nucleic acid intercalating molecule and combinations thereof, and wherein the linker is linked to the recombinant β helical protein by covalent bonds, non-covalent bonds, and combinations thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the nucleic acid molecule comprises at least one gene of interest.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the nucleic acid molecule comprises at least one gene of interest.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the linker is a linker molecule selected from the group consisting of protein, metal conjugate, drug-metal conjugate, DNA binding domain, nucleic acid intercalating molecule and combinations thereof, and wherein the nucleic acid molecule comprises at least one gene of interest.

In an embodiment, the present invention provides a solution to the problem of delivery of gene editing molecular machinery across cellular membranes and into a cell and/or compartments thereof by providing a means of transfecting a plasmid or nucleic acid encoding one or more molecules of a genome-editing system in to the cell. Once the plasmid or nucleic acid is in the cell, the one or more molecules of a genome-editing system in to the cell may be prepared using cellular processes and optionally combined with other required components of the genome-editing system, to provide a complete gene editing system within the cell.

In an embodiment of the present disclosure, the gene of interest in the nucleic acid, or plasmid, encodes one or more molecules of a genome-editing system. Suitably, the one or more molecules of the genome-editing system are selected from, but not limited to, the group consisting of: an RNA-guided endonuclease and/or a guide RNA (gRNA), for example Cas9; a zinc finger nuclease (ZFN); a transcriptor activator-like effector nuclease (TALEN®); a DNA-guided endonuclease and/or a guide DNA; a homing endonuclease; an integrase; and any combination thereof.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is AlbG having a sequence as set forth in SEQ ID NO: 1.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is EfsQNR having a sequence as set forth in SEQ ID NO: 2.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 3.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 4.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is an anti-freeze protein having a sequence as set forth in SEQ ID NO: 5.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is QNRB1 having a sequence as set forth in SEQ ID NO: 6.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is UDP N acetylglucosamine acyltransferase having a sequence as set forth in SEQ ID NO: 7.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is NP275 having a sequence as set forth in SEQ ID NO: 8.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is pectate lyase C having a sequence as set forth in SEQ ID NO: 9.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is a pectate lyase having a sequence as set forth in SEQ ID NO: 10.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is carbonic anhydrase having a sequence as set forth in SEQ ID NO: 11.

In an embodiment of the present disclosure, there is provided a conjugate comprising: (a) at least one recombinant β helical protein; (b) at least one linker; and (c) at least one nucleic acid molecule, wherein the at least one recombinant β helical protein length is in the range of 5 nm-25 nm, suitably, 10 nm-15 nm and width is in the range of 1 nm-5 nm, suitably 1 nm-3 nm, and wherein the β helical protein is Pectin Lyase A having a sequence as set forth in SEQ ID NO: 12.

In an embodiment of the present disclosure, there is provided a process for transferring a nucleic acid molecule, or plasmid, into a cell, said process comprising: (i) linking the nucleic acid molecule to a complex comprising: (a) at least one recombinant β helical protein; and (b) at least one linker to obtain a conjugate; and (ii) contacting the conjugate to at least one cell, wherein contacting the conjugate transfers the nucleic acid molecule into the cell, and wherein the recombinant β helical protein length is in the range of 5 nm-25 nm, suitably, 10 nm-15 nm and width is in the range of 1 nm-5 nm, suitably 1 nm-3 nm.

In an embodiment of the present disclosure, there is provided a process for transferring a nucleic acid molecule, or plasmid, into a cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In an embodiment of the present disclosure, there is provided a process for transferring a nucleic acid molecule into a cell as described herein, wherein the β helical protein is a pentapeptide repeat protein.

In an embodiment of the present disclosure, there is provided a process for transferring a nucleic acid molecule into a cell as described herein, wherein the β helical protein comprises tandemly repeated pentapeptide with consensus sequence $(STAV)_1(DN)_2(LF)_3(STR)_4(G)_5$.

In an embodiment of the present disclosure, there is provided a process for transferring a nucleic acid molecule into a cell as described herein, wherein the linker is a linker molecule selected from the group consisting of protein, metal conjugate, drug-metal conjugate, DNA binding domain, nucleic acid intercalating molecule, and combinations thereof.

In an embodiment of the present disclosure, there is provided a process for transferring a nucleic acid molecule into a cell as described herein, wherein the β helical protein is represented by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof, and wherein the linker is a linker molecule selected from the group consisting of protein, metal conjugate, drug-metal conjugate, DNA binding domain, nucleic acid intercalating molecule, and combinations thereof.

In an embodiment of the present disclosure, there is provided a process for transferring a nucleic acid molecule into a cell as described herein, wherein the linker is linked to the recombinant β helical protein by covalent bonds, non-covalent bonds, and combinations thereof.

In an embodiment of the present disclosure, there is provided a process for transferring a nucleic acid molecule into a cell as described herein, wherein the linker is a linker molecule selected from the group consisting of protein, metal conjugate, drug-metal conjugate, DNA binding domain, nucleic acid intercalating molecule and combinations thereof, and wherein the linker is linked to the recombinant β helical protein by covalent bonds, non-covalent bonds, and combinations thereof.

In an embodiment of the present disclosure, there is provided a process for transferring a nucleic acid molecule into a cell as described herein, wherein the cell is either a prokaryotic cell or a eukaryotic cell.

In an embodiment of the present disclosure, there is provided a process for transferring a nucleic acid molecule into a cell as described herein, wherein the gene of interest in the nucleic acid, or plasmid, encodes one or more molecules of a genome-editing system. Suitably, the one or more molecules of the genome-editing system are selected from, but not limited to, the group consisting of: an RNA-guided endonuclease and/or a guide RNA (gRNA), for example Cas9; a zinc finger nuclease (ZFN); a transcriptor activator-like effector nuclease (TALEN®); a DNA-guided endonuclease and/or a guide DNA; a homing endonuclease; an integrase; and any combination thereof.

Cell Penetrating Peptide for Efficient Transfer of Gene Editing Molecules Across Cell Membranes The present invention provides a solution to the problem of delivery of gene editing molecular machinery across cellular membranes and into a cell and/or compartments thereof. The present document discloses a conjugate comprising a recombinant β helical protein linked to at least one gene editing molecule or a gene editing complex which can efficiently penetrate the cell membrane. In an embodiment, the recombinant β helical protein may be linked by non-covalent interactions to an endonuclease and one or more gRNA molecules. In one embodiment, the recombinant β helical protein may be linked by non-covalent interactions to CRISPR gene editing molecules, for example Cas9 endonuclease or gRNAs and/or to a complex of Cas9 and one or more gRNA molecules.

The conjugate comprising recombinant β helical protein and CRISPR gene editing molecules is shown to successfully penetrate the cell membrane to enable site-specific editing of the genome. Without wishing to be bound by theory, it is postulated that the conjugate avoids the pathway of endocytosis and crosses the cell membrane by directly penetrating the membrane. The conjugate hence overcomes the problems faced by entry through endocytosis and at the same time effectively penetrating the cell membrane.

In some embodiments, the conjugate comprises a recombinant β helical protein of length in the range of 5 nm-25 nm, suitably, 10 nm-15 nm and width is in the range of 1 nm-5 nm, suitably 1 nm-3 nm linked to a nucleic acid molecule via a linker. In an embodiment, the recombinant β helical protein can be a pentapeptide repeat protein have a consensus sequence $(STAV)_1(DN)_2(LF)_3(STR)_4(G)_5$. In another embodiment of the present disclosure, the recombinant β helical protein is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

According to the present disclosure, in an embodiment the recombinant β helical protein is linked to a nucleic acid molecule by a linker element, molecule, portion or moiety. In embodiments, the linker element may be a direct link by covalent or non-covalent bonds. When the linker is a linker molecule it may be selected from the group consisting of protein, metal conjugate, drug-metal conjugate, DNA binding domain, and nucleic acid intercalating molecule.

In an embodiment, the conjugate is able to enter the cell by penetrating the cell membrane and migrate to a relevant genome where site-specific editing can take place.

The present invention also discloses a process for transferring a CRISPR-RNP inside the cells using the conjugate of the present invention. In an embodiment, the process disclosed can further be used for gene editing techniques for facilitating non-viral approaches for allowing existing genes to be edited, removed and/or new ones added.

In an embodiment of the present disclosure, there is provided a process for transferring a CRISPR-RNP into a cell as described herein, wherein the cell is either a prokaryotic cell or a eukaryotic cell.

In an embodiment of the present disclosure, there is provided a conjugate as described herein, wherein the conjugate is used as a transfecting agent.

In an embodiment of the present disclosure, there is provided a conjugate as described herein, wherein the conjugate is used for gene therapy.

EXAMPLES—Cell Penetrating Molecule with Functional Molecules

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed processes and compositions, the exemplary processes, devices and materials are described herein. It is to be understood that this disclosure is not limited to particular methods, and experimental conditions described, as such processes and conditions may vary.

In the following examples, methods and protocols for carrying out plasmid and protein studies have been provided. Also provided are the protocols for obtaining the conjugate, labelling of the protein, and methods of carrying out cell penetration studies using protein-drug conjugate and protein-label conjugate. The results section specifically describes the proof-of-concept of the cell penetration ability of the conjugate as disclosed in the present invention. The in-vitro labelling of different cell lines has been carried out using the conjugate of the present invention as per the method disclosed. The assay with a drug-protein conjugate have also been carried out to study the ability of the conjugate in enhancing the drug uptake by cell penetration.

Material and Methods

The dye Hoechst 33342 was procured from Invitrogen; NHS-coumarin, and ATTO 520-NHS, ATTO 390-NHS and ATTO 647N-NHS were procured from Sigma. The organic solvents and reagents used for UV-visual spectrophotometry and CD spectra were procured from Sigma and Merck. The reagents for studying the expression of plasmids and purification of proteins were procured from Sigma Aldrich and Merck. The reagents required for MTT assay were procured from MP Biomedicals. Ruthenium metal complex was procured from Sigma.

Example 1

Plasmid/Protein studies—The plasmid containing AlbG gene as shown in SEQ ID NO: 19, was obtained by a method as published previously (Vetting et al. Acta Crystallogr. Sect. F Struct. Biol. Cryst. Commun. 2011: 67(3): 296-302, the contents of which is incorporated herein by reference and specific details provided below).

The open reading frame of AlbG was amplified by standard PCR techniques using *X albilineans* (ATCC 29184; Pieretti et al., BMC Genomics, 2009, 10:616, 1-15) chromosomal DNA as a template. The oligonucleotides AlbGF (5'-ATCCCGCTCATATGCCGGCCAAGACCCTTG-3')

and AlbGR (5'-ATCCCGCTCTCGAGTCAATCGGACAGCTCGATATC-3')

containing NdeI and XhoI restriction sites, respectively, were used. The PCR fragment was cloned into pET-28a(+) and recombinant AlbG bearing a thrombin-cleavable N-terminal His6 tag was expressed in *E. coli* strain BL21 (DE3). For shake-flask growth, 1 liter of Luria broth medium supplemented with kanamycin (35 µg/ml) was inoculated with 10 ml of an overnight culture and incubated at 37° C. The culture was grown to mid-log phase ($A_{600}$ of ~0.8), cooled to 20° C., induced with 0.5 mM IPTG and further incubated overnight at 20° C. All purification procedures were carried out at 4° C. The cells were collected by centrifugation at 3000 g, re-suspended in buffer A [50 mM Tris-HCl pH 7.8 containing 300 mM NaCl, protease inhibitors, lysozyme (5 µg/ml) and DNase I (0.1 µg/ml)] and stirred for 20 min. The cells were then lysed by sonication and cell debris was removed by centrifugation at 10 000 g for 30 min. The supernatant was loaded onto a nickel-nitrilotriacetic acid (Ni-NTA) column pre-equilibrated with buffer A and washed with ten column volumes of the same buffer. The bound proteins were eluted with a linear 0 to 0.3 M imidazole gradient and the peak fractions were pooled and concentrated.

The plasmid containing EfsQNR gene as shown in SEQ ID NO: 2 was obtained by a method as published previously (Hegde et al., Antimicrob. Agents Chemother. 2011 January; 55 (1): 110-117, the contents of which is incorporated herein by reference and details provided below).

The open reading frame of EfsQNR was amplified by standard PCR techniques using *E. faecalis* V583 (ATCC 700802; ENTFA 226185) chromosomal DNA as the template. The oligonucleotides (5'-ATCCCGCTCATATGAAAATAACTTATCCCTTGCCA-3')

and (5'-ATCCCGCTCTCGAGTTAGGTAATCACCAAACCAAGT-3'), containing NdeI and XhoI restriction sites, respectively, were used. The PCR fragment was cloned into pET-28a(+), and the recombinant EfsQNR bearing a thrombin-cleavable N-terminal His6 tag was expressed in *E. coli* strain BL21 (DE3). For shake flask growth, 1 liter of Luria broth medium supplemented with kanamycin (35 µg/ml) was inoculated with 10 ml of an overnight culture and incubated at 37° C. The culture was grown to mid-log phase ($A_{600}$~0.8), cooled to 20° C., induced with 0.5 mM isopropyl-β-d-thiogalacto-pyranoside (IPTG), and further incubated overnight at 20° C.

The cells were collected by centrifugation at 1,200 g and re-suspended in buffer A (50 mM Tris-HCl [pH 7.8], 300 mM NaCl) containing protease inhibitors, lysozyme (5 µg/ml), and DNase I (0.1 µg/ml), and the mixture was stirred for 20 min. The cells then were lysed by sonication, and cell debris was removed by centrifugation at 10,000 g for 30 min. The supernatant was loaded onto a Ni-NTA column pre-equilibrated with buffer A and washed with 10 column volumes of the same buffer. The bound proteins were eluted with a linear 0 to 0.3 M imidazole gradient with fractions pooled and concentrated.

As a comparative example, a plasmid containing TtCuA gene as shown in SEQ ID NO: 13 was obtained by a method in Biochemistry, 2008, 47, 1309-1318, which is incorporated herein by reference.

Example 2

Toxicity assay—The industry-standard MTT assay (ex-Sigma Aldrich) was performed to analyse the toxicity of β-helical protein-cytotoxic drug conjugates against mammalian cells, for example HeLa cells. The cells were cultured by using standard protocol. One million cells were seeded in confocal plates (1 cm dish), grown for 6-8 h. A mixture of the cytotoxic drug and the EfsQNR protein (mixed at a ratio of 2:1) was added to the cells and incubated at room temperature for 15 minutes to 24 h to 72 h. After the incubation, the cells were washed with PBS and treated with MTT and further incubated for 24 hours. The cells were then washed and analysed for absorbance values at 570 nm. Viable cells with active metabolism convert MTT into a purple coloured formazan product with an absorbance maximum near 570 nm. Dead cells cannot convert MTT into formazan therefore, by analysing the absorbance values at 570 nm percentage of viable cells can be calculated for a given protein or any other molecule.

Example 3

Labelling of proteins with fluorescent dyes—Fluorescent dyes were considered as an example of a functional molecule for investigating the cell membrane penetration ability of the conjugate. Labelling of the recombinant protein with a dye was carried out by performing a series of reaction in dark conditions. The protein to be labelled was collected in PBS buffer (1× and pH 7.3) and the dye was collected at two to three times higher concentration to that of the protein. The protein was added to 0.1M sodium carbonate buffer (pH 8.5) followed by the dye. The dye was added very slowly (3 µl each time) to the buffer containing the protein kept on ice accompanied by occasional shaking. The resulting solution was wrapped with aluminium foil to keep away any light. The solution was stirred for 1 hour at room temperature and was then purified by gel filtration, i.e. passed through a desalting column or a PD 10 column with 1×PBS buffer. The resulting labelled protein was characterized using UV-visual spectrophotometry to determine dye: protein ratio.

Example 4

Cellular uptake of labelled proteins—The uptake of labelled proteins was checked by treating mammalian cells with different labelled proteins such as AlbG (SEQ ID NO: 1), EfsQNR (SEQ ID NO: 2) and, as a comparative example, TtCuA (SEQ ID NO: 13). TtCuA is a cytochrome oxidase c protein from the organism *Thermus thermophilus*. It is represented by the amino acid sequence as set forth in SEQ ID NO: 13. The cells were seeded at a concentration of one million in confocal plates (1 cm dish) and allowed to grow for 6-8 hours. Subsequently, the labelled proteins were added to the cells at different concentrations and incubated under standard conditions of 5% $CO_2$ and 37° C. The cells were then washed twice, after 3 hours and 24 hours with HBSS (Hanks blank salt solution) or PBS and observed under fluorescence microscopy and/or confocal laser scanning microscope.

The uptake of labelled proteins was checked by treating *E-coli* and yeast (Kluveromyces) cells with different labelled proteins such as AlbG (SEQ ID NO: 1), EfsQNR (SEQ ID NO: 2). *E coli* or Kluveromyces cells were inoculated and grown overnight until OD reached 0.6. The cells were diluted to 50 times and 3 micromolar labelled protein (conjugate) was added. The cells were further grown under standard growth condition (37° C. shaking condition) for 24 h. The treated cells were then centrifuged and washed in PBS for 3-4 times. Then the cells were dispersed in 100 microliter PBS and then imaged in fluorescence/confocal microscope.

In addition, different proteins such as AlbG (SEQ ID NO: 1), EfsQNR (SEQ ID NO: 2) labelled with a green fluorescent dye (A-520) were found to be taken up into several drug resistant strains of bacteria (*Pseudovibrio* sp. Ad37/5/13/14 and *Enterobacter*, wherein the strain *Enterobacter* sp. is resistant to antibiotics such as erythromycin, chloramphenicol, tetracycline, nalidixic acid, kanamycin and penicillin), yeast cells (*Saccharomyces cerevisiae, Kluveromyces marxianus* and *Candida albicans*), plant cells (*Arabidopsis*), zebrafish embryos and drosophila embryos as observed by confocal laser scanning microscopy.

Protocol for Uptake in Bacteria and Yeast Cells:
- Respective bacteria and yeast strains were inoculated the day before the experiment and allowed to grow overnight;
- The cells were centrifuged and 2 ml fresh media was added;
- 100-200 μL of cells were added to the mixture;
- 10 μM of green labelled CPP was added;
- Fresh media was added to bring the volume to 1 mL;
- After 24 hours the treated cells were centrifuged and washed in PBS 3-4 times;
- the cells were dispersed in 100 microliter PBS and then imaged in fluorescence/confocal microscope (FIGS. 25 and 26).

Protocol for Uptake in Plant Cells (*Arabidopsis*):
- Plants were grown for 7 days prior to the experiment;
- 20 μM of different cell-penetrating proteins such as AlbG (SEQ ID NO: 1), EfsQNR (SEQ ID NO: 2) labelled with a green fluorescent dye (A-520) were added to the plants in buffer [3 plants grown for 7 days] in 500 μL PBS;
- The mixture was placed in a growth room for 24 hours under standard growth conditions (kept static in a room of continuous supply of light and 23° C. temperature);
- The plants were washed with PBS 3 times and fresh PBS was then added and cells visualized under microscope. Non-coloured cells such as the cells of the roots and stems were chosen for visualisation to avoid interference (FIGS. 23 and 24).

Protocols for Uptake in Zebrafish Embryo and Drosophila Embryo:
- Embryos of zebrafish and drosophila were collected and washed in PBS
- 10 μM of different cell-penetrating proteins such as AlbG (SEQ ID NO: 1), EfsQNR (SEQ ID NO: 2) labelled with a green fluorescent dye (A-520) were added into the vial containing the embryos and incubated for 2 h;
- The embryos were collected washed with PBS three times and dispersed in PBS and put on glass cover slips and visualized under microscope (FIGS. 27 and 28).

These results give an indication that the CPP of the present invention can transfer cargoes into the cytoplasm of a wide variety of cell types by crossing the cell membrane and/or cell wall. This opens the prospect of conjugating the CPP with antibiotics such as Ciprofloxacin and Penicillin or any other antibiotic by using the activated acid coupling chemistry (EDC/NHS) to conjugate the carboxylate (—COOH) groups of the drugs and amine groups of the CPP (from the lysine residues). These reactions are well known in the literature and text book (Reference: Bioconjugate Techniques page 264-265 by Greg T Hermansen). Use of linkers such as adipic acid dihydrazide, succinimidyl 6-hydrazinonicotinate acetone hydrazine, C6-succinimidyl 6-hydrazinonicotinate acetone hydrazine, succinimidyl hydraziniumnicotinate hydrochloride to conjugate CPP with antibiotics. These linkers are known to be hydrolysable under intracellular conditions to release the antibiotics inside the cells.

Antibiotic-CPP conjugate would improve the efficiency of cellular uptake when compared to the unconjugated antibiotic and reduce or eliminate drug expulsion through cellular mechanisms, such as glycoproteins. The binding site of glycoproteins is in the region of <1 kDa whereas CPP-drug conjugates are of the size 48 KDa. This could help in improving old antibiotics and contribute to addressing the issue of antimicrobial drug resistance. Similarly the technique can be used to improve the efficiency of antibiotics/pesticides/nutrients delivery in fishes and plants.

Example 5

Cellular uptake of drug—HeLa cells were used for determining the enhanced uptake of the drug using the cell penetrating conjugate of the present invention. HeLa cells were seeded at a concentration of 10,000 in a 96-well plate and allowed to grow for 6-8 hours. Ruthenium metal complex and EfsQNR were mixed in different ratios of 1:1, 1:2, and 1:3 to form a conjugate, which was subsequently added to the cells. The conjugate formed of ruthenium to EfsQNR in a ratio of 1:2 yielded an enhanced result. The cell death after 24 hours was monitored by MTT assay as described previously and was correlated to the percentage uptake of ruthenium-EfsQNR conjugate by HeLa cells.

Results of Examples 1 to 5

Characterization of Proteins and Conjugates

Structural specificity—The size of the AlbG protein was determined from the published crystal structure pdb id: 2xt2.pdb. By measuring the end to end atom distance of dimeric structure in Pymol®, the length was determined to be 10.7 nm, and the width (diameter) to be 2.6 nm. The total formal charge was-27. There are alternatively arranged positive and negative charge residues: Presence of an arginine ladder (total of 20 Arg residues), Lysine (14 residues) and aspartic acid (30 Asp residues) and glutamic acid (31 Glu residues). Asparagine (20 Asn residues) ladder along the surface of the protein.

The size of the EfsQNR protein was determined from the published crystal structure pdb id: 2w7z.pdb. By measuring the end to end atom distance of the dimeric structure in Pymol®, the length of the protein was determined to be 10.9 nm, and the width (diameter) to be 2.8 nm. Total formal charge −41. Alternatively arranged positive and negative charge residues: Presence of an arginine ladder (total of 16 Arg residues), Lysine (12 residues) and aspartic acid (25 Asp residues) and glutamic acid (33 Glu residues). Asparagine (33 Asn residues) ladder along the surface of the protein.

For comparison, the size of the TtCuA protein was determined from the published crystal structure pdb id: 2CuA.pdb. By measuring the end to end atom distance of structure in Pymol®, the length was determined to be 3.3 nm, and the width (diameter) to be 1.9 nm. The structure comprises 5 Arginine residues, 4 Lysine residues, 9 Glutamic acid residues and 6 Asparagine residues with a total charge of 3.

Figure 1:
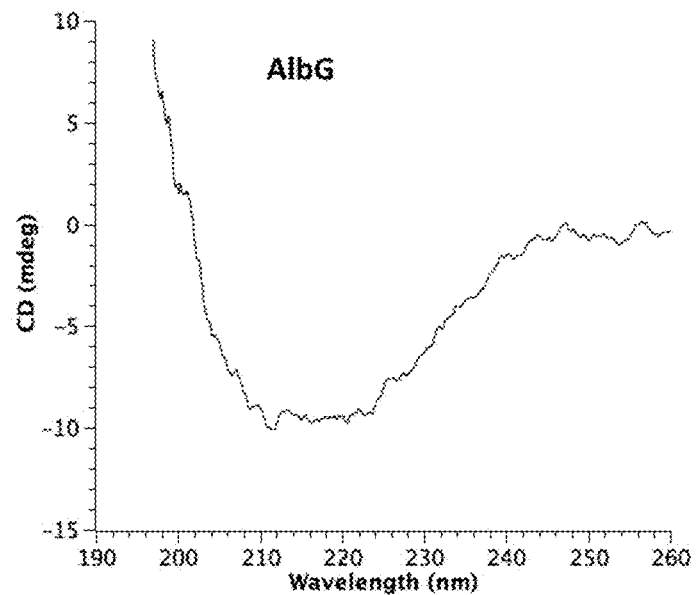
FIG. 1 shows the CD (circular dichroism) spectra of the isolated AlbG protein, in accordance with the present disclosure.

FIG. 1 displays the CD spectra of purified AlbG protein (SEQ ID NO: 1) used for the study. Protein was dialyzed in PBS and 1-5 micromolar concentration was used to measure the CD spectroscopy in 200-300 nm region. Further dilution was done with PBS wherever needed. The negative value of CD at 220 nm for this protein indicates arrangement of β sheets (β barrel or β helical structures).

Figure 2:
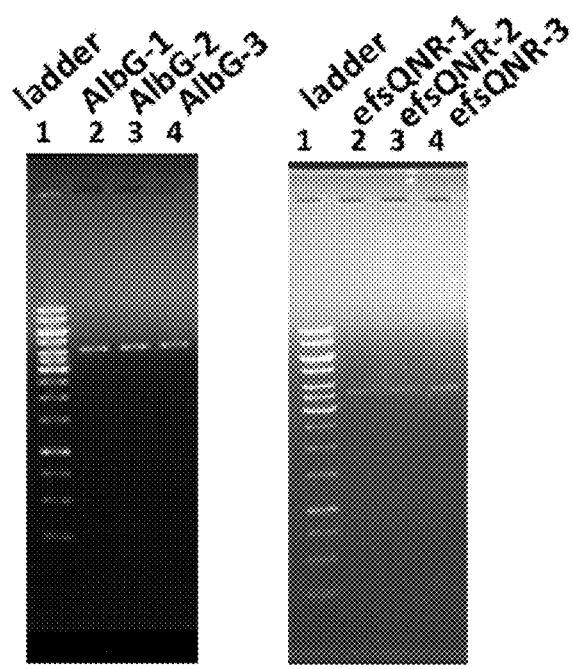
FIG. 2 shows an agarose gel containing purified plasmids (containing AlbG and EfsQNR genes), in accordance with the present disclosure.

FIG. 2 shows the purified plasmids used for expressing β helical proteins, AlbG and EfsQNR, each showing identical results in triplicate (AlbG-1 to AlbG-3 and EfsQNR-1 to EfsQNR-3).

Figure 3:
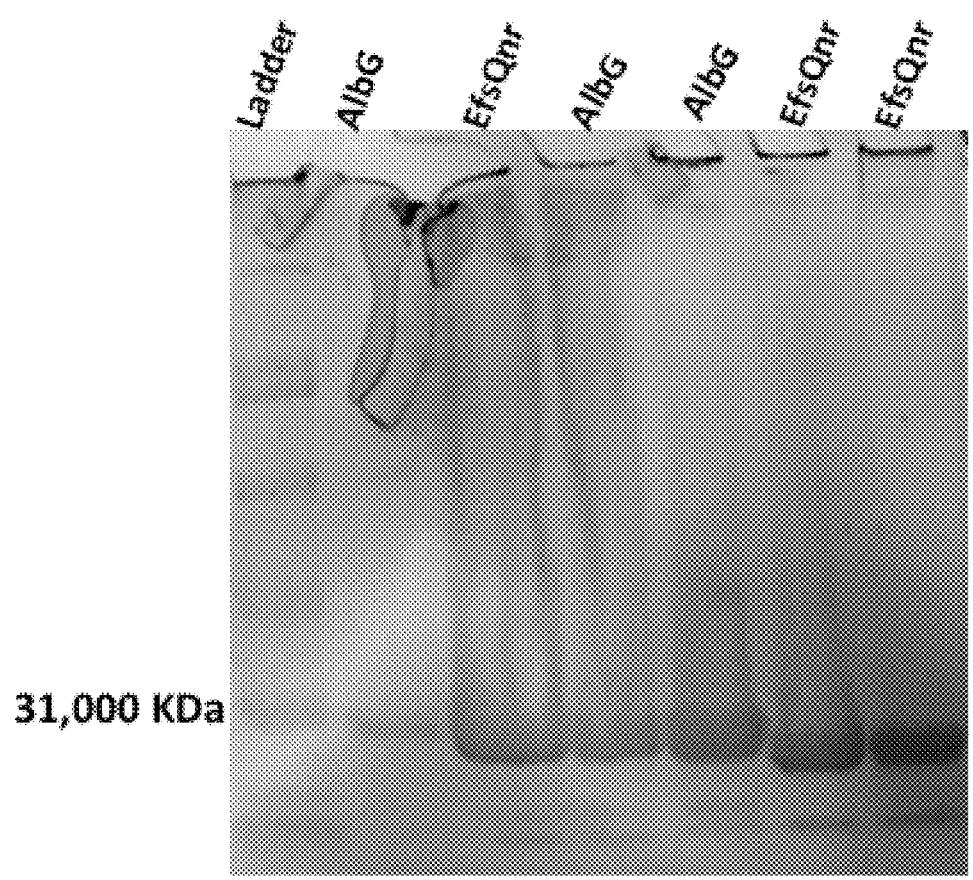
FIG. 3 shows a poly-acrylamide gel containing purified proteins (AlbG and EfsQNR), in accordance with the present disclosure.

FIG. 3 shows the purified protein bands of the AlbG and EfsQNR proteins in a polyacrylamide gel. After performing SDS-gel electrophoresis, it was noted that molecular weight of both the proteins in monomer forms were approximately 30 kDa. The approximate molecular weight in dimer forms of AlbG and EfsQNR is around 48 kDa. The proteins, AlbG and EfsQNR were used to form a conjugate with a functional molecule, which was then used to study the cell penetrating efficacy. The proteins were further tested for any cytotoxicity using Hela cells for determining the course of study (see "Cytotoxicity Studies" below).

Figure 4:
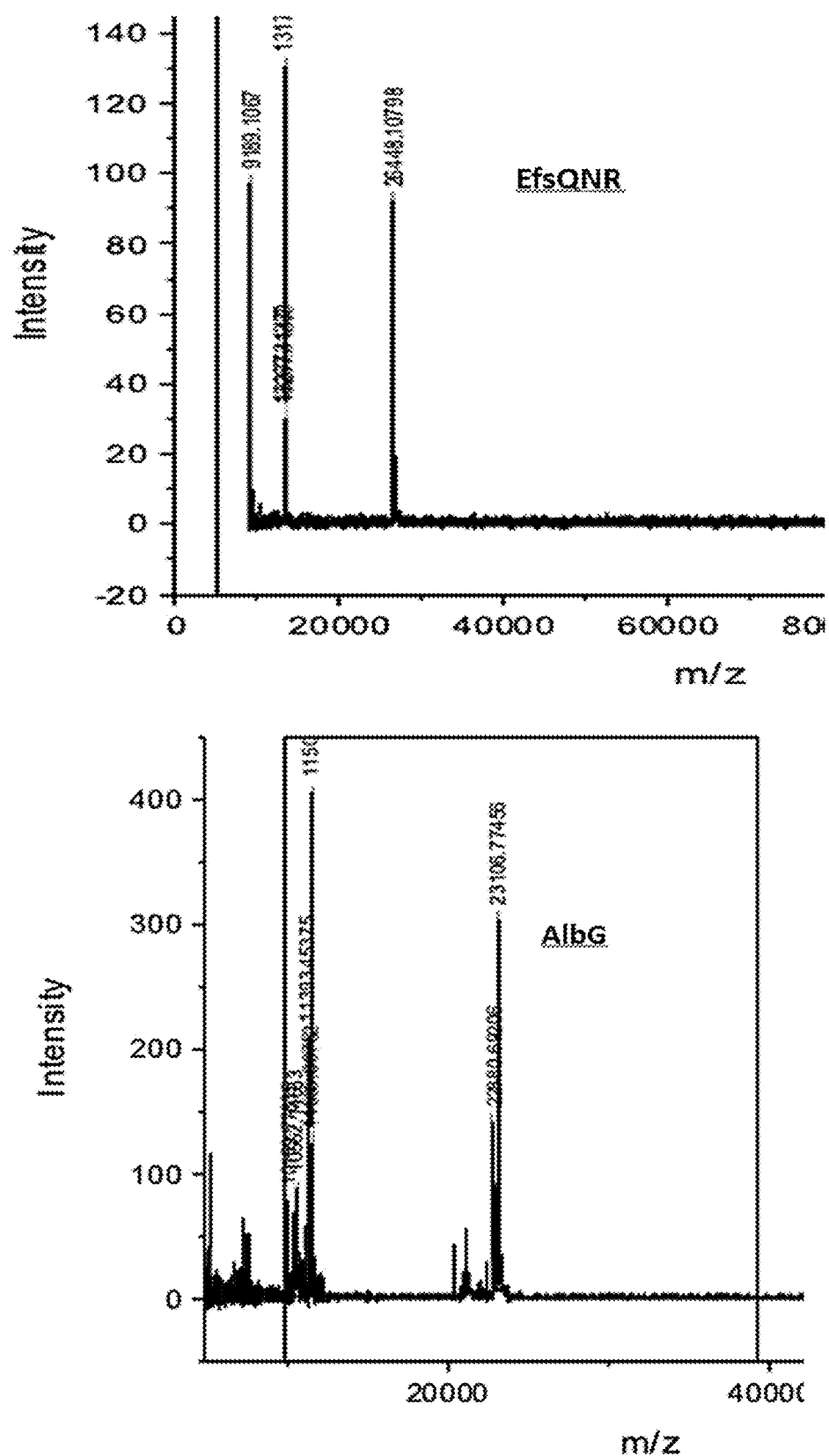
FIG. 4 shows MALDI-TOF mass spectral analysis of the EfsQNR and AlbG proteins.

FIG. 4 shows the result of a MALDI TOF mass spectrometry analysis of the EfsQNR protein and the AlbG protein. For this experiment, the protein was dialyzed in water and sample was prepared using sinapic acid as matrix with 0.1% TFA and acetonitrile. 1-10 micromolar of protein was used. The results show the EfsQNR protein having a molecular weight of approximately 26.5 kDa, and the AlbG protein having a molecular weight of approximately 23 kDa.

Cytotoxicity Studies

MTT assay as described previously was employed to study toxicity of AlbG and EfsQNR proteins against HeLa cells. For the toxicity assay, samples of Placebo, control, AlbG (30 μM) and EfsQNR (30 μM) were used in triplicates. Table 1 depicts the absorbance values at 570 nm of each sample after treatment with MTT. On observing the values, it can be appreciated that the cells treated with 30 μM of AlbG and 30 μM of EfsQNR display 95% viability as compared to the control cells. This clearly suggests that the tested protein at the tested concentration is not toxic for HeLa cells and hence is a safe concentration to use in further experiments.

Table 1 presented here depicts the absorbance values at 570 nm in MTT assay for evaluating toxicity of the proteins:

TABLE 1

| 1 | 2 | 3 | 4 | 5 | 6 | 7 | 8 | 9 | 10 | 11 | 12 |
|---|---|---|---|---|---|---|---|---|----|----|----|
| PLACEBO | | | CONTROL | | | EfsQNR | | | AlbG | | |
| 0.049 | 0.05 | 0.046 | 1.341 | 1.348 | 1.413 | 0.901 | 1.111 | 0.971 | 1.002 | 1.03 | 0.932 |

The placebo for this experiment was 20 mM Tris buffer of pH 8.0, whereas, the control considered was only HeLa cells without adding any protein or other substrate.

Labelling Studies

FIG. 4 shows the UV-visual spectrophotometry of the labelled AlbG and EfsQNR conjugates by the procedure as mentioned previously (see "Labelling of proteins with fluorescent dyes" above). The UV-visual spectra was analysed to calculate the labelling ratio of both conjugates. The labelling ratio signifies the number of dyes attached per protein molecule. This is calculated by measuring the ratio between the absorbance values of the dye (at a wavelength depending on the dye used for labelling) and the absorbance of the protein at 280 nm. The dye used for labelling in this experiment was NHS-coumarin. In case of AlbG protein, the dye: protein molecule ratio is observed to be 1.95. In case of EfsQNR the dye: protein molecule ratio is found to be 5.5. The UV-vis spectra confirmed the labelling of both AlbG and EfsQNR proteins with NHS-coumarin dye. The labelled proteins were further used to establish cell penetration in this study.

Cellular Penetration Studies

Figure 5:
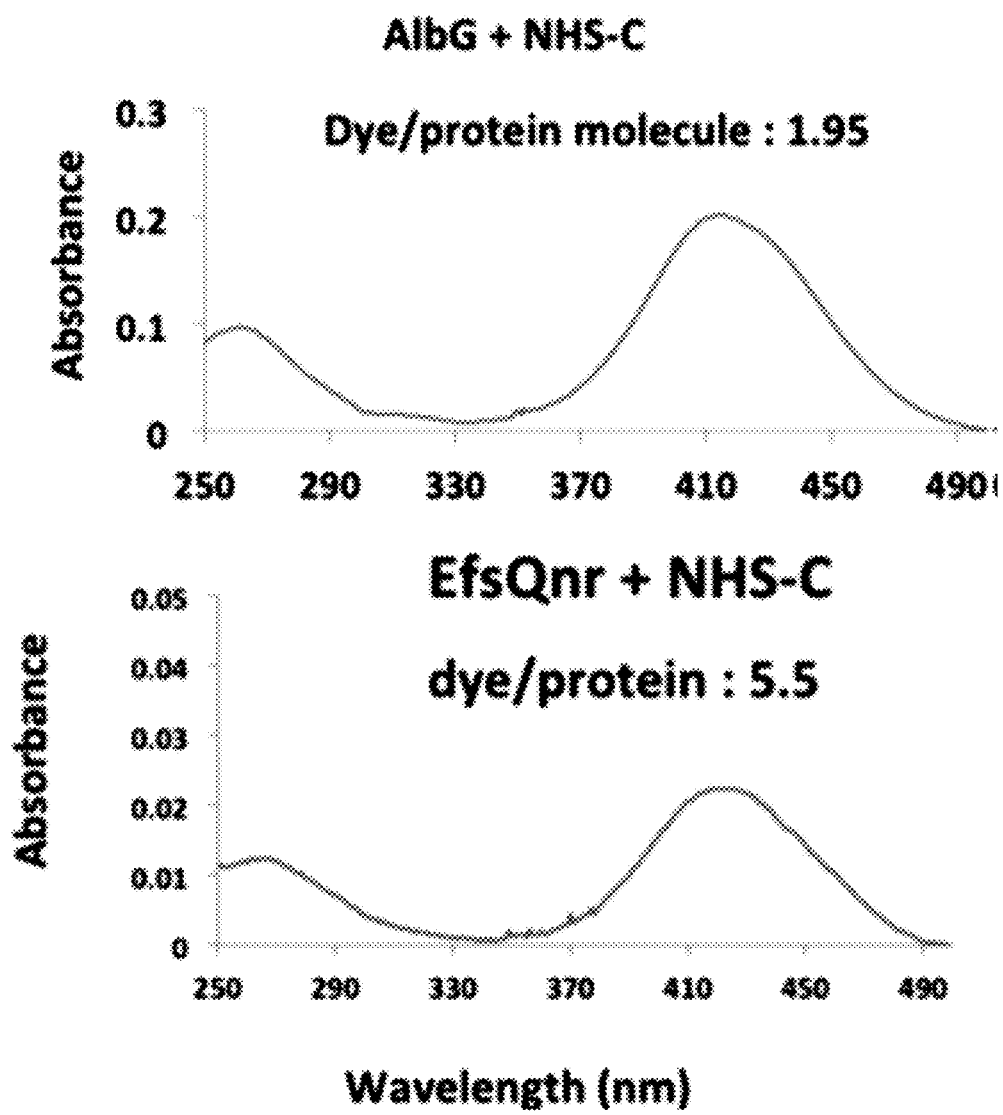
FIG. 5 shows the graphical representation of characterization of labelled proteins (AlbG-NHSC and EfsQNR-NHSC) by UV-visible spectrophotometry, in accordance with an embodiment of the present disclosure.

FIG. 5 shows the fluorescence microscopic images of HeLa cells treated with NHS-C labelled AlbG, EfsQNR, and TtCuA protein (conjugates). The intake of the labelled proteins (conjugates) was compared with the untreated HeLa cells which were considered as a control set for this study. Hoechst Blue is a nuclear labelling dye used along with NHS-C dye which is used for labelling the proteins. The proteins AlbG and EfsQNR are β helical proteins of length in the range of 5 nm-25 nm, suitably, 10 nm-15 nm and width is in the range of 1 nm-5 nm, suitably 1 nm-3 nm representing the recombinant β helical protein of the present invention. However, TtCuA is a protein of length around 4 nm and is composed of β strands forming β barrels, thereby representing a comparative example for the recombinant β helical protein of the present invention. These two different categories of proteins were considered for this study to establish the superior cell penetrating ability of the conjugate of the present invention as compared to different type of β helical protein.

In FIG. 5, panel A represents the control cells which are treated only with nuclear labelling dye (Hoechst Blue) signifying the lack of lighter dye, panel B represents the cells treated with Hoechst Blue dye and with TtCuA-NHSC labelled protein (conjugate), panel C represents the cells treated with Hoechst Blue dye and AlbG-NHSC labelled protein (conjugate) and panel D represents the cells treated with Hoechst Blue dye and EfsQNR-NHSC labelled protein (conjugate). On observing the figure, it can be appreciated that significantly less fluorescence can be seen inside the cells as shown in panel B signifying less presence of TtCuA-NHSC conjugate inside these cells, whereas greater fluorescence can be seen inside the cells represented in panel C and panel D signifying larger presence of AlbG-NHSC conjugate and EfsQNR-NHSC conjugate inside the cells. Therefore, it can be appreciated that TtCuA-NHSC conjugate is not able to effectively penetrate the cell membrane to gain entry inside cells as compared to AlbG-NHSC conjugate and EfsQNR-NHSC conjugate.

On comparing panels C and D, it can be observed that EfsQNR-NHSC conjugate is able to penetrate the membrane more efficiently as compared to the AlbG-NHSC conjugate. Therefore, the cell penetration ability of the three conjugates can be summarised in an increasing order of cell uptake as TtCuA-NHSC<AlbG-NHSC<EfsQNR-NHSC. This further proves the cell penetrating ability of the conjugate comprising a recombinant β helical protein of length and breadth in the range of 5 nm-25 nm, suitably, 10 nm-15 nm and width is in the range of 1 nm-5 nm, suitably 1 nm-3 nm respectively. The conjugates independently comprising AlbG and EfsQNR are able to show enhanced cell permeability as compared to the conjugate comprising TtCuA.

Since the conjugate comprising EfsQNR protein displayed the highest ability to penetrate cell membrane, EfsQNR protein was further studied with different dyes for enhanced labelling of mammalian cells.

FIG. 22 shows in real-time cell entry proceeding via direct interaction of the conjugate with the cell-membrane. To visualise the cells under fluorescence microscopy they were treated with the dye Hoechst 33342 (blue, appearing dark in in FIG. 22) which binds to the nucleus and the dye Alexa 594-WGA (red, appearing lighter in in FIG. 22) which binds to the plasma membrane indicating that the EfsQNR-ATTO-520NHS (green, appearing as light circles in FIG. 22) efficiently penetrates inside the cell by a direct mechanism avoiding any endocytotic mechanism.

Labelling of Mammalian Cells

Figure 6:
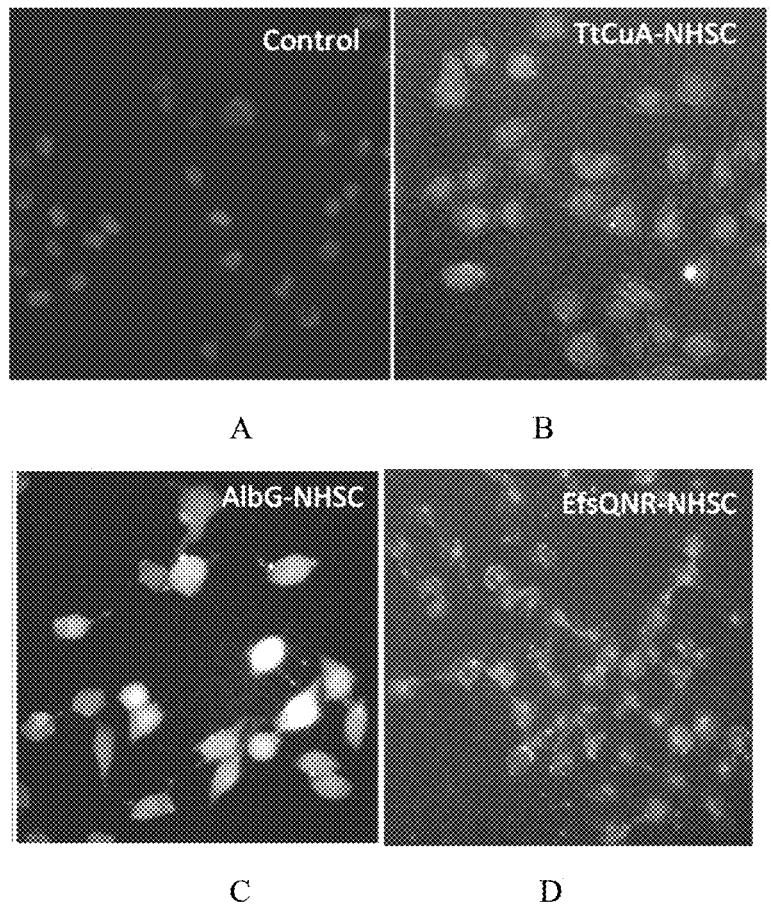
FIG. 6 shows differential labelling of Hela cells by labelled proteins (conjugates) AlbG-NHSC, EfsQNR-NHSC and TtCuA-NHSC, in accordance with embodiments of the present disclosure.

FIG. 7 depicts the ability of a conjugate comprising EfsQNR conjugated with a dye in labelling of HeLa cells. FIG. 6 depicts the cells labelled with EfsQNR-ATTO-520NHS prepared according to the method of labelling above. The dye Hoechst 33342 (blue, appearing dark in in FIG. 7) binds to the nucleus and the dye Alexa 594-WGA (red, appearing lighter in in FIG. 7) binds to the plasma membrane. The conjugate is formed by linking EfsQNR protein with a green fluorescent dye ATTO-520NHS (appearing as the lightest dye in FIG. 7). It can be clearly observed that the EfsQNR-ATTO-520NHS conjugate penetrates the HeLa cells to lead to efficient labelling (Panel B) of the cells when compared to the control panel A showing HeLa cells which are not treated with the conjugate.

FIG. 8 depicts a similar result for HeLa cells treated with the conjugate formed by linking EfsQNR protein with a blue fluorescent dye ATTO-390NHS (appearing lighter in FIG. 8)

FIG. 9 depicts a similar result for microglial cells labelled with the EfsQNR-ATTO-520NHS which was prepared according to the method of labelling above. Panel A shows significant fluorescence of the dye from inside the cells. Panel B shows microglial cells additionally treated with the dye Hoechst 33342 (blue, appearing dark in in FIG. 9) which binds to the nucleus and the dye Alexa 594-WGA (red, appearing lighter in in FIG. 9) which binds to the plasma membrane indicating that the EfsQNR-ATTO-520NHS has efficiently penetrated inside the cell.

FIG. 10 depicts a similar result for keratinocyte cells labelled with the conjugate EfsQNR-ATTO-520NHS which was prepared according to the method of labelling above. Panel A shows significant fluorescence of the dye from inside the cells. Panel B shows keratinocyte cells additionally treated with the dye Hoechst 33342 (blue, appearing dark in in FIG. 10) which binds to the nucleus indicating that the EfsQNR-ATTO-520NHS has efficiently penetrated inside the cell to be present near the nucleus.

FIG. 11 depicts a similar result for SH-SY5Y cells labelled with the conjugate EfsQNR-ATTO-520NHS which was prepared according to the method of labelling above.

FIG. 12 depicts a similar result for Mouse ES cells labelled with the EfsQNR-ATTO-520NHS which was prepared according to the method of labelling above. FIG. 12 shows Mouse ES cells treated with the dye Hoechst 33342 (blue, appearing dark in in FIG. 12) which binds to the nucleus and the dye Alexa 594-WGA (red, appearing lighter in in FIG. 12) which binds to the plasma membrane indicating that the EfsQNR-ATTO-520NHS has efficiently penetrated inside the cell.

Labelling of Non-Mammalian Cells

FIGS. 13 to 14 and 21 to 28 depict the ability of a conjugate comprising EfsQNR conjugated with a dye in labelling of bacterial cells (*E coli* and *Pseudovibrio* AD37), yeast cells (*kluveromyces* and *Sachromyces* sp.), plant cells (*Arabidopsis* sp.), Insect cells (*Drosophila* embryo) and fish cells (Zebra fish embryo). FIGS. 13 to 14 and 21 to 28 depict respectively *E coli*, *Pseudovibrio* AD37, *kluveromyces*, *Sachromyces* sp., *Arabidopsis* sp., *Drosophila* embryo and Zebra fish embryo cells labelled with EfsQNR-ATTO-520NHS prepared according to the method of labelling above.

FACS Sorting of HeLa Cells Treated with the Conjugate

FIG. 15 shows the results of standard FACS sorting of Hela cells treated with a conjugate labelled with the conjugate EfsQNR-ATTO-647N. Treatment of cells for only 10 minutes (Panel B) leads to significant uptake of the dye compared to the control (Panel A) which continues to increase at 1 h (Panel C) up to the measured 3 h maximum (Panel D).

Drug Uptake Studies

FIG. 16 depicts the cellular uptake of the ruthenium metal complex $Ru(CO)_3Cl$ glycinate in HeLa cells. The ruthenium metal complex was conjugated with EfsQNR protein to form a conjugate consisting of ruthenium metal complex-EfsQNR. The HeLa cells were treated with the ruthenium metal complex-EfsQNR conjugate as described above (see "Cellular penetration studies" above) and uptake of the complex was detected by checking the viability of the cells by performing MTT assay as described previously. On observing the graph (FIG. 14), it can be appreciated that upon treatment with only ruthenium metal complex, the cellular uptake is only 0.5%, whereas upon treatment with ruthenium metal complex-EfsQNR protein conjugate the cellular uptake of the complex increases to 24.4%. Therefore, it can be ascertained that the conjugate comprising EfsQNR protein facilitated 50-fold higher cellular uptake as compared to ruthenium metal complex alone. This enhanced uptake can be further exploited by using the conjugate of the present invention to deliver many life-saving drugs to the target thereby reducing the dose of the drug and subsequently decreasing the side-effects.

FIG. 17 shows the results of a viability study of mammalian cells (HeLa and HepG2) cultured with a conjugate comprising EfsQNR protein linked to the chemotherapy drug, Cisplatin® (cisplatinum or cis-diamminedichloroplatinum (II) (CDDP)) labelled 'CYDD' in FIG. 17. Mammalian cells (HeLa: Panel A; or HepG2: Panel B) were cultured by using standard protocol. One million cells were seeded in confocal plates (1 cm dish), grown for 8 h. A conjugate comprising Cisplatin® and EfsQNR (prepared in accordance with the method described above in a molar ratio of 2:1) was then added and the culture kept at room temperature for 15 minutes. The cells were kept under standard growth condition for 24 h and 72 h. Then the cells were washed with PBS and MTT solution was added. After the formazan dyes are formed it was dissolved in DMSO and absorbance at 550 nm was measured. It is apparent from the results that in both cell types tested similar cytotoxic efficacy of Cisplatin® is demonstrated with a lower dose when the drug is delivered as a conjugate in accordance with the present invention.

It is noted that in all experiments where tested, similar results were obtained when the EfsQNR protein was replaced with the AlbG protein.

Advantages

Overall, it can be concluded that a conjugate comprising a recombinant β helical protein of specific length and width, and a functional molecule can act as a highly efficient cell membrane penetrating conjugate. The ability of the conjugate to directly penetrate the cell membrane provides advantages as compared to the endocytotic entry mechanism. Working examples of the AlbG-NHSC and EfsQNR-NHSC conjugates are provided in the present disclosure which demonstrate their ability to penetrate the cell membrane. The EfsQNR-dye conjugate is shown to enhance the ability of labelling of a variety of mammalian and non-mammalian cells because of its ability to effectively penetrate the cell membrane. The conjugate comprising EfsQNR and/or AlbG has been shown to increase the cellular uptake of drugs including ruthenium metal complexes and Cisplatin® in HeLa and HepG2 cells. This ability can be further exploited to elevate the uptake of different anti-cancer drugs by cancer cells which can facilitate the treatment by selectively targeting the cancerous cells in an efficient manner and simultaneously with a reduced requirement of the drug. Reduction in the dose of anti-cancer drug can also circumvent the side-effects associated with administration of such drugs.

EXAMPLES—Cell Penetrating Molecule with Nucleic Acid

In the following paragraphs, working examples have been provided for delivering a nucleic acid, such as a plasmid, having a gene of interest inside the cell by penetrating the cell membrane. The delivery is made possible because of the use of a conjugate (a cell penetrating peptide as described herein), further comprising a nucleic acid molecule or plasmid. The examples also depict the expression of the gene of interest after penetrating the cell membrane to enter inside the cell.

A first example describes transfection of a gene of interest into a cell using an embodiment of the conjugate of the present invention, wherein the gene of interest is mcherry coding for RFP (Red Fluorescent Protein). The plasmid containing mcherry gene is linked to a protein to form a conjugate, wherein the conjugate comprises EfsQNR protein and copper [II] phenanthroline. The conjugate is used to transfect HeLa cells. The successful expression of mcherry gene in HeLa cells is shown as a proof-of-concept to establish the ability of the conjugate to penetrate the cell membrane and transfect the cells.

Material and Methods

Copper phenanthroline complex was commercially procured.

Example 6

Protein studies—Studies governing the expression of EfsQNR plasmid, conditions of incubation, and purification were followed as published previously (Hegde et al. Antimicrob. Agents and Chemother. 2011: 55(1): 110-7 which is incorporated herein by reference) to obtain EfsQNR protein. The SDS-PAGE (polyacrylamide gel electrophoresis) was done using the Bio-Rad kit and the protein bands were visualised using 12% polyacrylamide gel.

Example 7

Preparation of a Plasmid Conjugate—Copper [II] Phenanthroline Linkage

As is disclosed in the present invention, a conjugate is prepared for transfecting cells, the conjugate comprising EfsQNR (SEQ ID NO: 2), copper [II] phenanthroline, and a plasmid having a gene of interest.

FIG. 18 depicts a vector map of plasmid carrying mcherry gene (SEQ ID NO: 25), used in preparation of the conjugate in the present example. EfsQNR protein (SEQ ID NO: 2) is a β helical protein having a pentapeptide repeat (as depicted in SEQ ID NO: 18) having length in the range of 5 nm-25 nm, suitably, 10 nm-15 nm and width is in the range of 1 nm-5 nm, suitably 1 nm-3 nm. Copper [II] phenanthroline is a nucleic acid intercalating agent used as a linker in the present example.

EfsQNR protein obtained by governing the expression of EfsQNR plasmid was complexed with copper [II] phenanthroline complex to obtain a complex comprising EfsQNR and copper [II] phenanthroline. The obtained complex was further reacted with plasmid having mcherry gene to obtain a conjugate in accordance with an embodiment of the present invention. The obtained conjugate was used to transfect HeLa cells.

FIG. 19 depicts two schemes for preparing the conjugate that can be used for transfection. Scheme 1 suggests the use of copper [II] phenanthroline as a linker which forms a complex with a protein. The obtained complex is further reacted with a plasmid having a gene of interest to obtain the conjugate to be used for transfection.

Scheme 2 suggests the use of a DNA binding protein as a linker which forms a complex with a protein. The obtained complex is further reacted with a plasmid having a gene of interest to obtain the conjugate to be used for transfection.

In the present example, copper [II] phenanthroline is used as a linker to form a complex and a recombinant β helical protein—EfsQNR (SEQ ID NO: 2) is used along with a plasmid containing mcherry gene. The following protocol was used for preparing the complex and the conjugate:

The protein EfsQNR was mixed with copper [II] phenanthroline in a 1:2 molar ratio and incubated for 30 minutes as room temperature to obtain the complex. Plasmid containing mcherry gene was mixed with the complex obtained in previous step and incubated for 30 minutes at 4° C. to obtain the conjugate. The conjugate so obtained was used to transfect HeLa cells.

Example 8

Transfection of HeLa Cells Using the Conjugate of Example 7

FIG. 20 depicts a scheme for transfection experiment using the conjugate obtained in Example 7. In the present example following conditions were used for performing the transfection experiment.

The conjugate comprising the mcherry plasmid as obtained in Example 7 (A) was added to HeLa cells (8 hours after seeding). The cells were allowed to grow by incubating at 37° C. and 5% $CO_2$ conditions for 48 hours. After the incubation, the cells were observed under confocal microscopy.

FIG. 21 depicts confocal microscopy images of Hela cells after the transfection experiment. The expression of RFP can be observed as lighter (red) dots inside the HeLa cells thereby, proving the cell penetration and transfecting ability of the conjugate disclosed in the present document.

Example 9

Preparation of a Plasmid Conjugate—Ethylene Diamine Linkage

As is further disclosed in the present invention, a conjugate was prepared for transfecting cells with a plasmid typical for encoding for one or more gene editing molecules. The conjugate comprised EfsQNR (SEQ ID NO: 2), an ethylene diamine linker, and a plasmid. The conjugate was prepared in accordance with a known protocol (Ref: Bioconjugate Techniques; Greg T. Hermansen; Academic Press;

3rd edition; 2013; pp 264-265) which is incorporated herein by reference). The plasmid used was a red labelled circular plasmid DNA of 2.7 kb (Label IT® Plasmid Delivery Control Cy®3 (Product code MIR 7904), obtained from Mirus Bio).

Example 10

Transfection of MCF7 Cells Using the Conjugate of Example 9

The conjugate comprising the plasmid [Label IT® Plasmid Delivery Control Cy® 3 (Product code MIR 7904) as obtained in Example 9 was added to MCF-7 cells (8 hours after seeding). The cells were allowed to grow by incubating at 37° C. and 5% $CO_2$ conditions for 12-16 hours. After the incubation, the cells were observed under confocal microscopy.

FIG. 30 shows the results for a transfection experiment in MCF7 cells using (A) the conjugate obtained in Example 1 (EfsQNR) (SEQ ID NO: 2) and a red labelled circular plasmid DNA of 2.7 kb, commercially obtained from Mirus Bio (product code MIR 7904) and (B) control red labelled plasmid as used above in the absence of conjugate. (i) shows the maximum projection of the cells after incubation; (ii) image corresponding to the intensity plots of the cells after incubation; and (iii) shows the intensity plots of the cells after incubation.

In the maximum projection images (i), it can be clearly seen that the plasmid is able to spread throughout the cell far better when conjugated to the EfsQNR protein. This shows the efficiency of conjugate to carry and localize target nucleic acids, such as plasmids, in the cells.

From the intensity plots (iii) it is clear that the plasmid was able to enter the cells by the aid of protein and the spread is homogenous and widespread.

Although the examples as presented herein show the use of protein EfsQNR (SEQ ID NO: 2) in the preparation of a conjugate for transfection, the proteins having amino acid sequence as depicted in SEQ ID NO: 1 and SEQ ID NO: 3 to SEQ ID NO: 12 can also be used effectively to form the conjugate. Also, recombinant β helical proteins having a penta-peptide repeat sequence as depicted in SEQ ID NO: 18 and having a length in the range of 5 nm-25 nm, suitably, 10 nm-15 nm and width is in the range of 1 nm-5 nm, suitably 1 nm-3 nm can be used for preparing the conjugate as described in the present disclosure. Similarly, the present example depicts the use of copper [II] phenanthroline or ethylene diamine as a linker but other molecules like DNA binding protein, metal conjugate, drug metal conjugate, and other nucleic acid intercalating molecule can also be used in the formation of a conjugate to be used effectively as a transfecting agent. One class of a DNA binding protein namely, zinc finger protein having a molecular weight of less than 12 kDa can also be used to form the conjugate. One such zinc finger protein that can be used as a linker has been depicted in SEQ ID NO: 24. In the present disclosure, a plasmid (FIG. 18) carrying mcherry gene, and a red labelled circular plasmid DNA of 2.7 kb has been used for preparing conjugates for transfection, and the expression of mcherry gene, has been shown as a proof-of-concept. It is contemplated that essentially any nucleic acid or plasmid comprising a gene of interest for transfection purpose can be complexed with the complex as disclosed herein to form the conjugate for use in gene therapy or gene editing.

Advantages

The present disclosure provides with a conjugate comprising a nucleic acid or plasmid comprising a gene of interest which possess the ability of penetrating cell membrane and expressing the gene of interest. Hence, the conjugate can be used for transfection and has immense potential to be used in gene therapy and gene editing. As is known that delivery of nucleic acids and plasmids comprising the gene to the cells is a major challenge in the field of gene therapy and gene editing, the disclosed conjugate opens new avenue in this field. The disclosed conjugate is simple to prepare and can be complexed with wide variety of nucleic acids and plasmids comprising genes to be used for gene therapy and gene editing.

Example 11

Transfection of Gene Editing Molecular Machinery with a CPP of the Present Invention A transfection experiment was conducted in mammalian cells using the conjugate obtained in Example 1 (EfsQNR: SEQ ID No. 2) and a gene editing complex, CRISPR-RNP based on the endonuclease Cas9. The results provided in Table 2 are depicted in FIG. 29. It is contemplated based on the results of Example 4 above that application of the technique is applicable a wide variety of cells, including bacteria cells, yeast cells, plant cells, insect cells and fish cells.

TABLE 2

| Control | CRISPR-RNP-CPP in PBS | CRISPR-RNP-CPP in reaction buffer |
|---|---|---|
| 1 | 0.99 | 0.9 |
| 1 | 0.94 | 0.7 |

In an embodiment of the present invention, the following conditions were used for performing the transfection experiment.

Strategy: Gene editing in cells has been reported via a number of different methods. One particularly relevant example delivers the ribonucleoprotein (RNP) complex of the endonuclease, such as Cas9, and gRNA into cells. This methodology is particularly attractive as no intermediate intra-cellular synthesis of the gene editing machinery is required.

Currently several methods such as electroporation, microinjection, nanoparticles and cationic lipid mediated delivery are used to introduce the gene editing machinery into the cytoplasm of the cell, from where it can migrate to the genome.

In an embodiment, the present invention uses electrostatic interactions between Cas9, gRNA and CPP to carry the Cas9-gRNA RNP (CRISPR-RNP) into the cells. The use of a conjugate wherein the various components are linked by covalent and/or non-covalent interactions is also contemplated.

Cells (HEK 293) expressing eGFP are transfected with CRISPR-RNP that has gRNA specific to eGFP. Uptake of the CRISPR-RNP will be mediated by the CPP of the present invention, which can transport cargo efficiently into cells (Example 4). Following cellular uptake, either dissociated from, or uninhibited by the CPP, the Cas9 will be directed by the gRNA to its target DNA sequence eGFP. Knockout of this gene, and thus loss of fluorescence in cells is evidence of an efficient and effective delivery method for the gene editing complex.

To obtain a stable eGFP expressing cell line, a selection process using the G418 antibiotic is used. Cells expressing eGFP, and thus having taken up the eGFP plasmid, will also confer G418 antibiotic resistance. Cells which have not taken up the eGFP plasmid, do not have resistance to G418 and thus over a period of time will die when kept in selection media.

Experimental: Cells (HEK 293) expressing eGFP (enhanced Green Fluorescent Protein) are obtained by transfecting HEK293 cells with eGFP by using lipofectamine based commercial reagents. The cells are grown for 48 hours to obtain 70-80% cells transfected by the eGFP. The cells are sub-cultured and grown in selection media containing G418 antibiotic to make the HEK 293 cells stably expressing eGFP before using it for the gene editing experiments.

Approximately 5000 cells are seeded into 96 well plate and grown overnight on day 1.

On day 2 the Cas9-gRNA-CPP (CRISPR-RNP-CPP) complex was formed in two steps:

Step 1: Cas9 was mixed with gRNA in i) phosphate buffer saline (PBS) or ii) in the reaction buffer that was supplied with the commercially available Cas9 (Genaxxon Biosciences: Cas9-NLS-tagRFP Streptococcus (S.) pyogenes Cas9 protein NLS followed by a C-terminal red-fluorescent protein (tagRFP) tag sequence; Product number: S5306.0010; HS-No.: 35040090). The reaction buffer acts to stabilize the Cas9 and RNP complex. The mixture was then incubated at room temperature for 25 minutes to form the CRISPR-RNP complex;

Step 2:1 microM CPP in PBS was added to the Cas9-gRNA mixture obtained in step 1 and incubated at room temperature for another 30 minutes to form the CRISPR-RNP-CPP complex;

Step 3: The CRISPR-RNP-CPP complex obtained in step 2 is added to the cells in media (Dulbecco's Modified Eagle Medium (DMEM), with or without serum; ex. Sigma) and the cells are cultured for 4 h. After 4 h, media (DMEM with serum) was added to the cells and left growing under standard cell growth condition (37° C. temperature and 5% $CO_2$) for 48 h. After 48 h the cells were washed with PBS and fresh medium (DMEM with serum) was added and fluorescence intensity due to eGFP was measured in a fluorescence plate reader.

Results in Mammalian Kidney HEK293 Cells

The CPP of the present invention assists in the delivery of CRISPR-RNP into the cell efficiently. Following cellular uptake, the Cas9 is directed by the gRNA to its target DNA sequence of eGFP. Knockout of this gene by Cas9 lead to loss of fluorescence in cells.

Use of a serum free media in step 3 and a reaction buffer in step 1 (as provided in the commercial source for dissolving Genaxxon Cas9 and gRNA; Product no. S5306.0010) resulted in a 30% reduction in fluorescence indicating efficient transfer of the CRISPR-RNP to the interior of the cell.

When PBS (phosphate buffer saline) is used to dissolve the CRISPR-RNP complex no significant change in fluorescence intensity was observed.

Without wishing to be bound by theory, it is postulated that PBS is not able to stabilize the complex formation between CRISPR-RNP and the CPP.

Example 12

Transfection of Fluorescently Labelled Endonuclease Cas9 with a Recombinant β-Helical Protein of the Present Invention FIG. 31 depicts results for a transfection experiment in MCF-7 cells using the conjugate obtained in Example 1 (EfsQNR: SEQ ID No. 2) and the endonuclease cas9, tagged with either (i) red fluorescent protein, or (ii) the green fluorescent dye Atto520.

The conjugate obtained in Example 1 (EfsQNR: SEQ ID No. 2) was mixed with cas9 (ex. Eupheria Biotech) conjugated with either red fluorescent protein or green fluorescent dye ATTO 520 (Sigma product 77810) in 1:1 ratio and incubated at room temperature for 30 minutes.

The solution obtained was added to the cells and incubated with the cells for 12-16 h.

FIG. 31 shows (A) the maximum projection of the cells after incubation; (B) the intensity plots of the cells after incubation; and (C) the 3D depth images of cells after incubation.

In both the maximum projection images (A), it can be clearly seen that cas9 is successfully transfected and able to spread throughout the cell irrespective of the labelling dye. This shows the efficiency of conjugate of the present invention to carry and localize target proteins in the cells.

From the intensity plots (B) it is clear that cas9, irrespective of the companion dye, was able to enter the cells through use of the conjugate. The spread is throughout the cell and homogenous.

The 3D depth images (C) shows that the Cas9 cargo is spread throughout the cell. The depth analysis and 3D representation has shown it is present in all the planes.

Example 13

Transfection of Fluorescently Labelled gRNA with a Recombinant β-Helical Protein of the Present Invention As is further disclosed in the present invention, a conjugate was prepared for transfecting cells with a gRNA typical for use in gene editing with the CRISPR-cas9 gene-editing system. The conjugate comprised EfsQNR (SEQ ID NO: 2), an ethylene diamine linker, and a gRNA (ex. Eupheria Biotech: esiCRISPR Kit-wt) tagged with green fluorescent dye MFP488. The conjugate was prepared in accordance with a known protocol (Ref: Bioconjugate Techniques; Greg T. Hermansen; Academic Press; $3^{rd}$ edition; 2013; pp 264-265 which is incorporated herein by reference).

FIG. 32 depicts results for a transfection experiment in MCF-7 cells using (A) the conjugate obtained in Example 1 (EfsQNR) and the gRNA tagged with the green fluorescent dye MFP488; and (B) control gRNA tagged with the green fluorescent dye MFP488 in the absence of the conjugate. (i) shows the maximum projection of the cells after incubation; (ii) shows 3D depth images of cells; (iii) images corresponding to the intensity plots of the cells after incubation; and (iv) the intensity plots of the cells after incubation.

The images clearly show that the intensity and homogeneity of gRNA inside the cells is significantly less for the control compared to the cells incubated with gRNA and the conjugate. This suggests that the conjugate is able to carry gRNA into the cells. The maximum projection images, intensity plots and 3D depth images for the control shows that most of the gRNA is localized in the cell membrane whereas with the conjugate, distribution is clearly observed mainly in the cytoplasm.

CRISPR components were obtained from two different commercial sources namely Eupheria Biotech and Genaxxon.

Genaxxon Biosciences: GFP-targeting guide RNA for CRISPR; Product number: P2008.0010, Purified gRNA targets sequences encoding enhanced GFP; HS-No.: 29349990).

Genaxxon Biosciences: Cas9-NLS-tagRFP *Streptococcus* (*S.*) *pyogenes* Cas9 protein NLS followed by a C-terminal red-fluorescent protein (tagRFP) tag sequence; Product number: S5306.0010; HS-No.: 35040090).

Eupheria Biotech: esiCRISPR Kit-wt, a kit comprising:
20 µg *Streptococcus pyogenes* Cas9-NLS (650 ng/µl)
15 µg custom guide (g) RNA (400 ng/µl)
35 µl CRISPRfection™ transfection reagent (a proprietary lipid-based transfection reagent suitable for the delivery of single guide (g) RNA-loaded Cas9 proteins into most adherent cells)
1 ml CRISPRfection buffer (diluent for CRISPRfection)
5 µg of NoTarget gRNA (in man, mouse, rat) as a negative control.
Reaction buffers to perform indel analysis of PCR products derived from DNA isolated from transfected cells.
Positive-control reagents to confirm Cas9-NLS protein and gRNA performance: control target DNA, control gRNA, reaction buffers.
Application manual with protocols for transfection, indel analysis, and Cas9 activity assay.
[www.eupheria.com/products/crisprcas9/esicrispr-kits/; accessed 25 Feb. 2019]

Strategies to Confirm that the Cells Still Retain the Plasmid but with Edited Non Fluorescent eGFP A 'm-cherry' construct that expresses both eGFP and RFP—green & red fluorescence. Transfection of mammalian cells with this plasmid will allow us to determine whether cells are expressing eGFP and have successfully been delivered. Cells fluorescing red, but not green would indicate eGFP deletion conferred by gene editing following CRISPR-RNP-CPP delivery.

Strategies to Improve the Cellular Uptake and Gene Editing (Deletion, Replacement or Mutagenesis)

Optimisation of conditions for successful delivery of the CPP-Cas9-gRNA complex may be achieved by a number of strategies:

Strategy 1: It is postulated that a specific tailored buffer may enhance interactions between CPP and CRISPR-RNP. The following variations are contemplated to increase the efficiency of intracellular delivery:
i) Addition of crowding agents (PEG 4000, cholesterol) to promote the complex formation of CRISPR-RNP-CPP;
ii) Addition of specific small lipids (1,2-dioleoyl-3-trimethylammonium-propane, 1-palmitoyl-2-oleoyl-sn-glycero-3-phosphocholine) to promote the complex formation of CRISPR-RNP-CPP by facilitating hydrophobic interactions;
iii) Small molecules like Phorbol 12-myristate 13-acetate (to enhance the micropinocytosis process in cell)
iv) Alteration in pH and ionic strength (to promote the electrostatic interaction between CPP-Cas9-gRNA)

Strategy 2: CPP could be functionalized with 3-(N-succinimidyloxyglutaryl)aminopropyl, polyethyleneglycol-carbamyl distearoylphosphatidyl-ethanolamine and/or N-(aminopropyl polyethyleneglycol)carbamyl-distearoylphosphatidyl-ethanolamine. This functionalization may enhance the interaction of CPP with the lipid molecules of the cell membrane and facilitate the cell entry of the CRISPR-RNP-CPP complex of an embodiment of the present invention.

Strategy 3: it is postulated that the same approach as used with the CRISPR endonuclease may be used with other gene editing endonuclease systems such as ZFNs and TALENS®.

It should be understood that the different embodiments of the invention described herein can be combined where appropriate and that features of the embodiments of the invention can be used interchangeably with other embodiments where appropriate.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention as defined by the claims.

TABLE 3

| List of sequences | |
|---|---|
| SEQ ID | Sequences |
| SEQ ID NO: 1 - Protein | MPAKTLESKDYCGESFVSEDRSGQSLESIRFEDCTFRQCNFTEAEL NRCKFRECEFVDCNLSLISIPQTSFMEVRFVDCKMLGVNWTSAQW PSVKMEGALSFERCILNDSLFYGLYLAGVKMVECRIHDANFTEAD CEDADFTQSDLKGSTFHNTKLTGASFIDAVNYHIDIFHNDIKRARF SLPEAASLLNSLDIELSD |
| SEQ ID NO: 2 - Protein | GSHMKITYPLPPNLPEQLPLLTNCQLEDEAILENHLYQQIDLPNQE VRNLVFRDAVFDHLSLANGQFASFDCSNVRFEACDFSNVEWLSG SPHRVTFLRCNLTGTNFADSYLKDCLFEDCKADYASFRFANFNLV HFNQTRLVESEFFEVTWKKLLLEACDLTESNWLNTSLKGLDFSQN TFERLTFSPNYLSGLKVTPEQAIYLASALGLVIT |
| SEQ ID NO: 3 - Protein | QCTGGADCTSCTGACTGCGNCPNAVTCTNSQHCVKANTCTGSTD CNTAQTCTNSKDCFEANTCTDSTNCYKATACTNSSGCPGH |
| SEQ ID NO: 4 - Protein | GYSCRAVGVDGRAVTDIQGTCHAKATGAGAMASGTSEPGSTSTA TATGRGATARSTSTGRGTATTTATGTASATSNAIGQGTATTTATG SAGGRATGSATTSSSASQPTQTQTITGPGFQTAKSFARNTATTTVT ASHHHHHH |
| SEQ ID NO: 5 - Protein | DGSCTNTNSQLSANSKCEKSTLTNCYVDKSEVYGTTCTGSRFDGV TITTSTSTGSRISGPGCKISTCIITGGVPAPSAACKISGCTFSAN |

TABLE 3-continued

List of sequences

| SEQ ID | Sequences |
|---|---|
| SEQ ID NO: 6 - Protein | GSHMALALVGEKIDRNRFTGEKIENSTFFNCDFSGADLSGTEFIGC QFYDRESQKGCNFSRAMLKDAIFKSCDLSMADFRNSSALGIEIRH CRAQGADFRGASFMNMITTRTWFCSAYITNTNLSYANFSKVVLE KCELWENRWIGAQVLGATFSGSDLSGGEFSTFDWRAANFTHCDL TNSELGDLDIRGVDLQGVKLDNYQASLLMERLGIAVIG |
| SEQ ID NO: 7 - Protein | MIDKSAFVHPTAIVEEGASIGANAHIGPFCIVGPHVEIGEGTVLKSH VVVNGHTKIGRDNEIYQFASIGEVNQDLKYAGEPTRVEIGDRNRIR ESVTIHRGTVQGGGLTKVGSDNLLMINAHIAHDCTVGNRCILANN ATLAGHVSVDDFAIIGGMTAVH QFCIIGAHVMVGGCSGVAQDVPPYVIAQGNHATPFGVNIEGLKRR GFSREAITAIRNAYKLIYRSGKTLDEVKPEIAELA ETYPEVKAFTDFFARSTRGLIR |
| SEQ ID NO: 8 - Protein | MGSSHHHHHHSSGLVPRGSHMDVEKLRQLYAAGERDFSIVDLRG AVLENINLSGAILHGAMLDEANLQQANLSRADLSGATLNGADLR GANLSKADLSDAILDNAILEGAILDEAVLNQANLKAANLEQAILS HANIREADLSEANLEAADLSGADLAIA DLHQANLHQAALERANLTGANLEDANLEGTILEGGNNNLAT |
| SEQ ID NO: 9 - Protein | ATDTGGYAATAGGNVTGAVSKTATSMQDIVNIIDAARLDANGKK VKGGAYPLVITYTGNEDSLINAAAANICGQWSKDPRGVEIKEFTK GITIIGANGSSANFGIWIKKSSDVVVQNMRIGYLPGGAKDGDMIRV DDSPNVWVDHNELFAANHECDGTPDNDTTFESAVDIKGASNTVT VSYNYIHGVKKVGLDGSSSSDTGRNITYHHNYYNDVNARLPLQR GGLVHAYNNLYTNITGSGLNVRQNGQALIENNWFEKAINPVTSR YDGKNFGTWVLKGNNITKPADFSTYSITWTADTKPYVNADSWTS TGTFPTVAYNYSPVSAQCVKDKLPGYAGVGKNLATLTSTACK |
| SEQ ID NO: 10 - Protein | VGTNTGGVLVITDTIIVKSGQTYDGKGIKIIAQGMGDGSQSENQKP IFKLEKGANLKNVIIGAPGCDGIHCYGDNVVENVVWEDVGEDAL TVKSEGVVEVIGGSAKEAADKVFQLNAPCTFKVKNFTATNIGKLV RQNGNTTFKVVIYLEDVTLNNVKSCVAKSDSPVSELWYHNLVVN NCKTLFEFPSQSQIHQY |
| SEQ ID NO: 11 - Protein | QEITVDEFSNIRENPVTPWNPEPSAPVIDPTAYIDPQASVIGEVTIGA NVMVSPMASIRSDEGMPIFVGDRSNVQDGVVLHALETINEEGEPIE DNIVEVDGKEYAVYIGNNVSLAHQSQVHGPAAVGDDTFIGMQAF VFKSKVGNNCVLEPRSAAIGVTIPDGRYIPAGMVVTSQAEADKLP EVTDDYAYSHTNEAVVYVNVHLAEGYKETS |
| SEQ ID NO: 12 - Protein | VGVSGSAEGFAKGVTGGGSATPVYPDTIDELVSYLGDDEARVIVL TKTFDFTDSEGTTTGTGCAPWGTASACQVAIDQDDWCENYEPDA PSVSVEYYNAGTLGITVTSNKSLIGEGSSGAIKGKGLRIVSGAENIII QNIAVTDINPKYVWGGDAITLDD CDLVWIDHVTTARIGRQHYVLGTSADNRVSLTNNYIDGVSDYSA TCDGYHYWAIYLDGDADLVTMKGNYIYHTSGRSPKVQDNTLLH AVNNYWYDISGHAFEIGEGGYVLAEGNVFQNVDTVLETYEGEAF TVPSSTAGEVCSTYLGRDCVINGFGSSGT FSEDSTSFLSDFEGKNIASASAYTSVASRVVANAGOGNL |
| SEQ ID NO: 13 - Protein | AYTLATHTAGVIPAGKLERVDPTTVRQEGPWADPAQAVVQTGPN QYTVYVLAFAFGYQPNPIEVPQGAEIVFKITSPDVIHGFHVEGTNIN VEVLPGEVSTVRYTFKRPGEYRIICNQYCGLGHQNMFGTIVVKE |
| SEQ ID NO: 14 - Peptide | PAAKRVKCD |
| SEQ ID NO: 15 - Peptide | YPYDVPDYAKDEL |
| SEQ ID NO: 16 - Peptide | MLSLRQSIRFFKPATRTLCSSRYLL |
| SEQ ID NO: 17 - Peptide | LSTAADMQGVVTDGMASGLDKDYLKPDD |
| SEQ ID NO: 18 - consensus sequence | $(STAV)_1(DN)_2(LF)_3(STR)_4(G)_5$ |
| SEQ ID NO: 19 - DNA | ATGCCGGCGAAAACCCTGGAAAGCAAAGATTATTGCGGCGAA AGCTTTGTGAGCGAAGATCGCAGCGGCCAGAGCCTGGAAAGC ATTCGCTTTGAAGATTGCACCTTTCGCCAGTGCAACTTTACCGA AGCGGAACTGAACCGCTGCAAATTTCGCGAATGCGAATTTGTG GATTGCAACCTGAGCCTGATTAGCATTCCGCAGACCAGCTTTA TGGAAGTGCGCTTTGTGGATTGCAAAATGCTGGGCGTGAACTG GACCAGCGCGCAGGCGGGCGCGCTGAGCTTTGAACGCTGCATT CTGAACGATAGCCTGTTTTATGGCCTGTATCTGGCGGCGTGA AAATGGTGGAATGCCGCATTCATGATGCGAACTTTACCGAAGC |

TABLE 3-continued

List of sequences

| SEQ ID | Sequences |
|---|---|
| | GGATTGCGAAGATGCGGATTTTACCCAGAGCGATCTGAAAGGC<br>AGCACCTTTCATAACACCAAACTGACCGGCGCGAGCTTTATTG<br>ATGCGGTGAACTATCATATTGATATTTTTCATAACGATATTAAA<br>CGCGCGCGCTTTAGCCTGCCGGAAGCGGCGAGCCTGCTGAACA<br>GCCTGGATATTGAACTGAGCGAT |
| SEQ ID NO: 20 - DNA | GGCAGCCATATGAAAATTACCTATCCGCTGCCGCCGAACCTGC<br>CGGAACAGCTGCCGCTGCTGACCAACTGCCAGCTGGAAGATGA<br>AGCGATTCTGGAAAACCATCTGTATCAGCAGATTGATCTGCCG<br>AACCAGGAAGTGCGCAACCTGGTGTTTCGCGATGCGGTGTTTG<br>ATCATCTGAGCCTGGCGAACGGCCAGTTTGCGAGCTTTGATTG<br>CAGCAACGTGCGCTTTGAAGCGTGCGATTTTAGCAACGTGGAA<br>TGGCTGAGCGGCAGCTTTCATCGCGTGACCTTTCTGCGCTGCAA<br>CCTGACCGGCACCAACTTTGCGGATAGCTATCTGAAAGATTGC<br>CTGTTTGAAGATTGCAAAGCGGATTATGCGAGCTTTCGCTTTGC<br>GAACTTTAACCTGGTGCATTTTAACCAGACCCGCCTGGTGGAA<br>AGCGAATTTTTTGAAGTGACCTGGAAAAAACTGCTGCTGGAAG<br>CGTGCGATCTGACCGAAAGCAACTGGCTGAACACCAGCCTGAA<br>AGGCCTGGATTTTAGCCAGAACACCTTTGAACGCCTGACCTTT<br>AGCCCGAACTATCTGAGCGGCCTGAAAGTGACCCCGGAACAG<br>GCGATTTATCTGGCGAGCGCGCTGGGCCTGGTGATTACC |
| SEQ ID NO: 21 - DNA | GCGTATACCCTGGCGACCCATACCGCGGGCGTGATTCCGGCGG<br>GCAAACTGGAACGCGTGGATCCGACCACCGTGCGCCAGGAAG<br>GCCCGTGGGCGGATCCGGCGCAGGCGGTGGTGCAGACCGGCC<br>CGAACCAGTATACCGTGTATGTGCTGGCGTTTGCGTTTGGCTAT<br>CAGCCGAACCCGATTGAAGTGCCGCAGGGCGCGGAAATTGTGT<br>TTAAAATTACCAGCCCGGATGTGATTCATGGCTTTCATGTGGA<br>AGGCACCAACATTAACGTGGAAGTGCTGCCGGGCGAAGTGAG<br>CACCGTGCGCTATACCTTTAAACGCCCGGGCGAATATCGCATT<br>ATTTGCAACCAGTATTGCGGCCTGGGCCATCAGAACATGTTTG<br>GCACCATTGTGGTGAAAGAA |
| SEQ ID NO: 22 - peptide | GDVQKKRWLFETKPLD |
| SEQ ID NO: 23 - peptide | VQSKCGSKDNIKHVPGGG |
| SEQ ID NO: 24 - peptide | MERPYACPVESCDRRFSDSSNLTRHIRIHTGQKPFQCRICMRNFSR<br>SDHLTTHIRTHTGEKPFACDICGRKFARSDERKRHTKIHLRQKD |
| SEQ ID NO: 25 - peptide | GTGAGCAAGGGCGAGGAGGATAACATGGCCATCATCAAGGAG<br>TTCATGCGCTTCAAGGTGCACATGGAGGGCTCCGTGAACGGCC<br>ACGAGTTCGAGATCGAGGGCGAGGGCGAGGGCCGCCCCTACG<br>AGGGCACCCAGACCGCCAAGCTGAAGGTGACCAAGGGTGGCC<br>CCCTGCCCTTCGCCTGGGACATCCTGTCCCCTCAGTTCATGTAC<br>GGCTCCAAGGCCTACGTGAAGCACCCCGCCGACATCCCCGACT<br>ACTTGAAGCTGTCCTTCCCCGAGGGCTTCAAGTGGGAGCGCGT<br>GATGAACTTCGAGGACGGCGGCGTGGTGACCGTGACCCAGGA<br>CTCCTCCCTCCAGGACGGCGAGTTCATCTACAAGGTGAAGCTG<br>CGCGGCACCAACTTCCCCTCCGACGGCCCCGTAATGCAGAAGA<br>AGACCATGGGCTGGGAGGCCTCCTCCGAGCGGATGTACCCCGA<br>GGACGGCGCCCTGAAGGGCGAGATCAAGCAGAGGCTGAAGCT<br>GAAGGACGGCGGCCACTACGACGCTGAGGTCAAGACCACCTA<br>CAAGGCCAAGAAGCCCGTGCAGCTGCCCGGCGCCTACAACGTC<br>AACATCAAGTTGGACATCACCTCCCACAACGAGGACTACACCA<br>TCGTGGAACAGTACGAACGCGCCGAGGGCCGCCACTCCACCGG<br>CGGCATGGACGAGCTGTACAAGTAGTAATCTAGAGGGCCCTAT<br>TCTATAGTGTCACC |
| SEQ ID NO: 26 - DNA | ATCCCGCTCATATGCCGGCCAAGACCCTTG |
| SEQ ID NO: 27 - DNA | ATCCCGCTCTCGAGTCAATCGGACAGCTCGATATC |
| SEQ ID NO: 28 - DNA | ATCCCGCTCATATGAAAATAACTTATCCCTTGCCA |
| SEQ ID NO: 29 - DNA | ATCCCGCTCTCGAGTTAGGTAATCACCAAACCAAGT |

The invention claimed is:

1. A genome-editing complex for modifying a target polynucleotide comprising a recombinant β helical protein, represented by a sequence selected from the group consisting of SEQ ID NO: 1, SEQ ID: 2, SEQ ID: 3, SEQ ID: 4, SEQ ID: 5, SEQ ID: 6, SEQ ID: 7, SEQ ID: 8, SEQ ID: 9, SEQ ID: 10, SEQ ID: 11, SEQ ID: 12, and combinations thereof, wherein the recombinant β helical protein is linked to a component selected from the group consisting of: one or more molecules of a genome-editing system and a plasmid that encodes one or more molecules of a genome-editing system, wherein the recombinant β helical protein length is in the range of from 5 to 25 nanometers, and width is in the range from 1 to 5 nanometers.

2. The genome-editing complex of claim 1, wherein the one or more molecules of a genome editing system are selected from the group consisting of:
   a. a RNA-guided endonuclease and/or a guide RNA (gRNA);
   b. a zinc finger nuclease (ZFN);
   c. a transcriptor activator-like effector nuclease;
   d. a DNA-guided endonuclease and/or a guide DNA;
   e. a homing endonuclease;
   f. an integrase.

3. The genome-editing complex of claim 2, wherein the one or more molecules of a genome editing system is the RNA-guided endonuclease and/or the guide RNA (gRNA).

4. The genome-editing complex of claim 2, wherein the RNA-guided endonuclease is Cas9.

5. The genome-editing complex of claim 2, wherein the gRNA has a sequence complementary to a target sequence in the target polynucleotide.

6. The genome-editing complex of claim 1, wherein the modification is addition, deletion, or substitution of one or more nucleotides in the target polynucleotide.

7. The genome-editing complex of claim 1, wherein the β helical protein has a generally quadrangular tip shape.

8. The genome-editing complex of claim 1, wherein the β helical protein comprises one or more amino acid ladder structures selected from the group consisting of an arginine ladder; a lysine ladder; an asparagine ladder; an aspartic acid ladder; and a glutamic acid ladder.

9. The genome-editing complex of claim 8, wherein when present, the arginine ladder comprises from 10 to 20 arginine residues; the lysine ladder comprises from 10 to 30 lysine residues; the asparagine ladder comprises from 10 to 40 asparagine residues; the aspartic acid ladder comprises from 10 to 40 aspartic acid residues; and the glutamic acid ladder comprises from 10 to 40 glutamic acid residues.

10. The genome-editing complex of claim 1, wherein the β helical protein has a total charge that is less than zero.

11. The genome-editing complex of claim 10, wherein the β helical protein has a total charge of from −20 to −60.

12. The genome-editing complex of claim 1, wherein the β helical protein has a β helical structure with a stiffness parameter K (beta helix) 0.2 to 12 N/m$^2$, as measured by atomic force microscopy.

13. The genome-editing complex of claim 1, wherein the β helical protein is a pentapeptide-repeat protein.

14. The genome-editing complex of claim 13, wherein the β helical protein comprises a tandemly repeated pentapeptide with consensus sequence $(STAV)_1(DN)_2(LF)_3(STR)_4(G)_5$.

15. The genome-editing complex of claim 1, wherein the recombinant β helical protein is linked to the one or more molecules of a genome-editing system, or the plasmid, by non-covalent interactions.

16. The genome-editing complex of claim 15, wherein the non-covalent interactions are selected from the group comprising hydrogen bonding, electrostatic interactions, van der Waal's interactions, hydrophobic interactions, or combinations thereof.

17. The genome-editing complex of claim 1, wherein the recombinant β helical protein is linked to the one or more molecules of a genome-editing system, or the plasmid, by a linker molecule selected from the group consisting of: polyethyleneglycol (PEG); ethylene diamine; peptide; metal conjugate, drug-metal conjugate, DNA binding domain, nucleic acid intercalating molecule and combinations thereof.

18. The genome-editing complex of claim 17, wherein when the linker molecule is a peptide, the peptide comprises amino acids selected from the group consisting of: aliphatic amino acids; aromatic amino acids; and combinations thereof.

19. The genome-editing complex of claim 1, wherein a linker is linked to the recombinant β helical protein by covalent bonds.

20. The genome-editing complex of claim 1, wherein the recombinant β helical protein is linked to the one or more molecules of a genome-editing system, or the plasmid, by an ester linkage or an amide linkage.

21. The genome-editing complex of claim 1, wherein the genome-editing complex further comprises a signal sequence wherein the signal sequence directs the genome-editing complex to a particular cell or part of a cell.

22. The genome-editing complex of claim 21, wherein the signal sequence is selected from the group consisting of SEQ ID NO: 14, SEQ ID NO: 15, SEQ ID NO: 16, and SEQ ID NO: 17.

23. The genome-editing complex of claim 21, wherein the genome-editing complex transfers the one or more molecules of a genome-editing system or the plasmid to a location selected from the group consisting of: cell organelles; nucleus; and P-cadherin overexpressing breast cancer cells.

24. The genome-editing complex of claim 1, wherein the genome-editing complex further comprises a phosphatidyl choline molecule.

* * * * *

SEQUENCE LISTING

<160> NUMBER OF SEQ ID NOS: 29

<210> SEQ ID NO 1
<211> LENGTH: 200
<212> TYPE: PRT
<213> ORGANISM: Artificial Sequence
<220> FEATURE:
<223> OTHER INFORMATION: Amino acid sequence of AlbG protein

<400> SEQUENCE: 1

Met Pro Ala Lys Thr Leu Glu Ser Lys Asp Tyr Cys Gly Glu Ser Phe
1               5                   10                  15

Val Ser Glu Asp Arg Ser Gly Gln Ser Leu Glu Ser Ile Arg Phe Glu
            20                  25                  30

Asp Cys Thr Phe Arg Gln Cys Asn Phe Thr Glu Ala Glu Leu Asn Arg
        35                  40                  45

Cys Lys Phe Arg Glu Cys Glu Phe Val Asp Cys Asn Leu Ser Leu Ile
    50                  55                  60

Ser Ile Pro Gln Thr Ser Phe Met Glu Val Arg Phe Val Asp Cys Lys
65                  70                  75                  80

Met Leu Gly Val Asn Trp Thr Ser Ala Gln Trp Pro Ser Val Lys Met
                85                  90                  95

Glu Gly Ala Leu Ser Phe Glu Arg Cys Ile Leu Asn Asp Ser Leu Phe
            100                 105                 110

Tyr Gly Leu Tyr Leu Ala Gly Val Lys Met Val Glu Cys Arg Ile His
        115                 120                 125

Asp Ala Asn Phe Thr Glu Ala Asp Cys Glu Asp Ala Asp Phe Thr Gln
    130                 135                 140

Ser Asp Leu Lys Gly Ser Thr Phe His Asn Thr Lys Leu Thr Gly Ala
145                 150                 155                 160

Ser Phe Ile Asp Ala Val Asn Tyr His Ile Asp Ile Phe His Asn Asp
                165                 170                 175

Ile Lys Arg Ala Arg Phe Ser Leu Pro Glu Ala Ala Ser Leu Leu Asn
            180                 185                 190

Ser Leu Asp Ile Glu Leu Ser Asp
        195                 200

<210> SEQ ID NO 2
<211> LENGTH: 214
<212> TYPE: PRT
<213> ORGANISM: Artificial Sequence
<220> FEATURE:
<223> OTHER INFORMATION: Amino acid sequence of EfsQNR protein

<400> SEQUENCE: 2

Gly Ser His Met Lys Ile Thr Tyr Pro Leu Pro Pro Asn Leu Pro Glu
1               5                   10                  15

Gln Leu Pro Leu Leu Thr Asn Cys Gln Leu Glu Asp Glu Ala Ile Leu
            20                  25                  30

Glu Asn His Leu Tyr Gln Gln Ile Asp Leu Pro Asn Gln Glu Val Arg
        35                  40                  45

Asn Leu Val Phe Arg Asp Ala Val Phe Asp His Leu Ser Leu Ala Asn
    50                  55                  60

Gly Gln Phe Ala Ser Phe Asp Cys Ser Asn Val Arg Phe Glu Ala Cys
65                  70                  75                  80

Asp Phe Ser Asn Val Glu Trp Leu Ser Gly Ser Phe His Arg Val Thr
                85                  90                  95

```
Phe Leu Arg Cys Asn Leu Thr Gly Thr Asn Phe Ala Asp Ser Tyr Leu
            100                 105                 110
Lys Asp Cys Leu Phe Glu Asp Cys Lys Ala Asp Tyr Ala Ser Phe Arg
        115                 120                 125
Phe Ala Asn Phe Asn Leu Val His Phe Asn Gln Thr Arg Leu Val Glu
    130                 135                 140
Ser Glu Phe Phe Glu Val Thr Trp Lys Lys Leu Leu Glu Ala Cys
145                 150                 155                 160
Asp Leu Thr Glu Ser Asn Trp Leu Asn Thr Ser Leu Lys Gly Leu Asp
                165                 170                 175
Phe Ser Gln Asn Thr Phe Glu Arg Leu Thr Phe Ser Pro Asn Tyr Leu
            180                 185                 190
Ser Gly Leu Lys Val Thr Pro Glu Gln Ala Ile Tyr Leu Ala Ser Ala
        195                 200                 205
Leu Gly Leu Val Ile Thr
        210

<210> SEQ ID NO 3
<211> LENGTH: 84
<212> TYPE: PRT
<213> ORGANISM: Tenebrio molitor
<220> FEATURE:
<223> OTHER INFORMATION: Amino acid sequence of anti-freeze protein from
      Tenebrio molitor

<400> SEQUENCE: 3

Gln Cys Thr Gly Gly Ala Asp Cys Thr Ser Cys Thr Gly Ala Cys Thr
1               5                   10                  15
Gly Cys Gly Asn Cys Pro Asn Ala Val Thr Cys Thr Asn Ser Gln His
            20                  25                  30
Cys Val Lys Ala Asn Thr Cys Thr Gly Ser Thr Asp Cys Asn Thr Ala
        35                  40                  45
Gln Thr Cys Thr Asn Ser Lys Asp Cys Phe Glu Ala Asn Thr Cys Thr
    50                  55                  60
Asp Ser Thr Asn Cys Tyr Lys Ala Thr Ala Cys Thr Asn Ser Ser Gly
65                  70                  75                  80
Cys Pro Gly His

<210> SEQ ID NO 4
<211> LENGTH: 143
<212> TYPE: PRT
<213> ORGANISM: Rhagium inquisitor
<220> FEATURE:
<223> OTHER INFORMATION: Acid sequence of anti-freeze protein from
      Rhagium inquisitor

<400> SEQUENCE: 4

Gly Tyr Ser Cys Arg Ala Val Gly Val Asp Gly Arg Ala Val Thr Asp
1               5                   10                  15
Ile Gln Gly Thr Cys His Ala Lys Ala Thr Gly Ala Gly Ala Met Ala
            20                  25                  30
Ser Gly Thr Ser Glu Pro Gly Ser Thr Ser Ala Thr Ala Thr Gly
        35                  40                  45
Arg Gly Ala Thr Ala Arg Ser Thr Ser Thr Gly Arg Gly Thr Ala Thr
    50                  55                  60
Thr Thr Ala Thr Gly Thr Ala Ser Ala Thr Ser Asn Ala Ile Gly Gln
65                  70                  75                  80
```

```
Gly Thr Ala Thr Thr Ala Thr Gly Ser Ala Gly Arg Ala Thr
                85                  90                  95

Gly Ser Ala Thr Thr Ser Ser Ala Ser Gln Pro Thr Gln Thr Gln
                100                 105                 110

Thr Ile Thr Gly Pro Gly Phe Gln Thr Ala Lys Ser Phe Ala Arg Asn
        115                 120                 125

Thr Ala Thr Thr Thr Val Thr Ala Ser His His His His His His
        130                 135                 140

<210> SEQ ID NO 5
<211> LENGTH: 90
<212> TYPE: PRT
<213> ORGANISM: Choristoneura fumiferana
<220> FEATURE:
<223> OTHER INFORMATION: Amino acid sequence of anti-freeze protein from
      Spruce Budworm

<400> SEQUENCE: 5

Asp Gly Ser Cys Thr Asn Thr Asn Ser Gln Leu Ser Ala Asn Ser Lys
1               5                   10                  15

Cys Glu Lys Ser Thr Leu Thr Asn Cys Tyr Val Asp Lys Ser Glu Val
                20                  25                  30

Tyr Gly Thr Thr Cys Thr Gly Ser Arg Phe Asp Gly Val Thr Ile Thr
        35                  40                  45

Thr Ser Thr Ser Thr Gly Ser Arg Ile Ser Gly Pro Gly Cys Lys Ile
    50                  55                  60

Ser Thr Cys Ile Ile Thr Gly Gly Val Pro Ala Pro Ser Ala Ala Cys
65                  70                  75                  80

Lys Ile Ser Gly Cys Thr Phe Ser Ala Asn
                85                  90

<210> SEQ ID NO 6
<211> LENGTH: 217
<212> TYPE: PRT
<213> ORGANISM: Artificial Sequence
<220> FEATURE:
<223> OTHER INFORMATION: Amino acid sequence of QNRB1 protein

<400> SEQUENCE: 6

Gly Ser His Met Ala Leu Ala Leu Val Gly Glu Lys Ile Asp Arg Asn
1               5                   10                  15

Arg Phe Thr Gly Glu Lys Ile Glu Asn Ser Thr Phe Phe Asn Cys Asp
                20                  25                  30

Phe Ser Gly Ala Asp Leu Ser Gly Thr Glu Phe Ile Gly Cys Gln Phe
        35                  40                  45

Tyr Asp Arg Glu Ser Gln Lys Gly Cys Asn Phe Ser Arg Ala Met Leu
    50                  55                  60

Lys Asp Ala Ile Phe Lys Ser Cys Asp Leu Ser Met Ala Asp Phe Arg
65                  70                  75                  80

Asn Ser Ser Ala Leu Gly Ile Glu Ile Arg His Cys Arg Ala Gln Gly
                85                  90                  95

Ala Asp Phe Arg Gly Ala Ser Phe Met Asn Met Ile Thr Thr Arg Thr
                100                 105                 110

Trp Phe Cys Ser Ala Tyr Ile Thr Asn Thr Asn Leu Ser Tyr Ala Asn
        115                 120                 125

Phe Ser Lys Val Val Leu Glu Lys Cys Glu Leu Trp Glu Asn Arg Trp
    130                 135                 140
```

```
Ile Gly Ala Gln Val Leu Gly Ala Thr Phe Ser Gly Ser Asp Leu Ser
145                 150                 155                 160

Gly Gly Glu Phe Ser Thr Phe Asp Trp Arg Ala Ala Asn Phe Thr His
                165                 170                 175

Cys Asp Leu Thr Asn Ser Glu Leu Gly Asp Leu Asp Ile Arg Gly Val
                180                 185                 190

Asp Leu Gln Gly Val Lys Leu Asp Asn Tyr Gln Ala Ser Leu Leu Met
            195                 200                 205

Glu Arg Leu Gly Ile Ala Val Ile Gly
210                 215
```

<210> SEQ ID NO 7
<211> LENGTH: 262
<212> TYPE: PRT
<213> ORGANISM: Artificial Sequence
<220> FEATURE:
<223> OTHER INFORMATION: Amino acid sequence of UDP-N-acetylglucosamine
      acyltransferase protein

<400> SEQUENCE: 7

```
Met Ile Asp Lys Ser Ala Phe Val His Pro Thr Ala Ile Val Glu Glu
1               5                   10                  15

Gly Ala Ser Ile Gly Ala Asn Ala His Ile Gly Pro Phe Cys Ile Val
                20                  25                  30

Gly Pro His Val Glu Ile Gly Glu Gly Thr Val Leu Lys Ser His Val
            35                  40                  45

Val Val Asn Gly His Thr Lys Ile Gly Arg Asp Asn Glu Ile Tyr Gln
50                  55                  60

Phe Ala Ser Ile Gly Glu Val Asn Gln Asp Leu Lys Tyr Ala Gly Glu
65                  70                  75                  80

Pro Thr Arg Val Glu Ile Gly Asp Arg Asn Arg Ile Arg Glu Ser Val
                85                  90                  95

Thr Ile His Arg Gly Thr Val Gln Gly Gly Gly Leu Thr Lys Val Gly
            100                 105                 110

Ser Asp Asn Leu Leu Met Ile Asn Ala His Ile Ala His Asp Cys Thr
            115                 120                 125

Val Gly Asn Arg Cys Ile Leu Ala Asn Asn Ala Thr Leu Ala Gly His
130                 135                 140

Val Ser Val Asp Asp Phe Ala Ile Ile Gly Gly Met Thr Ala Val His
145                 150                 155                 160

Gln Phe Cys Ile Ile Gly Ala His Val Met Val Gly Gly Cys Ser Gly
                165                 170                 175

Val Ala Gln Asp Val Pro Pro Tyr Val Ile Ala Gln Gly Asn His Ala
            180                 185                 190

Thr Pro Phe Gly Val Asn Ile Glu Gly Leu Lys Arg Arg Gly Phe Ser
            195                 200                 205

Arg Glu Ala Ile Thr Ala Ile Arg Asn Ala Tyr Lys Leu Ile Tyr Arg
210                 215                 220

Ser Gly Lys Thr Leu Asp Glu Val Lys Pro Glu Ile Ala Glu Leu Ala
225                 230                 235                 240

Glu Thr Tyr Pro Glu Val Lys Ala Phe Thr Asp Phe Phe Ala Arg Ser
                245                 250                 255

Thr Arg Gly Leu Ile Arg
            260
```

<210> SEQ ID NO 8

<211> LENGTH: 201
<212> TYPE: PRT
<213> ORGANISM: Artificial Sequence
<220> FEATURE:
<223> OTHER INFORMATION: Amino acid sequence of NP275 protein from Nostoc punctiforme

<400> SEQUENCE: 8

```
Met Gly Ser Ser His His His His His Ser Ser Gly Leu Val Pro
1               5                   10                  15

Arg Gly Ser His Met Asp Val Glu Lys Leu Arg Gln Leu Tyr Ala Ala
            20                  25                  30

Gly Glu Arg Asp Phe Ser Ile Val Asp Leu Arg Gly Ala Val Leu Glu
        35                  40                  45

Asn Ile Asn Leu Ser Gly Ala Ile Leu His Gly Ala Met Leu Asp Glu
50                  55                  60

Ala Asn Leu Gln Gln Ala Asn Leu Ser Arg Ala Asp Leu Ser Gly Ala
65                  70                  75                  80

Thr Leu Asn Gly Ala Asp Leu Arg Gly Ala Asn Leu Ser Lys Ala Asp
                85                  90                  95

Leu Ser Asp Ala Ile Leu Asp Asn Ala Ile Leu Glu Gly Ala Ile Leu
            100                 105                 110

Asp Glu Ala Val Leu Asn Gln Ala Asn Leu Lys Ala Ala Asn Leu Glu
        115                 120                 125

Gln Ala Ile Leu Ser His Ala Asn Ile Arg Glu Ala Asp Leu Ser Glu
    130                 135                 140

Ala Asn Leu Glu Ala Ala Asp Leu Ser Gly Ala Asp Leu Ala Ile Ala
145                 150                 155                 160

Asp Leu His Gln Ala Asn Leu His Gln Ala Leu Glu Arg Ala Asn
                165                 170                 175

Leu Thr Gly Ala Asn Leu Glu Asp Ala Asn Leu Glu Gly Thr Ile Leu
            180                 185                 190

Glu Gly Gly Asn Asn Asn Leu Ala Thr
        195                 200
```

<210> SEQ ID NO 9
<211> LENGTH: 353
<212> TYPE: PRT
<213> ORGANISM: Artificial Sequence
<220> FEATURE:
<223> OTHER INFORMATION: Amino acid sequence of pectate lyase C protein

<400> SEQUENCE: 9

```
Ala Thr Asp Thr Gly Gly Tyr Ala Ala Thr Ala Gly Gly Asn Val Thr
1               5                   10                  15

Gly Ala Val Ser Lys Thr Ala Thr Ser Met Gln Asp Ile Val Asn Ile
            20                  25                  30

Ile Asp Ala Ala Arg Leu Asp Ala Asn Gly Lys Lys Val Lys Gly Gly
        35                  40                  45

Ala Tyr Pro Leu Val Ile Thr Tyr Thr Gly Asn Glu Asp Ser Leu Ile
    50                  55                  60

Asn Ala Ala Ala Ala Asn Ile Cys Gly Gln Trp Ser Lys Asp Pro Arg
65                  70                  75                  80

Gly Val Glu Ile Lys Glu Phe Thr Lys Gly Ile Thr Ile Ile Gly Ala
                85                  90                  95

Asn Gly Ser Ser Ala Asn Phe Gly Ile Trp Ile Lys Lys Ser Ser Asp
            100                 105                 110
```

```
Val Val Val Gln Asn Met Arg Ile Gly Tyr Leu Pro Gly Gly Ala Lys
            115                 120                 125

Asp Gly Asp Met Ile Arg Val Asp Asp Ser Pro Asn Val Trp Val Asp
        130                 135                 140

His Asn Glu Leu Phe Ala Ala Asn His Glu Cys Asp Gly Thr Pro Asp
145                 150                 155                 160

Asn Asp Thr Thr Phe Glu Ser Ala Val Asp Ile Lys Gly Ala Ser Asn
                165                 170                 175

Thr Val Thr Val Ser Tyr Asn Tyr Ile His Gly Val Lys Lys Val Gly
            180                 185                 190

Leu Asp Gly Ser Ser Ser Asp Thr Gly Arg Asn Ile Thr Tyr His
        195                 200                 205

His Asn Tyr Tyr Asn Asp Val Asn Ala Arg Leu Pro Leu Gln Arg Gly
            210                 215                 220

Gly Leu Val His Ala Tyr Asn Asn Leu Tyr Thr Asn Ile Thr Gly Ser
225                 230                 235                 240

Gly Leu Asn Val Arg Gln Asn Gly Gln Ala Leu Ile Glu Asn Asn Trp
                245                 250                 255

Phe Glu Lys Ala Ile Asn Pro Val Thr Ser Arg Tyr Asp Gly Lys Asn
            260                 265                 270

Phe Gly Thr Trp Val Leu Lys Gly Asn Asn Ile Thr Lys Pro Ala Asp
        275                 280                 285

Phe Ser Thr Tyr Ser Ile Thr Trp Thr Ala Asp Thr Lys Pro Tyr Val
            290                 295                 300

Asn Ala Asp Ser Trp Thr Ser Thr Gly Thr Phe Pro Thr Val Ala Tyr
305                 310                 315                 320

Asn Tyr Ser Pro Val Ser Ala Gln Cys Val Lys Asp Lys Leu Pro Gly
                325                 330                 335

Tyr Ala Gly Val Gly Lys Asn Leu Ala Thr Leu Thr Ser Thr Ala Cys
            340                 345                 350

Lys

<210> SEQ ID NO 10
<211> LENGTH: 196
<212> TYPE: PRT
<213> ORGANISM: Caldicellulosiruptor bescii
<220> FEATURE:
<223> OTHER INFORMATION: Amino acid sequence of pectate lyase from
      Caldicellulosiruptor bescii

<400> SEQUENCE: 10

Val Gly Thr Asn Thr Gly Gly Val Leu Val Ile Thr Asp Thr Ile Ile
1               5                   10                  15

Val Lys Ser Gly Gln Thr Tyr Asp Gly Lys Gly Ile Lys Ile Ile Ala
            20                  25                  30

Gln Gly Met Gly Asp Gly Ser Gln Ser Glu Asn Gln Lys Pro Ile Phe
        35                  40                  45

Lys Leu Glu Lys Gly Ala Asn Leu Lys Asn Val Ile Ile Gly Ala Pro
    50                  55                  60

Gly Cys Asp Gly Ile His Cys Tyr Gly Asp Asn Val Val Glu Asn Val
65                  70                  75                  80

Val Trp Glu Asp Val Gly Glu Asp Ala Leu Thr Val Lys Ser Glu Gly
                85                  90                  95

Val Val Glu Val Ile Gly Gly Ser Ala Lys Glu Ala Ala Asp Lys Val
            100                 105                 110
```

```
Phe Gln Leu Asn Ala Pro Cys Thr Phe Lys Val Lys Asn Phe Thr Ala
            115                 120                 125

Thr Asn Ile Gly Lys Leu Val Arg Gln Asn Gly Asn Thr Thr Phe Lys
130                 135                 140

Val Val Ile Tyr Leu Glu Asp Val Thr Leu Asn Asn Val Lys Ser Cys
145                 150                 155                 160

Val Ala Lys Ser Asp Ser Pro Val Ser Glu Leu Trp Tyr His Asn Leu
            165                 170                 175

Asn Val Asn Asn Cys Lys Thr Leu Phe Glu Phe Pro Ser Gln Ser Gln
            180                 185                 190

Ile His Gln Tyr
        195

<210> SEQ ID NO 11
<211> LENGTH: 213
<212> TYPE: PRT
<213> ORGANISM: Methanosarcina thermophila
<220> FEATURE:
<223> OTHER INFORMATION: Amino acid sequence of carbonic anhydrase from
      Methanosarcina thermophila

<400> SEQUENCE: 11

Gln Glu Ile Thr Val Asp Glu Phe Ser Asn Ile Arg Glu Asn Pro Val
1               5                   10                  15

Thr Pro Trp Asn Pro Glu Pro Ser Ala Pro Val Ile Asp Pro Thr Ala
            20                  25                  30

Tyr Ile Asp Pro Gln Ala Ser Val Ile Gly Glu Val Thr Ile Gly Ala
        35                  40                  45

Asn Val Met Val Ser Pro Met Ala Ser Ile Arg Ser Asp Glu Gly Met
50                  55                  60

Pro Ile Phe Val Gly Asp Arg Ser Asn Val Gln Asp Gly Val Val Leu
65                  70                  75                  80

His Ala Leu Glu Thr Ile Asn Glu Glu Gly Glu Pro Ile Glu Asp Asn
            85                  90                  95

Ile Val Glu Val Asp Gly Lys Glu Tyr Ala Val Tyr Ile Gly Asn Asn
        100                 105                 110

Val Ser Leu Ala His Gln Ser Gln Val His Gly Pro Ala Ala Val Gly
            115                 120                 125

Asp Asp Thr Phe Ile Gly Met Gln Ala Phe Val Phe Lys Ser Lys Val
130                 135                 140

Gly Asn Asn Cys Val Leu Glu Pro Arg Ser Ala Ala Ile Gly Val Thr
145                 150                 155                 160

Ile Pro Asp Gly Arg Tyr Ile Pro Ala Gly Met Val Val Thr Ser Gln
            165                 170                 175

Ala Glu Ala Asp Lys Leu Pro Glu Val Thr Asp Asp Tyr Ala Tyr Ser
            180                 185                 190

His Thr Asn Glu Ala Val Val Tyr Val Asn Val His Leu Ala Glu Gly
            195                 200                 205

Tyr Lys Glu Thr Ser
210

<210> SEQ ID NO 12
<211> LENGTH: 359
<212> TYPE: PRT
<213> ORGANISM: Aspergillus niger
<220> FEATURE:
<223> OTHER INFORMATION: Amino acid sequence of Pectin lyase A protein
      from Aspergillus niger
```

<400> SEQUENCE: 12

```
Val Gly Val Ser Gly Ser Ala Glu Gly Phe Ala Lys Gly Val Thr Gly
1               5                   10                  15

Gly Gly Ser Ala Thr Pro Val Tyr Pro Asp Thr Ile Asp Glu Leu Val
            20                  25                  30

Ser Tyr Leu Gly Asp Asp Glu Ala Arg Val Ile Val Leu Thr Lys Thr
        35                  40                  45

Phe Asp Phe Thr Asp Ser Glu Gly Thr Thr Thr Gly Thr Gly Cys Ala
50                  55                  60

Pro Trp Gly Thr Ala Ser Ala Cys Gln Val Ala Ile Asp Gln Asp Asp
65                  70                  75                  80

Trp Cys Glu Asn Tyr Glu Pro Asp Ala Pro Ser Val Ser Val Glu Tyr
                85                  90                  95

Tyr Asn Ala Gly Thr Leu Gly Ile Thr Val Thr Ser Asn Lys Ser Leu
            100                 105                 110

Ile Gly Glu Gly Ser Ser Gly Ala Ile Lys Gly Lys Gly Leu Arg Ile
        115                 120                 125

Val Ser Gly Ala Glu Asn Ile Ile Ile Gln Asn Ile Ala Val Thr Asp
130                 135                 140

Ile Asn Pro Lys Tyr Val Trp Gly Gly Asp Ala Ile Thr Leu Asp Asp
145                 150                 155                 160

Cys Asp Leu Val Trp Ile Asp His Val Thr Thr Ala Arg Ile Gly Arg
                165                 170                 175

Gln His Tyr Val Leu Gly Thr Ser Ala Asp Asn Arg Val Ser Leu Thr
            180                 185                 190

Asn Asn Tyr Ile Asp Gly Val Ser Asp Tyr Ser Ala Thr Cys Asp Gly
        195                 200                 205

Tyr His Tyr Trp Ala Ile Tyr Leu Asp Gly Asp Ala Asp Leu Val Thr
210                 215                 220

Met Lys Gly Asn Tyr Ile Tyr His Thr Ser Gly Arg Ser Pro Lys Val
225                 230                 235                 240

Gln Asp Asn Thr Leu Leu His Ala Val Asn Asn Tyr Trp Tyr Asp Ile
                245                 250                 255

Ser Gly His Ala Phe Glu Ile Gly Glu Gly Tyr Val Leu Ala Glu
            260                 265                 270

Gly Asn Val Phe Gln Asn Val Asp Thr Val Leu Glu Thr Tyr Glu Gly
        275                 280                 285

Glu Ala Phe Thr Val Pro Ser Ser Thr Ala Gly Glu Val Cys Ser Thr
290                 295                 300

Tyr Leu Gly Arg Asp Cys Val Ile Asn Gly Phe Gly Ser Ser Gly Thr
305                 310                 315                 320

Phe Ser Glu Asp Ser Thr Ser Phe Leu Ser Asp Phe Glu Gly Lys Asn
                325                 330                 335

Ile Ala Ser Ala Ser Ala Tyr Ser Val Ala Ser Arg Val Val Ala
            340                 345                 350

Asn Ala Gly Gln Gly Asn Leu
        355
```

<210> SEQ ID NO 13
<211> LENGTH: 135
<212> TYPE: PRT
<213> ORGANISM: Artificial Sequence
<220> FEATURE:
<223> OTHER INFORMATION: Amino acid sequence of TtCuA protein

<400> SEQUENCE: 13

Ala Tyr Thr Leu Ala Thr His Thr Ala Gly Val Ile Pro Ala Gly Lys
1               5                   10                  15

Leu Glu Arg Val Asp Pro Thr Thr Val Arg Gln Glu Gly Pro Trp Ala
                20                  25                  30

Asp Pro Ala Gln Ala Val Val Gln Thr Gly Pro Asn Gln Tyr Thr Val
            35                  40                  45

Tyr Val Leu Ala Phe Ala Phe Gly Tyr Gln Pro Asn Pro Ile Glu Val
        50                  55                  60

Pro Gln Gly Ala Glu Ile Val Phe Lys Ile Thr Ser Pro Asp Val Ile
65                  70                  75                  80

His Gly Phe His Val Glu Gly Thr Asn Ile Asn Val Glu Val Leu Pro
                85                  90                  95

Gly Glu Val Ser Thr Val Arg Tyr Thr Phe Lys Arg Pro Gly Glu Tyr
                100                 105                 110

Arg Ile Ile Cys Asn Gln Tyr Cys Gly Leu Gly His Gln Asn Met Phe
            115                 120                 125

Gly Thr Ile Val Val Lys Glu
        130                 135

<210> SEQ ID NO 14
<211> LENGTH: 9
<212> TYPE: PRT
<213> ORGANISM: Artificial Sequence
<220> FEATURE:
<223> OTHER INFORMATION: Signal sequence for targeting the nucleus of
      the cell

<400> SEQUENCE: 14

Pro Ala Ala Lys Arg Val Lys Cys Asp
1               5

<210> SEQ ID NO 15
<211> LENGTH: 13
<212> TYPE: PRT
<213> ORGANISM: Artificial Sequence
<220> FEATURE:
<223> OTHER INFORMATION: Signal sequence for targeting the endoplasmic
      reticulum of the cell

<400> SEQUENCE: 15

Tyr Pro Tyr Asp Val Pro Asp Tyr Ala Lys Asp Glu Leu
1               5                   10

<210> SEQ ID NO 16
<211> LENGTH: 25
<212> TYPE: PRT
<213> ORGANISM: Artificial Sequence
<220> FEATURE:
<223> OTHER INFORMATION: Signal sequence for targeting the mitochondria
      of the cell

<400> SEQUENCE: 16

Met Leu Ser Leu Arg Gln Ser Ile Arg Phe Phe Lys Pro Ala Thr Arg
1               5                   10                  15

Thr Leu Cys Ser Ser Arg Tyr Leu Leu
                20                  25

<210> SEQ ID NO 17
<211> LENGTH: 28
<212> TYPE: PRT

<213> ORGANISM: Artificial Sequence
<220> FEATURE:
<223> OTHER INFORMATION: Signal sequence for targeting the P-cadherin-
over expressing breast cancer cells

<400> SEQUENCE: 17

```
Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25
```

<210> SEQ ID NO 18
<211> LENGTH: 5
<212> TYPE: PRT
<213> ORGANISM: Artificial Sequence
<220> FEATURE:
<223> OTHER INFORMATION: Consensus sequence in a pentapeptide-repeat
protein
<220> FEATURE:
<221> NAME/KEY: misc_feature
<222> LOCATION: (1)..(1)
<223> OTHER INFORMATION: Ser or Thr or Ala or Val
<220> FEATURE:
<221> NAME/KEY: misc_feature
<222> LOCATION: (2)..(2)
<223> OTHER INFORMATION: Asp or Asn
<220> FEATURE:
<221> NAME/KEY: misc_feature
<222> LOCATION: (3)..(3)
<223> OTHER INFORMATION: Leu or Phe
<220> FEATURE:
<221> NAME/KEY: misc_feature
<222> LOCATION: (4)..(4)
<223> OTHER INFORMATION: Ser or Thr or Arg

<400> SEQUENCE: 18

```
Xaa Xaa Xaa Xaa Gly
1               5
```

<210> SEQ ID NO 19
<211> LENGTH: 582
<212> TYPE: DNA
<213> ORGANISM: Artificial Sequence
<220> FEATURE:
<223> OTHER INFORMATION: Nucleic acid sequence of AlbG gene

<400> SEQUENCE: 19

```
atgccggcga aaccctgga  aagcaaagat tattgcggcg aaagctttgt gagcgaagat    60
cgcagcggcc agagcctgga aagcattcgc tttgaagatt gcacctttcg ccagtgcaac   120
tttaccgaag cggaactgaa ccgctgcaaa tttcgcgaat gcgaatttgt ggattgcaac   180
ctgagcctga ttagcattcc gcagaccagc tttatggaag tgcgctttgt ggattgcaaa   240
atgctgggcg tgaactggac cagcgcgcag gcgggcgcgc tgagctttga acgctgcatt   300
ctgaacgata gcctgtttta tggcctgtat ctggcgggcg tgaaaatggt ggaatgccgc   360
attcatgatg cgaactttac cgaagcggat tgcgaagatg cggatttttac ccagagcgat   420 ctgaaaggca gcacctttca taacaccaaa ctgaccggcg cgagctttat tgatgcggtg   480
aactatcata ttgatatttt tcataacgat attaaacgcg cgcgctttag cctgccggaa   540
gcggcgagcc tgctgaacag cctggatatt gaactgagcg at                      582
```

<210> SEQ ID NO 20
<211> LENGTH: 642
<212> TYPE: DNA
<213> ORGANISM: Artificial Sequence
<220> FEATURE:

<223> OTHER INFORMATION: nucleic acid sequence of EfsQNR gene

<400> SEQUENCE: 20

| | | |
|---|---|---|
| ggcagccata tgaaaattac ctatccgctg ccgccgaacc tgccggaaca gctgccgctg | 60 |
| ctgaccaact gccagctgga agatgaagcg attctggaaa accatctgta tcagcagatt | 120 |
| gatctgccga accaggaagt gcgcaacctg gtgtttcgcg atgcggtgtt tgatcatctg | 180 |
| agcctggcga acggccagtt tgcgagcttt gattgcagca acgtgcgctt tgaagcgtgc | 240 |
| gattttagca acgtggaatg gctgagcggc agctttcatc gcgtgacctt tctgcgctgc | 300 |
| aacctgaccg gcaccaactt tgcggatagc tatctgaaag attgcctgtt tgaagattgc | 360 |
| aaagcggatt atgcgagctt tcgctttgcg aactttaacc tggtgcattt taaccagacc | 420 |
| cgcctggtgg aaagcgaatt ttttgaagtg acctggaaaa aactgctgct ggaagcgtgc | 480 |
| gatctgaccg aaagcaactg gctgaacacc agcctgaaag gcctggattt tagccagaac | 540 |
| acctttgaac gcctgacctt tagcccgaac tatctgagcg gcctgaaagt gaccccggaa | 600 |
| caggcgattt atctggcgag cgcgctgggc ctggtgatta cc | 642 |

<210> SEQ ID NO 21
<211> LENGTH: 405
<212> TYPE: DNA
<213> ORGANISM: Artificial Sequence
<220> FEATURE:
<223> OTHER INFORMATION: Nucleic acid sequence of TtCuA gene

<400> SEQUENCE: 21

| | | |
|---|---|---|
| gcgtataccc tggcgaccca taccgcgggc gtgattccgg cgggcaaact ggaacgcgtg | 60 |
| gatccgacca ccgtgcgcca ggaaggcccg tgggcggatc cggcgcaggc ggtggtgcag | 120 |
| accggcccga accagtatac cgtgtatgtg ctggcgtttg cgtttggcta tcagccgaac | 180 |
| ccgattgaag tgccgcaggg cgcggaaatt gtgtttaaaa ttaccagccc ggatgtgatt | 240 |
| catggctttc atgtggaagg caccaacatt aacgtggaag tgctgccggg cgaagtgagc | 300 |
| accgtgcgct ataccttaa cgcccgggc gaatatcgca ttatttgcaa ccagtattgc | 360 |
| ggcctgggcc atcagaacat gtttggcacc attgtggtga agaa | 405 |

<210> SEQ ID NO 22
<211> LENGTH: 16
<212> TYPE: PRT
<213> ORGANISM: Artificial Sequence
<220> FEATURE:
<223> OTHER INFORMATION: Signal sequence for targeting actin in the cell

<400> SEQUENCE: 22

Gly Asp Val Gln Lys Lys Arg Trp Leu Phe Glu Thr Lys Pro Leu Asp
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Signal sequence for targeting tubulin in the
      cell

<400> SEQUENCE: 23

Val Gln Ser Lys Cys Gly Ser Lys Asp Asn Ile Lys His Val Pro Gly
1               5                   10                  15

Gly Gly

<210> SEQ ID NO 24
<211> LENGTH: 90
<212> TYPE: PRT
<213> ORGANISM: Artificial Sequence
<220> FEATURE:
<223> OTHER INFORMATION: Amino acid sequence of a zinc finger protein

<400> SEQUENCE: 24

Met Glu Arg Pro Tyr Ala Cys Pro Val Glu Ser Cys Asp Arg Arg Phe
1               5                   10                  15

Ser Asp Ser Ser Asn Leu Thr Arg His Ile Arg Ile His Thr Gly Gln
            20                  25                  30

Lys Pro Phe Gln Cys Arg Ile Cys Met Arg Asn Phe Ser Arg Ser Asp
        35                  40                  45

His Leu Thr Thr His Ile Arg Thr His Thr Gly Glu Lys Pro Phe Ala
    50                  55                  60

Cys Asp Ile Cys Gly Arg Lys Phe Ala Arg Ser Asp Glu Arg Lys Arg
65                  70                  75                  80

His Thr Lys Ile His Leu Arg Gln Lys Asp
                85                  90

<210> SEQ ID NO 25
<211> LENGTH: 740
<212> TYPE: DNA
<213> ORGANISM: Artificial Sequence
<220> FEATURE:
<223> OTHER INFORMATION: Nucleic acid sequence of mcherry gene

<400> SEQUENCE: 25
gtgagcaagg gcgaggagga taacatggcc atcatcaagg agttcatgcg cttcaaggtg      60
cacatggagg gctccgtgaa cggccacgag ttcgagatcg agggcgaggg cgagggccgc     120
ccctacgagg gcacccagac cgccaagctg aaggtgacca agggtggccc cctgcccttc     180
gcctgggaca tcctgtcccc tcagttcatg tacggctcca aggcctacgt gaagcacccc     240
gccgacatcc ccgactactt gaagctgtcc ttccccgagg gcttcaagtg ggagcgcgtg     300
atgaacttcg aggacggcgg cgtggtgacc gtgacccagg actcctccct ccaggacggc     360
gagttcatct acaaggtgaa gctgcgcggc accaacttcc cctccgacgg ccccgtaatg     420
cagaagaaga ccatgggctg ggaggcctcc tccgagcgga tgtaccccga ggacggcgcc     480
ctgaagggcg agatcaagca gaggctgaag ctgaaggacg gcggccacta cgacgctgag     540
gtcaagacca cctacaaggc caagaagccc gtgcagctgc ccggcgccta caacgtcaac     600
atcaagttgg acatcaccct ccacaacgag gactacacca tcgtggaaca gtacgaacgc     660
gccgagggcc gccactccac cggcggcatg gacgagctgt acaagtagta atctagaggg     720
ccctattcta tagtgtcacc                                                 740

<210> SEQ ID NO 26
<211> LENGTH: 30
<212> TYPE: DNA
<213> ORGANISM: Artificial Sequence
<220> FEATURE:
<223> OTHER INFORMATION: Nucleic acid sequence of a PCR primer AlbG gene

<400> SEQUENCE: 26
atcccgctca tatgccggcc aagacccttg                                       30

<210> SEQ ID NO 27
<211> LENGTH: 35

```
<212> TYPE: DNA
<213> ORGANISM: Artificial Sequence
<220> FEATURE:
<223> OTHER INFORMATION: Nucleic acid sequence of a PCR primer AlbG gene

<400> SEQUENCE: 27
atcccgctct cgagtcaatc ggacagctcg atatc                              35

<210> SEQ ID NO 28
<211> LENGTH: 35
<212> TYPE: DNA
<213> ORGANISM: Artificial Sequence
<220> FEATURE:
<223> OTHER INFORMATION: Nucleic acid sequence of a PCR primer EfsQNR
      gene

<400> SEQUENCE: 28
atcccgctca tatgaaaata acttatccct tgcca                              35

<210> SEQ ID NO 29
<211> LENGTH: 36
<212> TYPE: DNA
<213> ORGANISM: Artificial Sequence
<220> FEATURE:
<223> OTHER INFORMATION: Nucleic acid sequence of a PCR primer EfsQNR
      gene

<400> SEQUENCE: 29
atcccgctct cgagttaggt aatcaccaaa ccaagt                             36
```